United States Patent [19]
Bateson et al.

[11] Patent Number: 6,077,952
[45] Date of Patent: Jun. 20, 2000

[54] CEPHALOPORINS AND HOMOLOGUES

[75] Inventors: John Hargreaves Bateson; George Burton; Stephen Christopher Martin Fell, all of Betchworth, United Kingdom

[73] Assignee: Pfizer Inc., New York, N.Y.

[21] Appl. No.: 09/327,667

[22] Filed: Jun. 8, 1999

Related U.S. Application Data

[62] Continuation of application No. 09/228,138, Jan. 11, 1999, Pat. No. 6,001,997, which is a continuation of application No. 08/958,864, Oct. 20, 1997, Pat. No. 6,020,329, which is a continuation of application No. 08/470,786, Jun. 6, 1995, abandoned, which is a continuation of application No. 07/934,667, filed as application No. PCT/GB91/01171, Jul. 22, 1991, abandoned.

[30] Foreign Application Priority Data

Jul. 24, 1990 [GB] United Kingdom .................. 9016189
May 2, 1991 [GB] United Kingdom .................. 9109540

[51] Int. Cl.⁷ ................................................. C07D 501/18
[52] U.S. Cl. .......................... 540/300; 540/215; 540/301
[58] Field of Search ..................... 540/300, 301, 540/215

[56] References Cited

U.S. PATENT DOCUMENTS

| | | | |
|---|---|---|---|
| 5,246,926 | 9/1993 | Bateson et al. | 514/202 |
| 5,716,948 | 2/1998 | Burton et al. | 540/205 |
| 6,001,997 | 12/1999 | Bateson et al. | 540/222 |
| 6,020,329 | 2/2000 | Bateson et al. | 514/202 |

OTHER PUBLICATIONS

Nayler et al., Chem. Abst., vol. 80, 1974, 3537t.
Brain et al., J. Med. Chem, 1977., vol. 20, No. 8 Napes 1086.

*Primary Examiner*—Mukund J. Shah
*Assistant Examiner*—Pavanaram K Sripada
*Attorney, Agent, or Firm*—Peter C. Richardson; Paul H. Ginsburg; Lorraine B. Ling

[57] ABSTRACT

A compound of formula (II) or a salt:

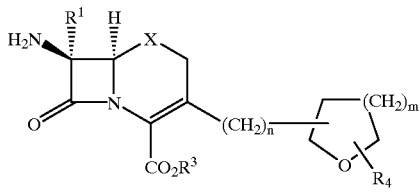

1 Claim, No Drawings

CEPHALOPORINS AND HOMOLOGUES

This application is a continuation of prior pending application, Ser. No. 09/228,138 filed Jan. 11, 1999 U.S. Pat. No. 6,001,997, which is a continuation of prior application, Ser. No. 08/958,864 filed Oct. 20, 1997 U.S. Pat. No. 6,020,329, which is a continuation of prior application Ser. No. 08/470,786 filed Jun. 6, 1995, now abandoned, which is a continuation of prior application Ser. No. 07/934,667 filed Jan. 22, 1993, now abandoned, which was a national stage filing under USC 371 of International Application No. PCT/GB91/01171 filed Jul. 22, 1991.

This invention relates to novel β-lactam containing compounds, their preparation and their use, and in particular to a novel class of cephalosporins. These compounds have antibacterial properties, and are therefore of use in the treatment of bacterial infections in humans and animals caused by a wide range of organisms.

GB 1 385 831 (Hoechst) claims 7-acylamino-cephem-carboxylic acid compounds substituted at the 7-position by a group:

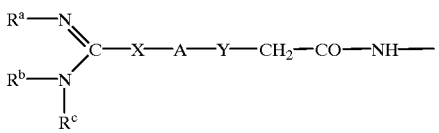

in which $R^a$ and $R^b$, which may be the same or different, each represents a hydrogen atom or an alkyl group having from 1 to 5 carbon atoms or $R^a$ and $R^b$ together represent an alkylene group which may be substituted, $R^c$ represents a hydrogen atom or an alkyl group having from 1 to 5 carbon atoms, X represents a single bond or an NH group, A represents a phenylene or thienylene group which may be substituted and Y represents a single bond or an oxygen atom;

and substituted at the 3-position by an alkyl group having from 1 to 5 carbon atoms, or a cyclo-alkyl group having from 3 to 7 ring carbon atoms which may include one or more hetero ring atoms. Tetrahydrofuranyl is described as an example of a 3-position substituent: from a list of 14 radicals. The Examples describe only methyl, ethyl and isopropyl groups at the 3-position of the cephalosporin nucleus.

We have now found a particular class of cephalosporins bearing a cyclic ether substituent at the 3-position of the cephalosporin nucleus that possesses prolonged and high levels of antibacterial activity, and shows good absorption both parentally and orally, especially orally.

The present invention provides a compound of formula (I) or a salt thereof:

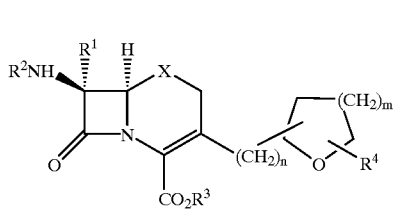

wherein
  $R^1$ is hydrogen, methoxy or formamido;
  $R^2$ is an acyl group, in particular that of an antibacterially active cephalosporin;
  $CO_2R^3$ is a carboxy group or a carboxylate anion, or $R^3$ is a readily removable carboxy protecting group (such as a pharmaceutically acceptable in vivo hydrolysable ester group); $R^4$ represents up to four substituents selected from alkyl, alkenyl, alkynyl, alkoxy, hydroxy, halogen, amino, alkylamino, acylamino, dialkylamino, $CO_2R$, $CONR_2$, $SO_2NR_2$ (where R is hydrogen or $C_{1-6}$ alkyl), aryl and heterocyclyl, which may be the same or different and wherein any $R^4$ alkyl substituent is optionally substituted by any other $R^4$ substituent; X is S, SO, $SO_2$, O or $CH_2$; m is 1 or 2; and n is 0.

The bonding carbon atom of the cyclic ether moiety which links the ring to the cephalosporin nucleus is generally asymmetric. The present invention includes either stereoisomer, as well as mixtures of both isomers.

In compounds of formula (I) wherein $R^1$ is formamido, the formamido group can exist in conformations wherein the hydrogen atoms of the —NH—CHO moiety are cis- or trans-; of these the cis conformation normally predominates.

Since the β-lactam antibiotic compounds of the present invention are intended for use as therapeutic agents in pharmaceutical compositions, it will be readily appreciated that preferred compounds within formula (I) are pharmaceutically acceptable, i.e. are compounds of formula (Ia) or pharmaceutically acceptable salts or pharmaceutically acceptable in vivo hydrolysable esters thereof:

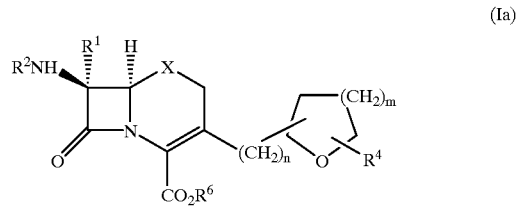

wherein $R^1$, $R^2$, $R^4$, m, n and X are as defined with respect to formula (I) and the group $CO_2R^6$ is $CO_2R^3$ where $CO_2R^3$ is a carboxy group or a carboxylate anion.

Accordingly, the present invention provides a compound of formula (Ia) or a pharmaceutically acceptable salt or in vivo hydrolysable ester thereof, for use as a therapeutic agent, and in particular an in vivo hydrolysable ester thereof for use as an orally administrable therapeutic agent.

The present invention further provides a compound of formula (Ia) or a pharmaceutically acceptable salt or in vivo hydrolysable ester thereof, for use in the treatment of bacterial infections, more particularly an in vivo hydrolysable ester thereof for use in the oral treatment of bacterial infections.

The present invention also includes a method of treating bacterial infections in humans and animals which comprises the administration of a therapeutically effective amount of an antibiotic compound of this invention of the formula (Ia) or a pharmaceutically acceptable in vivo hydrolysable ester thereof, in particular the oral administration of a therapeutically effective amount of an in vivo hydrolysable ester.

In addition, the present invention includes the use of a compound of formula (Ia) or a pharmaceutically acceptable salt or in vivo hydrolysable ester thereof, for the manufacture of a medicament for the treatment of bacterial infections, in particular the use of an in vivo hydrolysable ester for the manufacture of a medicament for the oral treatment of bacterial infections.

Those compounds of the formula (I) wherein $R^3$ is a readily removable carboxy protecting group other than a pharmaceutically acceptable in vivo hydrolysable ester or which are in non-pharmaceutically acceptable salt form are primarily useful as intermediates in the preparation of compounds of the formula (Ia) or a pharmaceutically acceptable salt or pharmaceutically acceptable in vivo hydrolysable ester thereof.

Suitable readily removable carboxy protecting groups for the group $R^3$ include groups forming ester derivatives of the carboxylic acid, including in vivo hydrolysable esters. The derivative is preferably one which may readily be cleaved in vivo.

It will be appreciated that also included within the scope of the invention are salts and carboxy-protected derivatives, including in vivo hydrolysable esters, of any carboxy groups that may be present as optional substituents in compounds of formula (I) or (Ia). Also included within the scope of the invention are acid addition salts of any amino group or substituted amino group that may be present as optional substituents in compounds of formula (I) or (Ia).

Suitable ester-forming carboxyl-protecting groups are those which may be removed under conventional conditions. Such groups for $R^3$ include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofur-2-yl, tetrahydropyran-2-yl, pentachlorophenyl, acetonyl, p-toluenesulphonylethyl, methoxymethyl, a silyl, stannyl or phosphorus-containing group, an oxime radical of formula —N=CHR$^7$ where $R^7$ is aryl or heterocyclic, or an in vivo hydrolysable ester radical such as defined below.

When used herein the term 'aryl' includes phenyl and naphthyl, each optionally substituted with up to five, preferably up to three, groups selected from halogen, mercapto, $C_{1-6}$ alkyl, phenyl, $C_{1-6}$ alkoxy, hydroxy($C_{1-6}$)alkyl, mercapto($C_{1-6}$)alkyl, halo($C_{1-6}$) alkyl, hydroxy, amino, nitro, carboxy, $C_{1-6}$ alkylcarbonyloxy, alkoxycarbonyl, formyl, or $C_{1-6}$ alkylcarbonyl groups.

The terms 'heterocyclyl' and 'heterocyclic' as used herein include aromatic and non-aromatic, single and fused, rings suitably containing up to four hetero-atoms in each ring selected from oxygen, nitrogen and sulphur, which rings may be unsubstituted or substituted by, for example, up to three groups selected from halogen, $(C_{1-6})$alkyl, $(C_{1-6})$alkoxy, halo($C_{1-6}$)alkyl, hydroxy, carboxy, carboxy salts, carboxy esters such as $(C_{1-6})$alkoxycarbonyl, $(C_{1-6})$ alkoxycarbonyl($C_{1-6}$)alkyl, aryl, and oxo groups. Each heterocyclic ring suitably has from 4 to 7, preferably 5 or 6, ring atoms. The term 'heteroaryl' refers to heteroaromatic heterocyclic rings. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

When used herein the terms 'alkyl' alkenyl, alkynyl and 'alkoxy' include straight and branched chain groups containing from 1 to 6 carbon atoms, such as methyl, ethyl, propyl and butyl. A particular alkyl group is methyl.

When used herein the term 'halogen' refers to fluorine, chlorine, bromine and iodine.

A carboxyl group may be regenerated from any of the above esters by usual methods appropriat to the particular $R^3$ group, for example, acid- and base-catalysed hydrolysis, or by enzymically-catalysed hydrolysis, or by hydrogenolysis under conditions wherein the remainder of the molecule is substantially unaffected.

Examples of suitable pharmaceutically acceptable in vivo hydrolysable ester groups include those which break down readily in the human body to leave the parent acid or its salt. Suitable ester groups of this type include those of part formulae (i), (ii), (iii), (iv) and (v):

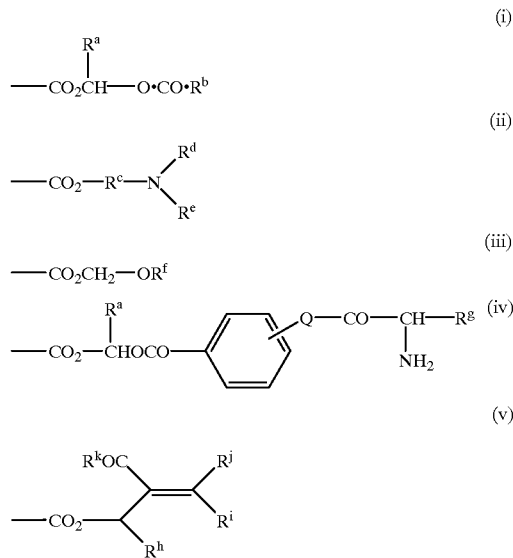

wherein $R^a$ is hydrogen, $C_{1-6}$ alkyl, $C_{3-7}$ cycloalkyl, methyl, or phenyl, $R^b$ is $C_{1-6}$ alkyl, $C_{1-6}$ alkoxy, phenyl, benzyl, $C_{3-7}$ cycloalkyl, $C_{3-7}$ cycloalkyloxy, $C_{1-6}$ alkyl $C_{3-7}$ cycloalkyl, 1-amino $C_{1-6}$ alkyl, or 1-($C_{1-6}$ alkyl) amino $C_{1-6}$ alkyl; or $R^a$ and $R^b$ together form a 1,2-phenylene group optionally substituted by one or two methoxy groups; $R^c$ represents $C_{1-6}$ alkylene optionally substituted with a methyl or ethyl group and $R^d$ and $R^e$ independently represent $C_{1-6}$ alkyl; $R^f$ represents $C_{1-6}$ alkyl; $R^g$ represents hydrogen or phenyl optionally substituted by up to three groups selected from halogen, $C_{1-6}$ alkyl, or $C_{1-6}$ alkoxy; Q is oxygen or NH; $R^h$ is hydrogen or $C_{1-6}$ alkyl; $R_i$ is hydrogen, $C_{1-6}$ alkyl optionally substituted by halogen, $C_{2-6}$ alkenyl, $C_{1-6}$ alkoxycarbonyl, aryl or heteroaryl; or $R^h$ and $R^i$ together form $C_{1-6}$ alkylene; $R^j$ represents hydrogen, $C_{1-6}$ alkyl or $C_{1-6}$ alkoxycarbonyl; and $R^k$ represents $C_{1-8}$ alkyl, $C_{1-8}$ alkoxy, $C_{1-6}$ alkoxy($C_{1-6}$)alkoxy or aryl.

Examples of suitable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl, α-ethoxycarbonyloxyethyl and propoxycarbonyloxyethyl; dialkylaminoalkyl especially di-loweralkylamino alkyl groups such as dimethylaminomethyl, dimethylaminoethyl, diethylaminomethyl or diethylaminoethyl; 2-(alkoxycarbonyl)-2-alkenyl groups such as 2-(isobutoxycarbonyl)pent-2-enyl and 2-(ethoxycarbonyl) but-2-enyl; lactone groups such as phthalidyl and dimethoxyphthalidyl; and esters linked to a second β-lactam antibiotic or to a β-lactamase inhibitor.

A preferred in vivo hydrolysable ester group is the pivaloyloxymethyl ester.

A further suitable pharmaceutically acceptable in vivo hydrolysable ester group is that of the formula:

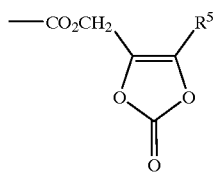

wherein $R^5$ is hydrogen, $C_{1-6}$ alkyl or phenyl.

Suitable pharmaceutically acceptable salts of the carboxy group of the compound of formula (I) include metal salts, eg aluminium, alkali metal salts such as sodium or potassium, especially sodium, alkaline earth metal salts such as calcium or magnesium, and ammonium or substituted ammonium salts, for example those with lower alkylamines such as triethylamine, hydroxy-lower alkylamines such as 2-hydroxyethylamine, bis-(2-hydroxyethyl) amine or tris-(2-hydroxyethyl)-amine, cycloalkylamines such as dicyclohexylamine, or with procaine, dibenzylamine, N,N-dibenzylethylene-diamine, 1-ephenamine, N-methylmorpholine, N-ethylpiperidine, N-benzyl-β-phenethylamine, dehydroabietylamine, N,N'-bisdehydroabietylamine, ethylenediamine, or bases of the pyridine type such as pyridine, collidine or quinoline, or other amines which have been used to form salts with known penicillins and cephalosporins. Other useful salts include the lithium salt and silver salt. Salts within compounds of formula (I), may be prepared by salt exchange in conventional manner.

In compounds of formula (I) or (Ia), the group X may be sulphur or an oxidised sulphur atom, i.e. a sulphoxide (SO) or sulphone ($SO_2$) group. When X is a sulphoxide group it will be understood that α- and β-isomers may exist; both such isomers are encompassed within the scope of the present invention.

Examples of X include S, SO, $SO_2$ and $CH_2$. Preferably X is sulphur or $CH_2$.

Advantageously, $R^1$ is hydrogen.

Suitably, the cyclic ether at the 3-position of the cephalosporin nucleus is unsubstituted or substituted by up to three substituents, $R^4$, selected from $C_{1-6}$ alkyl, for example methyl, $C_{1-6}$ alkoxy, for example methoxy, $C_{1-6}$ alkoxycarbonyl for example methoxycarbonyl, $C_{1-6}$ alkoxy $C_{1-6}$ alkyl, for example methoxymethyl, and $C_{1-6}$ alkanoyloxy $C_{1-6}$ alkyl, for example acetoxymethyl. Preferably the cyclic ether at the 3-position of the cephalosporin nucleus is unsubstituted.

Preferably m is 1.

Preferably the cyclic ether is bonded to the cephalosporin nucleus at a ring carbon adjacent to the oxygen heteroatom.

Suitable acyl groups $R^2$ include those of formulae (a)–(f):

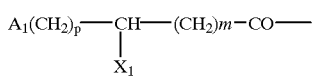
(a)

(b)

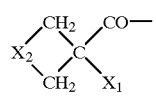
(c)

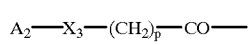
(d)

-continued

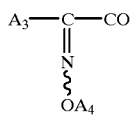
(e)

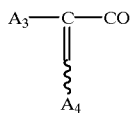
(f)

wherein p is 0, 1 or 2; m is 0, 1 or 2; $A_1$ is $C_{1-6}$ alkyl, substituted $C_{1-6}$ alkyl, $C_{3-6}$ cycloalkyl, cyclohexenyl, cyclohexadienyl, an aromatic (including heteroaromatic) group, such as phenyl, substituted phenyl, thienyl, pyridyl, or an optionally substituted thiazolyl group, a $C_{1-6}$ akylthio group or $C_{1-6}$ alkyloxy; $X_1$ is a hydrogen or halogen atom, a carboxylic acid, carboxylic ester, sulphonic acid, azido, tetrazolyl, hydroxy, acyloxy, amino, ureido, acylamino, heterocyclylamino, guanidino or acylureido group; $A_2$ is an aromatic group, for example a phenyl, 2,6-dimethoxyphenyl,2-alkoxy-1-naphthyl, 3-arylisoxazolyl, or a 3-aryl-5-methylisoxazolyl group, such as 3-(2-chloro-6-fluorophenyl)-5-methylisoxazol-4-yl; a substituted alkyl group; or a substituted dithietane; $X_2$ is a —$CH_2OCH_2$—, —$CH_2SCH_2$— or alkylene group; $X_3$ is an oxygen or sulphur atom; $A_3$ is an aryl or heteroaryl group such as phenyl, substituted phenyl, furyl, aminothiazolyl or aminothiadiazolyl in which the amino group is optionally protected; and $A_4$ is hydrogen, $C_{1-6}$alkyl, $C_{3-8}$ cycloalkyl, $C_{3-8}$ cycloalkyl ($C_{1-6}$)alkyl, $C_{1-6}$ alkoxycarbonyl($C_{1-6}$) alkyl, $C_{2-6}$ alkenyl, carboxy($C_{1-6}$)alkyl, $C_{2-6}$ alkynyl, aryl or $C_{1-6}$alkyl substituted by up to three aryl groups.

The term 'heteroaryl' as used herein means a heteroaromatic heterocyclic ring or ring system, suitably having 5 or 6 ring atoms in each ring.

Suitably when $R^2$ is a group (a), $A_1$ is $C_{1-6}$ alkyl, $C_{3-6}$ cycloalkyl, cyclohexenyl, cyclohexadienyl, phenyl, substituted phenyl such as hydroxyphenyl, thienyl or pyridyl; and $X_1$ is a hydrogen or halogen atom, or a carboxy, carboxylic ester, azido, tetrazolyl, hydroxy, acyloxy, optionally protected amino, ureido, guanidino or acylureido group.

Suitably when $R^2$ is a group of formula (d), $A_2$ is phenyl, $X_3$ is oxygen and p is 0.

Alternatively when $R^2$ is a group of formula (e) or (f) suitable values for the group $A_3$ include those commonly found in antibacterially active cephalosporins containing a hydroxyimino, substituted hydroxyimino or vinyl group in the side chain attached to position 7 of the cephalosporin nucleus, for example phenyl, thien-2-yl, thien-3-yl, fur-2-yl, fur-3-yl, pyrid-2-yl, pyrid-3-yl pyrid-4-yl, 5-amino-1,2,4-thiadiazol-3-yl and 2-aminothiazol-4-yl in each of which the amino group is optionally protected.

Preferred groups for $A_3$ include phenyl, 2-aminothiazol-4-yl, fur-2-yl, thien-2-yl, 2-(2-chloroacetamido)thiazol-4-yl, 2-tritylamino-thiazol-4-yl, 5-amino-1,2,4-thiadiazol-3-yl and 4-aminopyrimid-2-yl.

In compounds of formula (Ia), a particularly preferred group for $A_3$ is 2-aminothiazol-4-yl.

Suitable values for the group $A_4$ include hydrogen, methyl, ethyl, cyclopropylmethyl, triphenylmethyl (trityl), cyclobutyl, cyclopentyl, cyclohexyl, cycloheptyl, cyclooctyl, phenyl, carboxymethyl, carboxypropyl and t-butoxycarbonylmethyl.

Preferred values for $A_4$ in compounds of formula (Ia) include methyl and hydrogen.

It will be appreciated that compounds of the invention wherein $R^2$ is a group of formula (e) (or (f)) can exist as syn and anti (or E and Z) isomers or mixtures thereof. Both isomers are encompassed within the scope of this invention.

Preferably the compounds of the invention wherein $R^2$ is a group of formula (e) have the syn configuration (i.e. have the group $OA_4$ syn to the amide linkage) or are enriched in that isomer.

Similarly, when $R^2$ is a group of formula (f), the group $A_4$ is preferably cis to the amide linkage, i.e. when group (f) is 2-amino-thiazol-4-yl, the Z-configuration is preferred.

Certain compounds of the invention include an amino group which may be protected. Suitable amino protecting groups are those well known in the art which may be removed under conventional conditions without disruption of the remainder of the molecule.

Examples of amino protecting groups include $C_{1-6}$ alkanoyl; benzoyl; benzyl optionally substituted in the phenyl ring by one or two substituents selected from $C_{1-4}$ alkyl, $C_{1-4}$ alkoxy, trifluoromethyl, halogen, or nitro; $C_{1-4}$ alkoxycarbonyl; benzyloxycarbonyl or trityl substituted as for benzyl above; allyloxycarbonyl, trichloroethoxycarbonyl or chloroacetyl.

Some of the compounds of this invention may be crystallised or recrystallised from solvents such as organic solvents. In such cases solvates may be formed. This invention includes within its scope stoichiometric solvates including hydrates as well as compounds containing variable amounts of water that may be produced by processes such as lyophilisation.

Since the antibiotic compounds of the invention are intended for use in pharmaceutical compositions it will readily be understood that they are each provided in substantially pure form, for example at least 60% pure, more suitably at least 75% pure and preferably at least 85%, especially at least 95% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 49% of a compound of the formula (I) or salt thereof.

Specific compounds within this invention of formula (Ia) include the following pharmaceutically acceptable carboxylic acids, salts and in-vivo hydrolysable esters:

sodium (6R,7R)-7-[2-(2-aminothiazol-4-yl)-2-(Z)-methoxyiminoacetamido]-3-[(RS)-tetrahydrofuran-2-yl]-ceph-3-em-4-carboxylate;

pivaloyloxymethyl (6R,7R)-7-[2-(2-aminothiazol-4-yl)-2-(Z)-methoxyiminoacetamido]-3-[(RS)-tetrahydrofuran-2-yl]ceph-3-em-4-carboxylate;

sodium (6R,7R)-7-[2-(2-aminothiazol-4-yl)-2-(Z)-methoxyiminoacetamido]-3-[(RS)-tetrahydropyran-2-yl]ceph-3-em-4-carboxylace;

pivaloylcxymethyl (6R,7R)-7-[2-(2-aminothiazol-4-yl)-2-(Z)-methoxyiminoacetamido]-3-[(RS)-tetrahydropyran-2-yl]ceph-3-em-4-carboxylate;

(6R,7R)-7-[2-(2-aminothiazol-4-yl)-2-(Z)-hydroxyiminoacetamido]-3-[(RS)-tetrahydrofuran-2-yl]ceph-3-em-4-carboxylic acid;

sodium (6R,7R)-7-[2-(2-aminothiazol-4-yl)-2-(Z)-methoxyiminoacetamido]-3-[(S)-tetrahydrofuran-2-yl]ceph-3-em-4-carboxylate;

pivaloyloxymethyl (6R,7R)-7-[2-(2-aminothiazol-4-yl)-2-(Z)-methoxyiminoacetamido]-3-[(S)-tetrahydrofuran-2-yl]ceph-3-em-4-carboxylate;

sodium (6R,7R)-7-[2-(2-aminothiazol-4-yl)-2-(Z)-methoxyiminoacetamido]-3-[(R)-tetrahydrofuran-2-yl]ceph-3-em-4-carboxylate;

pivaloyloxymethyl (6R,7R)-7-[2-(2-aminothiazol-4-yl)-2-(Z)-methoxyiminoacetamido]-3-[(R)-tetrahydrofuran-2-yl]ceph-3-em-4-carboxylate;

sodium (6R,7R)-7-[2-(2-aminothiazol-4-yl)-2-(Z)-methoxyiminoacetamido]-3-[(RS)-tetrahydrofuran-3-yl]ceph-3-em-4-carboxylate;

acetoxymethyl (6R,7R)-7-[2-(2-aminothiazol-4-yl)-2-(Z)-methoxyiminoacetamido]-3-[(S)-tetrahydrofuran-2-yl]ceph-3-em-4-carboxylate;

sodium (6R,7R)-7-[2-(2-aminothiazol-4-yl)-2-(Z)-methoxyiminoacetamido]-3-(5-methoxymethyltetrahydrofuran-2-yl)ceph-3-em-4-carboxylate;

sodium (6R,7R)-7-[2-(2-aminothiazol-4-yl)-(Z)-pent-2-enamido]-3-[(S)-tetrahydrofuran-2-yl]ceph-3-em-4-carboxylaoe;

sodium (6R,7R)-7-[2-(2-aminothiadiazol-4-yl)-2-(Z)-methoxyiminoacetamido]-3-[(S)-tetrahydrofuran-2-yl]ceph-3-em-4-carboxylate;

(RS)-1-acetoxyethyl (6R,7R)-7-[2-(2-aminothiazol-4-yl)-2-(Z)-methoxyiminoacetamido]-3-[(S)-tetrahydrofuran-2-yl]ceph-3-em-4-carboxylate;

(6R,7R)-7-[2-(2-aminothiazol-4-yl)-2-(Z)-carboxymethoxyiminoacetamido]-3-[(RS)-tetrahydrofuran-2-yl]-ceph-3-em-4-carboxylic acid, disodium salt;

sodium (6R,7R)-7-[(R)-2-amino-2-(4-hydroxyphenyl)acetamido]-3-[(S)-tetrahydrofuran-2-yl]ceph-3-em-4-carboxylate;

sodium (1S,6R,7R)-7-[2-(2-aminothiazol-4-yl)-2-(Z)-methoxyiminoacetamido]-3-[(S)-tetrahydrofuran-2-yl]ceph-3-em-4-carboxylate-1-oxide;

sodium 7-[2-(2-aminothiazol-4-yl)-2-(Z)-methoxyiminoacetamido]-3-(tetrahydrofuran-2-yl)-1-carba-1-dethiaceph-3-em-4-carboxylate;

sodium (6R,7R)-7-[2-(2-aminothiazol-4-yl)-2-(Z)-methoxyiminoacetamido]-3-[(S)-tetrahydrofuran-2-yl]ceph-3-em-4-carboxylate-1,1-dioxide;

(RS)-1-(propan-2-yl)oxycarbonyloxyethyl (6R,7R)-7-[2-(2-aminothiazol-4-yl)-2-(Z)-methoxyiminoacetamido]-3-[(S)-tetrahydrofuran-2-yl]ceph-3-em-4-carboxylate;

sodium (6R,7R)-7-[2-(2-aminothiazol-4-yl)-2-(Z)-methoxyiminoacetamido]-3-[(5R,5R)-5-methyltetrahydrofuran-2-yl)-ceph-3-em-4-carboxylate;

sodium (6R,7R)-7-[2-(furan-2-yl)-2-(Z)-methoxyiminoacetamido]-3-[(S)-tetrahydrofuran-2-yl]ceph-3-em-4-carboxylate sodium (6R,7R)-7-[2-(2-aminothiazol-4-yl)-2-(Z)-methoxyiminoacetamido]-3-[(S)-5,5-dimethyltetrahydrofuran-2-yl]-ceph-3-em-4-carboxylate;

sodium (6R,7R)-7-[2-(2-aminothiazol-4-yl)-2-(Z)-methoxyiminoacetamido]-3-(5-methoxycarbonyltetrahydrofuran-2-yl)-ceph-3-em-4-carboxylate;

sodium (6R,7R)-7-[2-(2-aminothiazol-4-yl)-2-(Z)-methoxyiminoacetamido]-3-[-methyltetrahydrofuran-2-yl]ceph-3-em-4-carboxylate; and 2-ethoxycarbonyl-(Z)-but-2-enyl (6R,7R)-7-[2-(2-aminothiazol-4-yl)-2-(Z)-methoxyiminoacetomido]-3-[(S)-tetrahydrofuran-2-yl]ceph-3-em-4-carboxylate.

The present invention further provides a process for the preparation of a compound of formula (I), which process comprises treating a compound of formula (II) or a salt thereof:

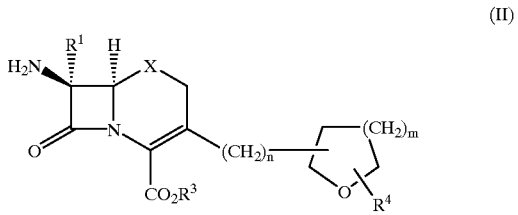

(II)

wherein $R^1$, $CO_2R^3$, $R^4$, m, n and X are as hereinbefore defined, wherein any reactive groups may be protected, and wherein the amino group is optionally substituted with a group which permits acylation to take place; with an N-acylating derivative of an acid of formula (III):

$R^2OH$ (III)

wherein $R^2$ is as defined with respect to formula (I) and wherein any reactive groups may be protected; and thereafter, if necessary or desired, carrying out one or more of the following steps:

i) removing any protecting groups;
ii) converting the group $CO_2R^3$ into a different group $CO_2R^3$;
iii) converting the group $R^2$ into a different group $R^2$;
iv) converting the group X into a different group X;
v) converting the product into a salt.

Acids of formula (III) may be prepared by methods known in the art, or methods analogous to such processes. Suitable processes include those described, for example, in UK Patent 2 107 307 B, UK Patent Specification No. 1,536,281, and U.K. Patent Specification No. 1,508,064.

Suitable groups which permit acylation to take place and which are optionally present on the amino group of the starting material of the formula (II) include N-silyl, N-stannyl and N-phosphorus groups, for example trialkylsilyl groups such as trimethylsilyl, trialkyltin groups such as tri-n-butyltin, groups of formula $—P.R^{20}R^{21}$ wherein $R^{20}$ is an alkyl, haloalkyl, aryl, aralkyl, alkoxy, haloalkyl, aryl, aralkyl, alkoxy, haloalkoxy, aryloxy, aralkyloxy or dialkylamino group, $R^{21}$ is the same as $R^{20}$ or is halogen or $R^{20}$ and $R^{21}$ together form a ring; suitable such phosphorus groups being $—P(OC_2H_5)_2$, $—P(C_2H_5)_2$,

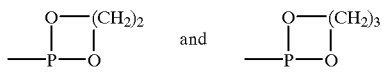

and

A group which may optionally be introduced onto the amino group in the compound of formula (II) is trimethylsilyl.

Advantageously the silylation reaction may be carried out in situ, prior to the acylation reaction, with a silylating agent that does not require concomitant addition of base. Suitable silylating agents include, for example, N-(trimethylsilyl)-acetamide, N,O-bis-(trimethylsilyl)acetamide, N,O-bis(trimethylsilyl)-trifluoroacetamide, N-methyl-N-trimethylsilylacetamide, N-methyl-N-trimethylsilyl-trifluoroacetamide, N,N'-bis(trimethylsilyl)urea, and N,O-bis(trimethylsilyl)carbamate. A preferred silylating agent is N,O-bis(trimethylsilyl)acetamide. The silylation reaction may suitably be carried out in an inert, anhydrous organic solvent such as dichloromethane at room temperature or at an elevated temperature, for example 30–60° C., preferably 40–50° C.

The above process may optionally be carried out in the presence of a small quantity, for example 0.1 equivalents, of a silyl halide, for example a tri($C_{1-6}$)alkylsilyl halide, especially trimethylsilyl chloride.

A reactive N-acylating derivative of the acid (III) is employed in the above process. The choice of reactive derivative will of course be influenced by the chemical nature of the substituents of the acid.

Suitable N-acylating derivatives include an acid halide, preferably the acid chloride or bromide or alternatively a symmetrical or mixed anhydride. The acylation may be effected in the presence of an acid binding agent for example, tertiary amine (such as pyridine or dimethylaniline), molecular sieves, an inorganic base (such as calcium carbonate or sodium bicarbonate) or an oxirane, which binds hydrogen halide liberated in the acylation reaction. The oxirane is preferably a ($C_{1-6}$)-1,2-alkylene oxide—such as ethylene oxide or propylene oxide. The acylation reaction using an acid halide may be carried out at a temperature in the range −50° C. to +50° C., preferably −20° C. to +20° C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate. The acylation with acid halide or anhydride is suitably carried out in the presence of a basic catalyst such as pyridine or 2,6-lutidine.

Acid halides may be prepared by reacting the acid (III) or a salt or a reactive derivative thereof with a halogenating (eg chlorinating or brominating) agent such as phosphorus pentachloride, thionyl chloride, oxalyl chloride or phosgene.

Suitable mixed anhydrides are anhydrides with, for example, carbonic acid monoesters, trimethyl acetic acid, thioacetic acid, diphenylacetic acid, benzoic acid, phosphorus acids (such as phosphoric, phosphorous, and phosphinic acids) or aromatic or aliphatic sulphonic acids (such as p-toluenesulphonic acid or methanesulphonic acid).

Alternative N-acylating derivatives of acid (III) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol, N-hydroxy succinimide, N-hydroxybenzotriazole, or 8-hydroxyquinoline; or amides such as N-acylsaccharins, N-acylthiazolidin-2-thione or N-acylphthalimides; or an alkylidene iminoester prepared by reaction of the acid (III) with an oxime.

Other reactive N-acylating derivatives of the acid (III) include the reactive intermediates formed by reaction in situ with a condensing agent such as a carbodiimide, for example, N,N'-diethyl-, dipropyl- or diisopropylcarbodiimide, N,N'-di-cyclohexyl-carbodiimide, or N-ethyl-N'-(3-(dimethylamino)propyl]-carbodiimide; a suitable carbonyl compound, for example, N,N'-carbonyldiimidazole or N,N'-carbonyldi-triazole; an isoxazolinium salt, for example, N-ethyl-5-phenylisoxazolinium-3-sulphonate or N-t-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3$—$C_6H_6$) or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

A further method of forming the N-acylating derivative of the acid of formula (III) is to treat the acid of formula (III) with a solution or suspension preformed by addition of a carbonyl halide, preferably oxalyl chloride, or a phosphoryl halide such as phosphorus oxychloride, to a halogenated hydrocarbon solvent, preferably dichloromethane, containing a lower acyl tertiary amide, preferably N,N-dimethylformamide. The N-acylating derivative of the acid of formula (III) so derived may then be caused to react with a compound of formula (II). The acylation reaction may conveniently be carried out at −40° to +30° C., if desired in the presence of an acid binding agent such as pyridine. A catalyst such as 4-dimethylaminopyridine may optionally also be added. A preferred solvent for the above acylation reaction is dichloromethane.

The optional reduction step, the optional conversion of $R^2$ to a different $R^2$, $CO_2R^3$ to a different $CO_2R^3$ and X to a different X, and the optional formation of a salt, may be carried out using methods well known in the art of cephalosporin and penicillin chemistry.

For example, when the group X is S, SO, or $SO_2$, the group X may be converted into a different group X by methods of oxidation or reduction well known in the art of cephalosporin and penicillin synthesis, as described, for example, in European Patent Application Publication No. 0 114 752. For example, sulphoxides (in which X is SO) may be prepared from the corresponding sulphide (in which X is S) by oxidation with a suitable oxidising agent, for example an organic peracid such as m-chloroperbenzoic acid.

A reduction step is generally effected by processes well known in the art of β-lactam chemistry, for example using phosphorus trichloride in dimethylformamide.

In the process described hereinabove, and in the process described hereinbelow, it may be necessary to remove protecting groups. Deprotection may be carried out by any convenient method known in the art such that unwanted side reactions are minimised. Separation of unwanted by-products may be carried out using standard methods.

In a further process of the invention, compounds of formula (I) may be prepared by cyclising a compound of formula (IV):

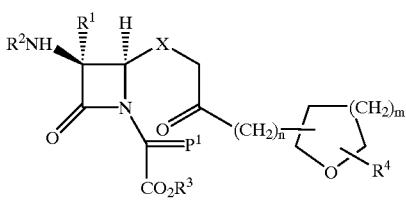

(IV)

wherein X, $R^1$, $R^2$, $R^4$, m, n and $CO_2R^3$ are as hereinbefore defined and P' is a phosphorus residue; and thereafter if necessary or desired, carrying out one or more of the following steps:
i) removing any protecting groups;
ii) converting the group $CO_2R^3$ into a different group $CO_2R^3$;
iii) converting the group $R^2$ into a different group $R^2$;
iv) converting the group X into a different group X;
v) converting the product into a salt.

The cyclisation reaction is an intramolecular Wittig-type reaction and is typically carried out by heating the compound of formula (IV) in an organic solvent system, for example in toluene, optionally in the presence of a suitable acid such as benzoic acid.

The phosphorus residue, P' is typically a trialkylphosphoranylidene residue, for example a $C_{1-6}$ trialkylphosphoranylidene residue such as tri-n-butylphosphoranylidene, or a triarylphosphoranylidene residue such as triphenylphosphoranylidene.

Where $R^2$ in a compound of formula (I) is required to be different from the group $R^2$ in the compound of formula (IV), the conversion may be effected via the intermediacy of a compound of formula (II) which has an amino group at the 7-position of the cephalosporin nucleus.

An $R^2$ side-chain may be removed by the Delft procedure commonly used in β-lactam chemistry. Suitable reaction conditions include treatment with phosphorus pentachloride and N-methylmorpholine at reduced temperature.

Compounds of formula (II) are novel compounds and as such form part of the invention.

A compound of formula (IV) may be prepared from a compound of formula (V):

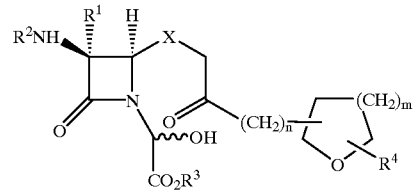

(V)

wherein X, $R^1$, $R^2$, $R^4$, m, n and $CO_2R^3$ are as hereinbefore defined, by reaction with a halogenating agent, suitably a chlorinating agent such as thionyl chloride, which reaction displaces the formula (V) hydroxyl group by halogen, suitably chloride, and is typically carried out at reduced temperature in an inert solvent, for example in tetrahydrofuran, in the presence of a base, typically a pyridine derivative such as 2,6-lutidine. Formation of the phosphorane may be effected by treatment of the halo-intermediate with an appropriate phosphine derivative, for example tri-n-butylphosphine or triphenylphosphine, suitably at ambient temperature in an inert solvent such as dioxan.

A compound of formula (V) may be prepared by reaction of a compound of formula (VI):

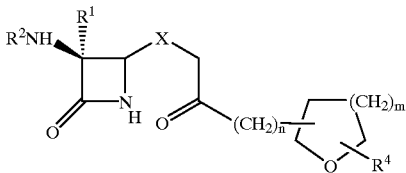

(VI)

wherein X, $R^1$, $R^2$, $R^4$, m and n are as hereinbefore defined with an ester of glyoxylic acid ($OCHCO_2R^3$) in the presence of triethylamine.

In a typical preparation of a compound of formula (VI) in which X is sulphur, a compound of formula (VII):

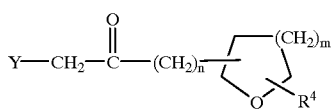
(VII)

wherein Y is a leaving group and $R^4$, m and n are as hereinbefore defined is reacted with a compound of formula (VIII):

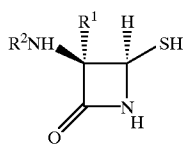
(VIII)

wherein $R^1$ and $R^2$ are as hereinbefore defined.

Suitably, a leaving group Y is halogen, for example chloro. The reaction may be carried out at ambient temperature in an inert solvent, for example acetone or dimethylformamide, in the presence for a base, for example potassium carbonate.

A compound of formula (V) may also be prepared by reaction of a compound of formula (IX):

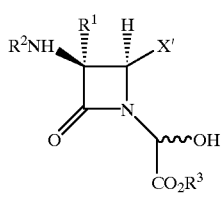
(IX)

wherein $R^1$, $R^2$ and $CO_2R^3$ are as hereinbefore defined and X' is an X-group precursor, with a compound of formula (VII) as hereinbefore defined.

In a typical preparation of a compound of formula (V) in which X is sulphur, a Y leaving group in a compound of formula (VII), suitably a halogen such as chloro or bromo, is displaced by an X' mercapto group in a compound of formula (IX). The reaction may be carried out at ambient temperature in an inert solvent, for example acetone, with the addition of base, for example potassium carbonate, before work-up.

Azetidin-2-one compounds of formulae (VIII) and (IX) may be prepared according to known methods in heterocyclic synthetic chemistry and particularly by known methods in the art of β-lactam chemistry. For example a compound of formula (VIII) may be prepared according to the method of Osborne N. F. et al., J. Chem. Soc., Perkin Trans. I, 146, 1980.

A compound of formula (IX) in which X' is a mercapto group may be prepared by ring opening of a 4-thia-2,6-diazabicyclo [3.2.0]-hept-2-ene-7-one derivative according to the method of Masayuki Narisada et al., Tetrahedron Lett., 1755 (1978).

Compounds of formula (VII) are known compounds or may be prepared by standard methodology. For example, the compounds of formula (VII) in which Y is chloro or bromo may be prepared from the corresponding carboxylic acid (Y=COOH) via formation of the acid chloride followed by treatment with diazomethane and reaction of the resulting diazo compound with hydrogen chloride or hydrogen bromide.

In a further process of the invention, compounds of formula (I) may be prepared directly by organo-cuprate displacement of a leaving group at the 3-position of a compound of formula (X):

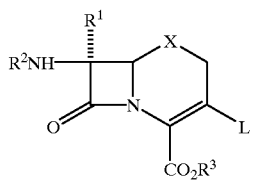
(X)

wherein $R^1$, $R^2$, $CO_2R^3$ and X are as hereinbefore defined and L is a leaving group, suitably a mesylate, triflate or fluorosulphonate leaving group, by reaction with a compound of formula (XI):

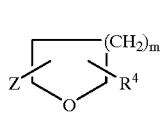
(XI)

wherein Z is an organo-cuprate group and $R^4$ and m are as hereinbefore defined.

A compound with a 3-position leaving group, L, in which X is sulphur may be prepared by the procedure of Farina V. et al., J. Org. Chem., 54, 4962, (1989).

A compound with a 3-position leaving group, L, in which X is $CH_2$ may be prepared by a transition metal-catalysed carbenoid insertion reaction of a diazodicarbonyl compound of formula (XII):

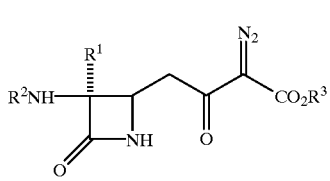
(XII)

wherein $R^1$, $R^2$ and $CO_2R^3$ are as hereinbefore defined, followed by reaction with an appropriate anhydride, for example triflic anhydride. Compounds of formula (XII) may be prepared by the procedure of Bodurow C. and Carr M. A.; Tetrahedron Lett., 30 4801, (1989).

It should be noted that in processes of this invention $\Delta^2$-cephems may function as intermediates, in the synthetic sequences. Subsequent isomerisation steps by methods well known in cephalosporin chemistry will provide the $\Delta^3$-cephems of the invention.

The present invention also provides a pharmaceutical composition which comprises a compound of formula (Ia) or a pharmaceutically acceptable salt or in vivo hydrolysable ester thereof and a pharmaceutically acceptable carrier. The compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral, especially oral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit aose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No unacceptable toxicological effects are expected when a compound of formula (Ia) or a pharmaceutically acceptable salt or in vivo hydrolysable ester thereof is administered in the above-mentioned dosage range.

The compound of formula (Ia) may be the sole therapeutic agent in the compositions of the invention or a combination with other antibiotics or with a β-lactamase inhibitor may be employed.

Advantageously, the compositions also comprise a compound of formula (XIII) or a pharmaceutically acceptable salt or ester thereof:

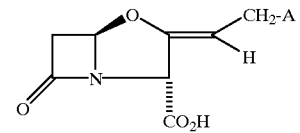

(XIII)

wherein

A is hydroxyl, substitute, hydroxyl, thiol, substituted thiol, amino, mono- or di-hydrocarbyl-substituted amino, or mono- or di-acylamino; an optionally substituted triazolyl group; or an optionally substituted tetrazolyl group as described in EP-A-0 053 893.

A further advantageous composition comprises a compound of formula (Ia) or a pharmaceutically acceptable salt or in vivo hydrolysable ester thereof together with a compound of formula (XIV) or a pharmaceutically acceptable salt or in vivo hydrolysable ester thereof:

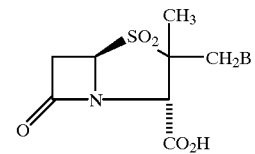

(XIV)

wherein

B represents hydrogen, halogen or a group of formula:

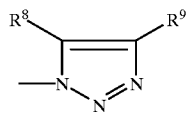

in which $R^8$ and $R^9$ are the same or different and each represents hydrogen, $C_{1-6}$ alkoxycarbonyl or carboxy, or a pharmaceutically acceptable salt thereof.

Further suitable β-lactamase inhibitors include 6-alkylidene penems of formula (XV):

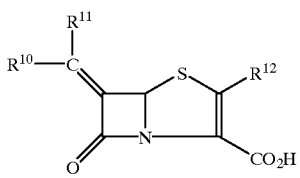

(XV)

or a pharmaceutically acceptable salt or in vivo hydrolysable ester thereof, wherein $R^{10}$ and $R^{11}$ are the same or different and each represents hydrogen, or a $C_{1-10}$-hydrocarbon or heterocyclic group optionally substituted with a functional group; and $R^{12}$ represents hydrogen or a group of formula $R^{13}$ or —$SR^{13}$ where $R^{13}$ is an optionally substituted $C_{1-10}$ hydrocarbon or heterocyclic group, as described in EP-A-0 041 768.

Further suitable β-lactamase inhibitors include 6β-bromopenicillanic acid and pharmaceutically acceptable salts and in vivo hydrolysable esters thereof and 6β-iodopenicillanic acid and pharmaceutically acceptable salts and in vivo hydrolysable esters thereof described in, for example, EP-A-0 410 768 and EP-A-0 154 132 (both Beecham Group).

Such compositions of this invention which include a β-lactamase inhibitory amount of a β-lactamase inhibitor are formulated in a conventional manner using techniques and procedures per se known in the art.

The antibiotic compounds of the present invention are active against a wide range of organisms including both Gram-negative organisms such as E.coli and Gram-positive organisms such as S.aureus.

The following Examples illustrate the preparation of compounds of the invention and intermediates thereto. The following biological data illustrate the activity of compounds of the invention in the form of MIC values (minimum inhibitory concentration) against a sample E.coli organism (NCTC 10418) and a sample S.aureus organism (S.aureus Oxford).

EXAMPLE 1

Sodium (6R,7R)-7-[2-(2-Aminothiazol-4-yl)-2-(Z)-methoxyiminoacetamido]-3-[(RS)-tetrahydrofuran-2-yl]ceph-3-em-4-carboxylate (a) (RS)-2-Chloroacetyltetrahydrofuran Oxalyl chloride (5.2 ml, 60 mmol) and DMF (1 drop) were added to (RS)-2-tetrahydrofuroic acid (W. E. Kaufmann and R. Adams, J.Amer.Chem.Soc., 1923, 45, 3029) (4.64 g, 40 mmol) in dichloromethane (25 ml). The mixture was stirred 1 h, evaporated in vacuo, dichloromethane added and reevaporated to give 2-tetrahydrofuroyl chloride, $v_{max}$ ($CH_2Cl_2$) 1795 cm$^{-1}$. 2-Tetrahydrofuroyl chloride in ether (25 ml) and dichloromethane (10 ml) was added dropwise to an ice bath cooled solution of diazomethane (ca 80 mmol) in ether (150 ml). The reaction mixture was stirred 0.25 h then a stream of hydrogen chloride gas passed into the solution for ca 2 minutes then stirred a further 0.25 h, washed with saturated brine, dried, concentrated and flash chromatographed on silica gel eluting with 5, 7.5 and 10% ethyl acetate in hexane to provide the title compound (2.46 g, 41%); (Found: M$^+$, 148.0279. $C_6H_9ClO_2$ requires M, 148.0291); $v_{max}$($CH_2Cl_2$) 1739, 1395, 1071 and 936 cm$^{-1}$; $δ_H$ (CDCl$_3$, 250 MHz) 1.8–2.4 (4H, m) and 3.9–4.6 (5H, m).

(b) (3R,4R)-3-Phenoxyacetamido-4-[(RS)-tetrahydrofuran-2-ylcarbonylmethylthio]azetidin-2-one (RS)-2-Chloroacetyltetrahydrofuran (2.46 g, 16.5 mmol), (3R,4R)-4-mercapto-3-phenoxyacetamidoazetidin-2-one (4.157 g, 16.5 mmol) and potassium carbonate (2.227 g, 16.5 mmol) in DMF (10 ml) were stirred for 2 h, diluted with ethyl acetate, washed twice with water and with brine, dried concentrated and flash chromatographed eluting with 40,30, 20,10 and 0% hexane in ethyl acetate to give the title compound as a foam (3.547 g, 59%); $v_{max}$($CH_2Cl_2$) 3405, 1785, 1693, 1520, 1496 and 1240 cm$^{-1}$; δ(CDCl$_{3, 250}$ MHz) 1.9–2.3 (4H, m), 3.42 and 3.62, 3.46 and 3.56 (together 2H, 2 ABq, J15.8 Hz, 15.4 Hz), 3.85–4.0 (2H, m), 4.4–4.5 (1H, m), 4.58 (2H, s), 5.01, 5.04 (together 1H, 2d, J4.7 Hz), 5.59 (1H, dd, J 8.8, 4.5 Hz) 6.62, 6.68 (together 1H, 2s), 6.9–7.4 (5H, m) and 7.45, 7.47 (together 1H, 2d, J8.8 Hz). [Mass spectrum: M$^+$ (364)].

(c) t-Butyl (RS)-2-Hydroxy-2-[(3R,4R)-3-phenoxyacetamido-4-[(RS)-tetrahydrofuran-2-ylcarbonylmethylthio]azetidin-2-on-1-yl]acetate 0.5M t-Butyl glyoxylate in 1,2-dichloroethane (20 ml) and triethylamine (140 μl, 1 mmol) were added to (3R,4R)-phenoxyacetamido-4-[(RS)-tetrahydrofuran-2-ylcarbonylmethylthio]azetidin-2-one (3.547 g, 9.7 mmol) in 1,2-dichloroethane (10 ml). The mixture was stirred 1 h, concentrated in vacuo and flash chromatographed eluting with 50, 60, 70% ethyl acetate in hexane (3.663 g, 76%); $v_{max}$($CH_2Cl_2$) 3471, 3407, 1782, 1736, 1692, 1521, 1290, 1154 and 1083 cm$^{-1}$; $δ_H$ (CDCl$_3$, 250 MHz) 1.53 (9H, s), 1.85–2.25 (4H, m), 3.4–3.7 (2H, m), 3.8–4.0 (2H, m), 4.3–4.45 (1H, m), 4.57 (2H, s), 5.07, 5.09, 5.16, 5.18 (together 1H, 4d, J4.8 Hz), 5.25–5.45 (1H, m), 5.48, 5.58 (together 1H, 2dd, J4.8, 8.8 Hz), 6.9–7.4 (5H, m) and 7.41, 7.56 (together 1H, 2d, J8.7 Hz). [Mass spectrum: +ve ion (thioglycerol) MH$^+$ (495)].

(d) t-Butyl 2-[(3R,4R)-3-Phenoxyacetamido-4-[(RS)-tetrahydrofuran-2-ylcarbonylmethylthio]azetidin-2-on-1-yl]-2-tri-n-butylphosphoranylideneacetate Thionyl chloride (0.81 ml, 11.1 mmol) in THF (5 ml) was added dropwise to the hydroxy compound (3.663 g, 7.4 mmol) and 2,6-lutidine (1.29 ml, 11.1 mmol) in THF (15 ml) at −20° C. The mixture was stirred 0.5 h, filtered and the filtrate evaporated in vacuo, toluene added and re-evaporated to give t-butyl (RS)-2-chloro-2-[(3R,4R)-3-phenoxyacetamido-4-[(RS)-tetrahydrofuran-2-ylcarbonylmethylthio]azetidin-2-on-1-yl]acetate as a foam (4.222 g).

To the crude chloro compound in dioxan (10 ml) was added tri-n-butylphosphine (4.06 ml, 16.3 mmol), the solution stirred 0.75 h, [Bdiluted with ethyl acetate, washed with dilute sodium hydrogen carbonate solution, water and brine, dried concentrated and flash chromatographed on silica gel eluting with 30,40,50,60,70,80% ethyl acetate in hexane to give the title compound as a foam (3.827 g, 76%); $v_{max}$ ($CH_2Cl_2$) 3417, 1764, 1731, 1690, 1628, 1523, 1171 and 1082 cm$^{-1}$ [Mass spectrum: +ve ion (thioglycerol) MH$^+$ (679)].

(e) t-Butyl (6R,7R)-7-Phenoxyacetamido-3-[(RS)-tetrahydrofuran-2-yl]ceph-3-em-4-carboxylate The phosphorane (3.827 g) and benzoic acid (20 mg) in toluene (75 ml) were purged with argon then heated under argon in an oil bath at 130° C. for 6 h. The solution was left to cool and flash chromatographed on silica gel eluting with 30% ethyl acetate in hexane to give the title compound as a foam (2.267 g, 87%); $v_{max}$($CH_2Cl_2$) 3406, 1785, 1697, 1519, 1155 and 1054 cm$^{-1}$; $δ_H$ (CDCl$_3$, 250 MHz) 1.53, 1.54 (together 9H, 2s), 1.5–2.5 (4H, m), 3.29 and 3.61, 3.39 and 3.56 (together 2H, 2ABq, J18.6, 18.0 Hz), 3.8–4.0 (2H, m), 4.57 (2H, s), 4.9–5.0, 5.05–5.2 (together 1H, 2m), 5.01, 5.02 (together 1H, 2d, J4.8 Hz), 5.84, 5.91 (together 1H, 2dd, J4.8, 9.4 Hz) and 6.9–7.4 (6H, m). [Mass spectrum +ve ion (3-nitrobenzyl alcohol, sodium acetate) MNa$^+$ (483)].

(f) t-Butyl (6R,7R)-7-Amino-3-(tetrahydrofuran-2-yl)ceph-3-em-4-carboxylate

Phosphorus pentachloride (1.538 g, 7.5 mmol) in dichloromethane (39 ml) was added to t-butyl(6R,7R)-7-phenoxyacetamido-3-[(RS)-tetrahydrofuran-2-yl]ceph-3-em-4-carboxylate (2.267 g, 4.9 mmol) and N-methylmorpholine (1.1 ml, 10 mmol) in dichloromethane (20 ml) at −25° C. The reaction was stirred at −10±5° C. for 0.75 h then methanol (10 ml) added all at once, stirred 0.75 h then water (20 ml) added and stirred vigorously for 1 h. The dichloromethane was evaporated in vacuo, the aqueous residue washed with ether then adjusted to pH7 with ammonium hydroxide in the presence of ethyl acetate. The mixture was extracted twice with ethyl acetate, the extracts dried, concentrated and flash chromatographed on silica gel eluting with 30,40,50% ethyl acetate in hexane to give the more mobile (S)-diastereoisomer of the title compound (0.431 g, 27%); (Found: M$^+$, 326.1299. $C_{15}H_{22}N_2O_4S$ requires M, 326.1300); $\nu_{max}$(CH$_2$Cl$_2$) 1777, 1716, 1158 and 1052 cm$^{-1}$; $\delta_H$ (CDCl$_3$, 250 MHz) 1.52 (9H,s), 1.55–1.8 (1H, m), 1.85–2.05 (4H, m), 2.3–2.45 (1H, m), 3.30 and 3.59 (2H, ABq, J18.4 Hz), 3.8–4.0(2H,m), 4.75 (1H, d, J5.0 Hz) and 4.9–5.0 (2H, m). Further elution with 60% ethyl acetate in hexane gave the more polar (R)-diastereoisomer (0.533 g, 33%); (Found: M$^+$ 326.1299. $C_{15}H_{22}N_2O_4S$ requires M, 326.1300) $\nu_{max}$ (CH$_2$Cl$_2$) 1776, 1721, 1158 and 1052 cm$^{-1}$; $\delta_H$ (CDCl$_3$, 250 MHz) 1.41 (2H, bs), 1.54 (9H, s), 1.6–1.85 (1H, m), 1.9–2.05 (2H, m), 2.05–2.2 (1H, m), 3.40 and 3.55 (2H, ABq, J17.8 Hz) 3.8–4.0 (2H, m), 4.67 (1H, d, J5.0 Hz), 4.93 (1H, d, J5.0 Hz), 5.0–5.15 (1H, m).

(g) t-Butyl (6R,7R)-7-[2-(Z)-Methoxyimino-2-(2-tritylaminothiazol-4-yl)acetamido]-3-(tetrahydrofuran-2-yl)-ceph-3-em-4-carboxylate Mesyl chloride (14 μl, 1.8 mmol) was added to 2-(Z)-methoxyimino-2-(2-tritylaminothiazol-4-yl) acetic acid hydrochloride (0.744 g, 1.65 mmol) and N,N-diisopropylethylamine (576 μl, 3.3 mmol) in DMF (5 ml) at −40° C. The reaction mixture was stirred 0.5 h at −30±10° C. then t-butyl (6R,7R)-7-amino-3-(tetrahydrofuran-2-yl)ceph-3-em-4-carboxylate, more mobile diastereoisomer (0.431 g, 1.3 mmol) in DMF (5 ml) followed by pyridine (147 μl, 1.8 mmol) were added. Stirred 1 h without further cooling then diluted with ethyl acetate, washed twice with water and with brine, dried, concentrated and flash chromatographed on silica gel eluting with 30,35 and 40% ethyl acetate in hexane to give the title compound as a foam (0.83 g, 84%); $\nu_{max}$(CH$_2$Cl$_2$) 3396, 3277, 1782, 1732, 1683, 1526, 1248, 1156 and 1051 cm$^{-1}$; $\delta_H$ [(CD$_3$)$_2$SO, 250 MHz] 1.47 (9H, s), 1.55–1.75 (1H, m), 1.8–2.0 (2H, m), 2.05–2.2 (1H, m), 3.44 and 3.50 (2H, ABq, J18.3 Hz), 3.65–3.95 (2H, m), 3.81 (3H, s), 4.6–4.7 (1H, m), 5.14 (1H, d, J4.8 Hz), 5.66 (1H, dd, J4.8, 7.9 Hz), 6.70 (1H, s), 7.2–7.4 (15H, m), 8.88 (1H, s) and 9.54 (1H, d, J7.9 Hz). [Mass spectrum: +ve ion (3-nitrobenzyl alcohol, sodium acetate) MNa$^+$ (774)].

(h) Sodium (6R-7R)-7-[2-(2-Aminothiazol-4-yl)-2-(Z)-methoxyiminoacetamido]-3-[(RS)-tetrahydrofuran-2-yl]ceph-3-em-4-carboxylate t-Butyl (6R,7R)-7-[2-(Z)-methoxyimino-2-(2-tritylaminothiazol-4-yl)acetamido]-3-(tetrahydrofuran-2-yl)ceph-3-em-4-carboxylate, single diastereoisomer (0.832 g, 1.1 mol) in 0.1M hydrochloric acid in 90% formic acid (11 ml) was stood for 1 h, concentrated hydrochloric acid (200 μl) added and left for a further 1.5 h then evaporated to dryness in vacuo. The residue in water (ca 5 ml) was adjusted to pH6.5 with 1M sodium hydroxide solution and chromatographed on HP20SS eluting with 0,1,2 and 3% THF in water. Fractions containing the product, h.p.l.c. analysis, were combined, concentrated and freeze dried to give the title compound as a mixture of diastereoisomers (271 mg, 52%); $\nu_{max}$(KBr) 1762, 1669, 1603, 1530, 1388 and 1039 cm$^{-1}$; $\delta_H$[(CD$_3$)$_2$SO, 250 MHz] 1.4–2.05 (4H, m), 3.19 and 3.36, 3.26 and 3.83 (together 2H, 2ABq, J17.5, 16.8 Hz), 3.55–3.85 (1H, m), 3.83 (3H, s), 4.85–4.95, 5.15–5.25 (together 2H, 2m), 4.96, 4.97 (together 1H, 2d, J4.7 Hz), 5.49, 5.53 (together 1H, 2dd, J4.7, 7.9 Hz), 6.74, 6.75 (together 1H, 2s), 7.24 (2H, s), 9.49, 9.52 (together 1H, 2d, J7.9 Hz) [Mass spectrum +ve ion (thioglycerol) MH$^+$ (476), MNa$^+$ (498)].

The same mixture of diastereoisomers was obtained by progressing the other diastereoisomer isolated in stage (f).

EXAMPLE 2

Pivaloyloxymethyl (6R,7R)-7-[2-(2-Aminothiazol-4-yl)-2-(Z)-methoxyiminoacetamido]-3-[(RS)-tetrahydrofuran-2-yl]ceph-3-em-4-carboxylate Pivaloyloxymethyl bromide (0.15 g) and sodium iodide (0.15 g) in acetone (1 ml) were stirred 0.5 h, filtered and the filtrate evaporated to give the iodide. This in toluene (0.5 ml) was added to sodium (6R,7R)-7-[2-(-2-aminothiazol-4-yl)-2-(Z)-methoxyiminoacetamido]-3-[(RS)-tetrahydrofuran-2-yl]ceph-3-em-4-carboxylate (0.191 g) in N-methylpyrrolidone (1 ml) and stirred 0.5 h. The reaction mixture was diluted with ethyl acetate, washed twice with water and with brine, dried, concentrated and flash chromatographed on silica gel eluting with 80% ethyl acetate in hexane to give the title compound (130 mg, 57%); $\nu_{max}$ (CH$_2$Cl$_2$) 3478, 3391, 1787, 1752, 1685, 1125, 1098 and 1052 cm$^{-1}$; $\delta_H$(CDCl$_3$, 250 MHz), 1.23 (9H,s), 1.6–2.5 (4H, m), 3.37 and 3.66, 3.43 and 3.62 (together 2H, 2ABq, J18.8, 17.8 Hz), 3.8–4.05 (2H, m), 4.10 (3H, s), 4.85–5.0, 5.15–5.25 (together 1H, 2m), 5.07, 5.08 (together 1H, 2d, J4.8, 4.7 Hz), 5.8–6.05 (3H, m), 6.95, 6.96 (together 1H, 2s) and 7.54, 7.65 (together 1H, 2d, J8.8, 8.5 Hz). [Mass spectrum: +ve ion (thioglycerol) MH$^+$ 568)].

EXAMPLE 3

Sodium (6R,7R)-7-[2-(2-Aminothiazol-4-yl)-2-(Z)-methoxyiminoacetamido]-3-[(RS)-tetrahydropyran-2-yl]-ceph-3-em-4-carboxylate (a) Tetrahydropyran-2-carboxylic acid 3,4-Dihydro-2H-pyran-2-carboxylic acid, sodium salt (5.0 g) in water (30 ml) was treated with 10% Palladium on carbon catalyst (0.2 g) and the mixture hydrogenated until there was no further uptake of hydrogen. The mixture was filtered through Kieselguhr, the filtrate passed through a column of 'Amberlite IR120(H$^+$), evaporated in vacuo and the residue dissolved in dichloromethane, dried and evaporated to give the title compound as colourless oil. (3.3 g, 76%); (Found: M$^+$, 130.0631. $C_6H_{10}O_3$ requires M, 130.0630; $\nu_{max}$(CH$_2$Cl) 3500–2750 (v.br), 1772, 1725 cm$^{-1}$; $\delta_H$ (CDCl$_3$), 1.5–1.7 (4H, m), 1.8–2.1 (2H, m), 3.50–3.59 (1H, m), 3.99–4.14 (2H, m) and 7.28 (1H, br.s).

(b) 2-(2-Chloroacetyl)tetrahydropyran

Tetrahydropyran-2-carboxylic acid (3.3 g) in dry dichloromethane (60 ml) was treated with oxalyl chloride (4.8 g, 3.3 ml) and DMF (2–3 drops). After the initial effervescence had ceased the mixture was left for a further 1 h at ambient temperature. The solvent and excess oxalyl chloride were removed in vacuo and the resultant oil ($\nu_{max}$(CH$_2$Cl$_2$)1830 cm$^{-1}$) was dissolved in dichloromethane (20 ml). This acid chloride solution was then added dropwise to a freshly prepared ethereal solution of diazomethane (ca 2 fold excess) cooled to 0–5° C., t.l.c. analysis (60% ethyl acetate in hexane) showed a single mobile spot, i.r. spectrum of a sample showed clean conversion to the diazoketone [$\nu_{max}$ (CH$_2$Cl$_2$) 2100 cm$^{-1}$]. Hydrogen chloride gas was bubbled through the solution until no further starting material was observed by t.l.c. The mixture was washed with brine, dried and the solvent removed in vacuo and the residue purified by flash chromatography on silica gel. The title compound was obtained as a pale yellow oil, (2.8 g, 68%); ν$_{max}$(CH$_2$Cl$_2$) 1740 cm$^{-1}$; δ$_H$ (CDCl$_3$) 1.4–1.7 (4H, m), 1.91–1.98 (2H, m), 3.42–3.53 (1H, m), 3.95–4.07 (2H, m) and 4.48 (2H, s) [Mass spectrum: +ve ion (NH$_3$), MH$^+$ (163), MNH$_4^+$ (180)].

(c) (3R,4R)-3-Phenylacetamido-4-[(RS)-tetrahydropyran-2-ylcarbonylmethylthio]azetidin-2-one 3R,4R-Mercapto-3-phenylacetamidoazetidin-2-one (2.6 g) and 2-(2-chloroacetyl)tetrahydropyran (1.6 g) in DMF (20 ml) were treated with potassium carbonate (1.6 g) at ambient temperature for ca 2 h until t.l.c. (80% ethylacetate in hexane) showed loss of starting material. The reaction mixture was diluted with ethyl acetate, washed with water (×3), brine, dried and concentrated. The title compound was obtained by flash chromatography (60%, 70% ethyl acetate in hexane, ethyl acetate) as a mixture of diastereoisomers as a colourless foam (1.7 g, 70%); ν$_{max}$(CH$_2$Cl$_2$), 3380(w), 1783, 1726, 1684 cm$^{-1}$; δ$_H$ (CDCl$_3$) 1.3–1.7 (4H, m), 1.8–2.0 (2H, m), 3.3–3.6 (3H, m), 3.66 (2H, s), 3.86–3.90 (1H, m), 4.03–4.07 (1H, m), 4.92 (1H, d, J4.6 Hz), 5.51 (1H, dd, J4.4, 8.6 Hz) 6.42 (d, J8.7 Hz), 6.48, 6.51 (together 1H, 2s) and 7.27–7.36 (5H, m). [Mass spectrum: M$^+$ (362)].

(d) t-Butyl (RS)-2-Hydroxy-2-[(3R,4R)-3-phenylacetamido-4-[(RS)-tetrahydropyran-2-ylcarbonylmethylthio]-azetidin-2-on-1-yl]acetate (3R,4R)-3-Phenylacetamido-4-[(RS)-tetrahydropyran-2-yl-carbonylmethylthio]azetidin-2-one (1.7 g) in 1,2-dichloroethane (20 ml) was successively treated with 0.5M t-butyl glyoxylate in 1,2-dichlorethane (10 ml) and triethylamine (50 mg, 70 μl) and monitored by t.l.c. (ethyl acetate) until no starting material remained. The reaction mixture was concentrated and flash chromatography (70% ethyl acetate in hexane, ethyl acetate) to afford the title compound as a yellow foam (1.9 g, 82%); ν$_{max}$ (CH$_2$Cl$_3$) 3400 (w), 1780, 1736, 1687 cm$^{-1}$; δ$_H$ (CDCl$_3$) 1.49 (9H, s) overlapping 1.44–1.61 (4H, m), 1.8–2.0 (2H, m), 3.35–3.58 (3H, m), 3.65 (2H, s), 3.81–3.92 (1H, m), 4.01–4.06 (1H, m), 4.28–4.43 (1H, m), 4.99, 5.00, 5.07 (together 1H, 3d, J4.7 Hz), 5.21, 5.32, 5.33 (together 1H, 3d, J6.8, 7.7, 7.6 Hz), 5.42, 5.50 (together 1H, 2dd, J4.8, 8.7 Hz, 6.35, 6.36, 6.61 (together 1H, 3d, J8.7 Hz) and 7.27–7.38 (5H, m).

(e) t-Butyl 2-[(3R,4R)-3-Phenylacetamido-4-[(RS)-tetrahydropyran-2-ylcarbonylmethylthio]azetidin-2-on-1-yl]-2-tri-n-butylphosphoranylideneacetate t-Butyl 2-hydroxy-2-[(3R,4R)-3-phenylacetamido-4-[(RS)-tetrahydropyran- 2-ylcarbonylmethylthio]azetidin-2-on-1-yl]acetate (1.9 g) in dry THF (10 ml) was treated with 2,6-lutidine (0.62 g, 0.67 ml) followed by thionyl chloride (0.69 g, 0.42 ml) in THF (5 ml) dropwise at <−20° C. under argon. The reaction mixture was allowed to warm slowly to ca 0° C. at which point no starting material was observed by t.l.c. (ethyl acetate). The reaction mixture was filtered and solvent removed in vacuo, the residue dissolved in toluene and evaporated to afford crude t-butyl (RS)-2-chloro-2-(3R,4R)-3-phenylacetamido-4-[(RS)-tetrahydropyran-2-ylcarbonylmethylthio]azetidin-2-on-1-yl]acetate as a brown gum. This was dissolved in dry dioxan (10 ml) and treated with tri-n-butylphosphine (1.79 g, 2.2 ml). The reaction mixture was stirred until loss of starting material was observed by t.l.c. (ethyl acetate) ca 0.5 h. After removal of solvent in vacuo the title compound was obtained by flash chromatography (eluting with 50,60,80% ethyl acetate in hexane, ethyl acetate) as a pale brown foam (1.95 g, 75%); ν$_{max}$(CH$_2$Cl$_2$) 3417(w), 1762, 1681, 1625 cm$^{-1}$. [Mass spectrum +ve ion (thioglycerol) MH$^+$ (677)].

(f) t-Butyl (6R,7R)-7-Phenylacetamido-3-[(RS)-tetrahydropyran-2-yl]ceph-3-em-4-carboxylate t-Butyl 2-[(3R,4R)-3-phenylacetamido-4-(RS)-tetrahydropyran-2-yl]carbonylmethylthio]azetidin-2-on-1-yl]-2-tri-n-butylphosphoranylideneacetate (1.95 g) in dry toluene (50 ml) was refluxed for 8 h under argon. The solvent was removed in vacuo and the title compound obtained by flash chromatography (30% ethyl acetate in dichloromethane) as a yellow foam (1.15 g, 87%); ν$_{max}$ (CH$_2$Cl$_2$), 3415(w), 1783, 1721, 1687 cm$^{-1}$; δ$_H$ (CDCl$_3$), 1.54, 1.56 (together 9H, 2s) overlapping 1.46–1.68 (4H, m), 1.76–1.94 (2H, m), 3.42–3.68 (5H, m), 3.97–4.06 (2H, m), 4.52–4.65 (1H, m), 4.98 (1H, d, J4.8 Hz), 5.68, 5.71 (together 1H, dd, J4.7) and 7.23–7.36 (5H, m). [Mass spectrum: +ve ion (3-nitrobenzyl alcohol, sodium acetate) MNa$^+$ (481)].

(g) t-Butyl (6R,7R)-7-Amino-3-[(RS)-tetrahydropyran-2-yl]ceph-3-em-4-carboxylate t-Butyl (6R,7R)-7-phenylacetamido-3-[(RS)-tetrahydropyran-2-yl]ceph-3-em-4-carboxylate (1.1 g) in dry dichloromethane (50 ml) at −20° C. under argon was successively treated with N-methylmorpholine (0.55 g, 0.6 ml) and phosphorus pentachloride (0.65 g as 16.25 ml of a 40 mg/ml solution in dry dichloromethane) and stirred at −20° C. for 0.75 h. Methanol (50 ml) was added and reaction mixture allowed to warm to ambient temperature over a period of ca 0.5 h. Water (50 ml) was added and reaction mixture stirred vigourously for a further 0.5 h. The dichloromethane was removed in vacuo, ethyl acetate added and aqueous layer adjusted to pH8 with 0.880 ammonia and reextracted with ethyl acetate. The organic extracts were washed with water, brine, dried, concentrated and flash chromatographed on silica gel (eluting with 70,80% ethyl acetate in hexane, ethyl acetate). The first isomer to be eluted (isomer A) was obtained as a white foam (300 mg, 37%); ν$_{max}$ (CH$_2$Cl$_2$) 1776, 1717 cm$^{-1}$; δ$_H$ (CDCl$_3$), 1.53 (9H, s) overlapping 1.4–1.7 (4H, m), 1.73–1.97 (2H, m), 3.35–3.55 (1H, m) overlapping 3.49 and 3.55 (2H, ABq, J18.4 Hz), 3.96–4.00 (1H, m), 4.51–4.55 (1H, m), 4.72 (1H, d, J5.0 Hz) and 4.93 (1H, d, J5.0 Hz). [Mass spectrum: M$^+$ (340)]. The second isomer to be eluted (isomer B) was obtained as a white foam (400 mg, 49%); ν$_{max}$(CH$_2$Cl$_2$), 1715, 1721 cm$^{-1}$; δ$_H$ (CDCl$_3$) 1.56 (9H, s) overlapping 1.49–1.66 (4H, m), 1.84–2.05 (2H, m), 3.44 and 3.62 (2H, ABq, 17.8) overlapping 3.45–3.54 (1H, m), 4.01–4.11 (1H, m), 4.56–4.61 (1H, m), 4.69 (1H, d, J5.0 Hz) and 4.93 (1H, d, J5.0 Hz). [Mass spectrum: M$^+$ (340)].

(h) t-Butyl (6R,7R)-7-[2-(Z)-Methoxyimino-2-(2-tritylaminothiazol-4-yl)acetamido]-3-[tetrahydropyran-2-yl]ceph-3-em-4-carboxylate Mesyl chloride (121 mg, 82 μl) was added to 2-(Z)-methoxyimino-2-(2-tritylaminothiazol-4-yl)acetic acid hydrochloride (466 mg) and N,N-diisopropylethylamine (252 mg, 340 μl) in dry DMF (10 ml) at −50° C. under argon and stirred at −50° C. for 1 h. Then t-butyl (6R,7R)-7amino-3-(tetrahydropyran-2-yl)ceph-3-em-4-carboxylate (Isomer A, 300 mg) in dry DMF (5 ml) followed by pyridine (70 mg, 72 μl) were added and reaction mixture left for a further 1 h whilst warming to ambient temperature. The reaction mixture was partitioned between ethyl acetate and water, reextracted with ethyl acetate, organic extracts washed with water (×3) and brine, dried, concentrated and flash chromatography (eluting with 30,40,50,60% ethyl acetate in hexane) to afford the title compound as a pale yellow foam (420 mg, 62%); ν$_{max}$(CH$_2$Cl$_2$) 3420, 1784, 1732 (shoulder), 1717, 1685 cm$^{-1}$; δ$_H$ (CDCl$_3$), 1.53 (9H, s) overlapping 1.4–1.7 (4H, m), 1.73–1.94 (2H, m), 3.38–3.58 (3H, m), 3.95–4.00 (1H, m), 4.07 (3H, s), 4.54–4.59 (1H, m), 5.02 (1H, d, J4.8 Hz), 5.90 (1H, dd, J4.5, 9.1 Hz) 6.74 (1H, s), 6.86 (1H, d, J8.8 Hz), 7.04 (1H, s) and 7.30 (15H, s). [Mass spectrum: +ve ion (3-nitrobenzyl alcohol, sodium acetate) MNa$^+$ (788)].

(i) Sodium (6R,7R)-7-[2-(2-Aminothiazol-4-yl)-2-(Z)-methoxyiminoacetamido]-3-[(RS)-tetrahydropyran-2-yl]ceph-3-em-4-carboxylate t-Butyl (6R,7R)-7-[2-(Z)-methoxyimino-2-(2-tritylaminothiazol-4-yl)acetamido]-3-(tetrahydropyran-2-yl)ceph-3-em-4-carboxylate (400 mg) was dissolved in 0.1M hydrochloric acid in 90% formic acid (5.22 ml) and set aside for 0.5 h, concentrated hydrochloric acid (50 μl) added and left for a further 1.5 h. The mixture was evaporated in vacuo, diluted with water, adjusted to pH6.7 with sodium bicarbonate, then chromatographed on HP20SS eluting with water then 1,2,4,6,8% THF in water. Fractions containing a diastereoisomeric mixture of the title compound (h.p.l.c.) were concentrated in vacuo and freeze dried (170 mg, 66%); ν$_{max}$(KBr) 1770, 1670, 1600, 1535 cm$^{-1}$; δ$_H$ [(CD$_3$)$_2$SO], 1.3–1.5 (4H, m), 1.6–1.85 (2H, m), 3.24–3.44 (m, masked by HOD peak), 3.83 (3H, s) overlapping 3.76–3.95 (1H, m), 4.46–4.50, 4.82–4.86 (together 1H, 2m), 4.94 (1H, d, J4.7 Hz), 5.46–5.53 (1H, m), 6.74, 6.75 (together 1H, 2s), 7.23 (2H, s) and 9.48, 9.51 (together 1H, 2d, J5.6, 5.5 Hz). [Mass spectrum: +ve ion (thioglycerol) MH$^+$ (490), MNa$^+$ (512)].

The second isomer eluted (isomer B) in step (g) (400 mg) was progressed through step (h) as before yielding a pale yellow foam (550 mg, 61%); ν$_{max}$(CH$_2$Cl$_2$), 3420, 1783, 1729, 1687 cm$^{-1}$; δ$_H$ (CDCl$_3$) 1.55 (9H, s) overlapping 1.44–1.68 (4H, m), 1.82–1.96 (2H, m), 3.44 and 3.65 (2H, ABq, J18.0) overlapping 3.42–3.58 (1H, m), 4.07 (3H, s) overlapping 3.96–4.10 (1H, m), 4.66–4.69 (1H, m), 4.66–4.69 (1H, m), 5.01 (1H, d, J4.7 Hz), 5.86 (1H, dd, J4.8, 8.9 Hz), 6.75 (1H, s) overlapping 6.75–6.78 (1H, m), 7.01 (1H, s) and 7.30 (15H, s). [Mass spectrum: +ve ion (3-nitrobenzyl alcohol, sodium acetate) MNa$^+$ (788)]. This was then progressed through step (i) to afford the same mixture of diastereoisomers.

EXAMPLE 4

Pivaloyloxymethyl (6R,7R)-7-[2-(2-Aminothiazol-4-yl)-2-(Z)-methoxyiminoacetamido]-3-[(RS)-tetrahydropyran-2-yl]ceph-3-em-4-carboxylate The title compound was prepared from the compound of Example 3 as described in Example 2 and obtained as a pale yellow foam (59%); ν$_{max}$(CH$_2$Cl$_2$); 3388, 1787, 1752, 1688 cm$^{-1}$; δ$_H$ (CDCl$_3$) 1.24 (9H, s), 1.42–1.64 (4H, m), 1.74–1.90 (2H, m), 3.40–3.75 (3H, m), 4.07, 4.08 (together 3H, 2s) overlapping 3.96–4.10 (1H, m), 4.56–4.59, 4.80–4.83 (together 1H, 2m), 5.07, 5.08 (together 1H, 2d, J4.8, 4.7 Hz), 5.66 (2H, br.s), 5.85–6.03 (3H, m), 6.86, 6.89 (together 1H, 2s) and 7.59 (1H, d, J8.9 Hz). [Mass spectrum: +ve ion (thioglycerol) MH$^+$ (582); MNa$^+$ (604)].

EXAMPLE 5

(6R,7R)-7-[2-(2-Aminothiazol-4-yl)-2-(Z)-hydroxyiminoacetamido]-3-[(RS)-tetrahydrofuran-2-yl]ceph-3-em-4-carboxylic acid (a) t -Butyl (6R,7R)-3-[(R)-tetrahydrofuran-2-yl]-7-[2-(2-tritylaminothiazol-4-yl)-2-(Z)-trityloxyiminoacetamido]-ceph-3-em-4-carboxylate Methanesulphonyl chloride (96 μl, 1.25 mmol) was added to sodium 2-(2-tritylaminothiazol-4-yl)-2-(Z)-trityloxyiminoacetate (852 mg, 1.2 mmol) in DMF (2 ml) at <−40° C. The mixture was stirred 0.5 h at −30±10° C. then t-butyl (6R,7R)-7-amino-3-[(R)-tetrahydrofuran-2-yl]ceph-3-em-4-carboxylate (326 mg, 1 mmol) in DMF (2 ml), followed by pyridine (101 μl, 1.25 mmol), were added. The reaction was stirred for 1 h without further cooling then diluted with ethyl acetate, washed twice with water and with brine, dried, concentrated in vacuo and flash chromatographed eluting with 25, 30% ethyl acetate in hexane to give the title compound as a colourless foam (665 mg, 68%); ν$_{max}$ (CH$_2$Cl$_2$) 3395, 1787, 1722, 1687, 1527, 1449, 1156 and 1051 cm$^{-1}$; δ$_H$ (CDCl$_3$/CD$_3$OH) 1.55 (9H, s), 1.65–2.25 (4H, m), 3.32 and 3.40 (2H, ABq, J 17.6 Hz), 3.8–4.0 (2H, m), 5.08 (1H, d, J 4.8 Hz), 5.13 (1H, dd, J 7.0, 8.1 Hz), 5.91 (1H, d, J 4.5 Hz), 6.56 (1H, s), 7.2–7.5 (30H, m). [Mass spectrum: +ve ion (3-nitrobenzyl alcohol, sodium acetate) MNa$^+$ (1002)].

(b) (6R,7R)-7-[2-(2-Aminothiazol-4-yl)-2-(Z)-hydroxyiminoacetamido]-3-[(RS)-tetrahydrofuran-2-yl]ceph-3-em-4-carboxylic acid t-Butyl (6R,7R)-3-[(R)-tetrahydrofuran-2-yl]-7-[2-(2-tritylaminothiazol-4-yl)-2-(Z)-trityloxyiminoacetamido]ceph-3-em-4-carboxylate (660 mg) was dissolved in 0.1M hydrochloric acid in 90% formic acid (7 ml) and left for 1 h then concentrated hydrochloric acid (250 μl) was added and left a further 0.75 h. The mixture was evaporated to dryness in vacuo, the residue diluted with water, adjusted to pH3.2 with 0.25M sodium hydroxide then chromatographed on HP20SS eluting with 0 to 15% THF in water. The fractions containing the title compound (h.p.l.c. analysis) were combined, concentrated and freeze-dried to give a colourless solid (102 mg, 35%); ν$_{max}$ (CH$_2$Cl$_2$) 3315, 1763, 1663, 1626, 1178 and 1045 cm$^{-1}$; δ$_H$ [(CD$_3$)$_2$SO] 1.6–2.2 (4H, m), 3.35–3.9 (4H, m), 4.73, 4.95 (together 1H, 2dd, J 8.3, 9.1 Hz), 5.13, 5.15 (together 1H, 2d, J 4.6 Hz), 5.7–5.8 (1H, m), 6.66, 6.68 (together 1H, 2s), 7.14 (2H, s), 9.44, 9.48 (1H, 2d, J 7.9 Hz), 11.30, 11.31 (together 1H, 2s). [Mass spectrum: +ve ion (thioglycerol) MH$^+$ (440)].

EXAMPLE 6

Diastereoisomers of (6R,7R)-7-Amino-3-(tetrahydrofuran-2-yl)ceph-3-em-4-carboxylate (a) (RS)-2-Bromoacetyltetrahydrofuran A stream of diazomethane (from N-methyl-N-nitrosotoluene-4-sulphonamide, 18.0 g) in argon (P. Lombardi, *Chem. and Ind.*, 1990, (21), 708) was passed into a solution of (RS)-tetrahydrofuroyl chloride [prepared from (RS)-tetrahydrofuroic acid (3.48 g, 30 mmol) as described in Example 2(a)] in dichloromethane (60 ml) cooled in an ice bath. When the diazomethane addition was complete, 48% aqueous hydrogen bromide (5.6 ml, 33.2 mmol) was added. The mixture was stirred 0.25 h then washed twice with water, dried, concentrated and flash chromaographed on silica gel eluting with 10% ethyl acetate in hexane to give the title compound as a pale yellow oil (4.44 g, 77%); ν$_{max}$ (CH$_2$Cl$_2$) 1733, 1245, 1073 and 938 cm$^{-1}$; δ$_H$ (CDCl$_3$) 1.85–2.35 (4H, m), 3.85–4.05 (2H, m), 4.20 (2H, s), 4.54 (1H, dd, J 6.1, 8.2 Hz). [Mass spectrum: +ve ion (ammonia) MNH$_4^+$ (210)].

(b) 4-Methoxybenzyl (2RS)-2-hydroxy-2-[(3R,4R)-3-phenylacetamido-4-[(RS)-tetrahydrofuran-2-yl-carbonylmethylthio]-azetidin-2-on-1-yl]acetate Toluene-4-sulphonic acid (6.0 g, 31.5 mmol) in water (15 ml) was added to a solution of 4-methoxybenzyl (2RS)-2-hydroxy-2-[(1R,5R)-3-benzyl-4-thia-2,6-diazabicyclo [3.2.0]hept-2-en-7-on-6-yl]acetate (7.42 g, 18.0 mmol) prepared from Penicillin G as described for the benzhydryl ester derived from Penicillin V, S. Yamamoto, N. Haga, T. Aoki, S. Hayashi, H. Tanida, and W. Nagata, *Heterocycles*, 1977, 8, 283] in dichloromethane (30 ml) and acetone (30 ml).

After stirring for 2.5 h at room temperature, the reaction mixture was diluted with dichloromethane, washed with water (×2), dried and concentrated in vacuo to yield crude 4-methoxybenzyl (2RS)-2-hydroxy-2-[(3R,4R)-4-mercapto-3-phenylacetamidoazetidin-2-on-1-yl]acetate as a yellow foam.

The crude thiol was dissolved in acetone (35 ml) and treated with a solution of (RS)-2-bromoacetyltetrahydrofuran (3.48 g, 18.0 mmol) in acetone (5 ml). After 10 min, potassium carbonate (1.24 g, 8.9 mmol) was added, and the mixture stirred for a further 30 min. The reaction mixture was diluted with ethyl acetate, washed successively with water (×2) and brine, dried and concentrated. The residue was flash chromatographed on silica gel eluting with 50, 70 and is 80% ethyl acetate in hexane yielding the title compound as a colourless foam (5.40 g, 55%); $v_{max}$ (CH$_2$Cl$_2$) 3409, 1781, 1745, 1684, 1613, 1516 cm$^{-1}$. [Mass spectrum +ve ion (3-nitrobenzyl alcohol, sodium acetate) MNa$^+$ (565)].

(c) 4-Methoxybenzyl 2-[(3R,4R)-3-phenylacetamido-4-[(RS)-tetrahydrofuran-2-ylcarbonylmethylthio]azetidin-2-on-1-yl]-2-tri-n-butylphosphoranylideneacetate A solution of thionyl chloride (1.36 ml, 18.6 mmol) in THF (10 ml) was added dropwise to the hydroxy compound (6.72 g, 12.4 mmol) and 2,6-lutidine (2.16 ml, 18.6 mmol) in THF (30 ml) at −20° C. After stirring for 1 h, the reaction mixture was filtered through a pad of celite, and the filtrate evaporated in vacuo. Toluene was added and re-evaporated to yield 4-methoxybenzyl (RS)-2-chloro-2-[(3R,4R)-3-phenylacetamido-4-[(RS)-tetrahydrofuran-2-ylcarbonylmethylthio]azetidin-2-on-1-yl]acetate as an oil.

The crude chloro compound was dissolved in dioxan (30 ml) and treated with tri-n-butylphosphine (6.8 ml, 27.3 mmol). After stirring for 30 min. at room temperature, the reaction mixture was diluted with ethyl acetate and washed successively with dilute sodium hydrogen carbonate solution, water and brine. The organic solution was dried, concentrated and then flash chromatographed on silica gel eluting with 50, then 80% ethyl acetate in hexane to give the title compound as a foam (6.54 g, 73%); $v_{max}$ (CH$_2$Cl$_2$) 3422, 1763, 1732, 1680, 1613, 1515, 1174 cm$^{-1}$. [Mass spectrum +ve ion/thioglycerol) MH$^+$ (727), MNa$^+$ (749)].

(d) 4-Methoxybenzyl (6R,7R)-7-phenylacetamido-3-[(RS)-tetrahydrofuran-2-yl]ceph-3-em-4-carboxylate A solution of the phosphorane (6.40 g, 8.82 mmol) and benzoic acid (20 mg) in toluene (100 ml) was heated in an oil bath at 130° C. for 10 h under argon. The reaction mixture was cooled, concentrated and the residue purified by chromatography on silica gel eluting with 20, 30, 40, 50% ethyl acetate in hexane yielding the title compound as a yellow oil (3.50 g, 78% yield); $v_{max}$ (CH$_2$Cl$_2$) 3411, 1783, 1723, 1688, 1515 cm$^{-1}$; $\delta_H$ (CDCl$_3$, 250 MHz) 1.50–2.39 (together 4H, m), 3.27 and 3.60, 3.32 and 3.49 (together 2H, 2ABq, J 18.7, 17.9 Hz), 3.58 and 3.70, 3.63 and 3.73 (together 2H, 2ABq, J 16.2, 16.1 Hz), 3.80, 3.82 (together 3H, 2S), 3.84–3.97 (together 2H, 2m), 4.91, 5.18 (together 1H, 2m), 4.90, 4.94 (together 1H, 2d, J 4.7 Hz), 5.17 (2H, s), 5.73, 5.82 (together 1H, 2dd, J 9.1, 4.7 Hz), 5.98, 6.02 (together 1H, 2d, J 9.1 Hz), 6.87 and 6.90 (together 2H, 2d, J 8.6 Hz), 7.23–7.40 (7H, m). [Mass spectrum +ve ion (3-nitrobenzylalcohol, sodium acetate) MNa$^+$ (531)].

(e) 4-Methoxybenzyl (6R,7R)-7-amino-3-(tetrahydrofuran-2-yl)ceph-3-em-4-carboxylate Phosphorus pentachloride (2.15 g, 10.32 mmol) in dichloromethane (108 ml) was added to 4-methoxybenzyl (6R,7R)-7-phenylacetamido-3-[(RS)-tetrahydrofuran-2-yl]ceph-3-em-4-carboxylate (3.40 g, 6.69 mmol) and N-methylmorpholine (1.50 ml, 13.64 mmol) in dichloromethane (30 ml) at −25° C. The reaction was stirred at −10±5° C. for 45 min., then methanol (14 ml) was added, and stirring continued for 45 min. at room temperature. Water (27 ml) was then added, and the mixture vigorously stirred for a further 1 h. The dichloromethane was evaporated in vacuo, the aqueous residue washed with diethyl ether, then adjusted to pH7 with ammonium hydroxide in the presence of ethyl acetate. The mixture was extracted with ethyl acetate (×2), dried and concentrated in vacuo. The residue was purified by chromatography on silica gel eluting with 50, 70, 80% ethyl acetate in hexane yielding 4-methoxybenzyl (6R,7R)-7-amino-3-[(S)-tetrahydrofuran-2-yl]ceph-3-em-4-carboxylate (980 mg, 38%) as a yellow foam; $v_{max}$ (CH$_2$Cl$_2$) 1777, 1721, 1613, 1516, 1152 cm$^{-1}$; $\delta_H$ (CDCl$_3$, 250 MHz) 1.53–1.71 (1H, m), 1.84–2.02 (4H, m, 2 exch.), 2.25–2.40 (1H, m), 3.31 and 3.60 (2H, ABq, J 18.5 Hz), 3.78–3.98 (2H, m), 3.81 (3H, s), 4.72 (1H, d, J 5.0 Hz), 4.86–4.93 (2H, m), 5.19 (2H, s), 6.88 (2H, d, J 8.6 Hz), 7.33 (2H, d, J 8.6 Hz). [Mass spectrum: M$^+$ (390)].

Further elution with ethyl acetate gave the more polar diastereoisomer, 4-methoxybenzyl (6R,7R)-7-amino-3-[(R)-tetrahydrofuran-2-yl]ceph-3-em-4-carboxylate (590 mg, 23%). The product was recrystallised using ethyl acetate-hexane to yield an off-white solid m.p. 131–134° C. $v_{max}$ (CH$_2$Cl$_2$) 1775, 1726, 1613, 1516, 1156 cm$^{-1}$; $\delta_H$ (CDCl$_3$, 250 MHz) 1.58–1.70 (1H, m), 1.83–2.06 (4H, m, 2 exch.), 3.38 and 3.57 (2H, ABq, J 17.8 HYz), 3.77–3.93 92H, m), 3.82 (3H, s), 4.68 (1H, d, J 4.9 Hz), 4.92 (1H, d, J 4.9 Hz), 5.07 (1H, m), 5.22 (2H, s), 6.90 (2H, d, J 8.6 Hz), 7.35 (2H, d, J 8.6 Hz). [Mass spectrum: M$^+$ (390)].

EXAMPLE 7

Sodium (6R,7R)-7-[2-(2-aminothiazol-4-yl)-2-(Z)-methoxyiminoacetamido]-3-[(S)-tetrahydrofuran-2-yl]ceph-3-em-4-carboxylate (a) 4-Methoxybenzyl (6R,7R)-7-[2-(2-aminothiazol-4-yl)-2-(Z)-methoxyiminoacetamido]-3-[(S)-tetrahydrofuran-2-yl]ceph-3-em-4-carboxylate Methanesulphonyl chloride (203 μl, 2.62 mmol) was added to 2-(2-aminothiazol-4-yl)-2-(Z)-methoxyiminoacetic acid (528 mg, 2.63 mmol) and N,N-diisopropylethylamine (458 μl, 2.63 mmol) in DMF (8 ml) at −30° C. After stirring at −30±10° C. for 30 min., a solution of 4-methoxybenzyl (6R,7R)-7-amino-3-[(S)-tetrahydrofuran-2-yl]ceph-3-em-4-carboxylate (930 mg, 2.38 mmol) in DMF (5 ml) was added, followed by pyridine (213 μl, 2.63 mmol). The reaction mixture was transferred to an ice-bath and stirring continued for a further 1 h. After dilution with ethyl acetate, the solution was washed successively with saturated sodium hydrogen carbonate solution, 5% aqueous citric acid, water (×2) and brine, dried and then concentrated in vacuo. The residue was purified by chromatography on silica gel eluting with 50, 70 and 90% ethyl acetate in hexane to give the title compound as a yellow foam (1.138 g, 83%); $v_{max}$ (CH$_2$Cl$_2$) 3389, 1783, 1732, 1682, 1516 cm$^{-1}$; $\delta_H$ (CDCl$_3$, 250 MHz) 1.53–1.70 (1H, m), 1.88–2.01 (2H, m), 2.28–2.41 (1H, m), 3.33 and 3.62 (2H, ABq, J 18.7 Hz), 3.79–3.98 (2H, m), 3.81 (3H, s), 4.08 (3H, s), 4.94 (1H, dd, J 9.0, 6.7 Hz), 5.04 (1H, d, J 4.8 Hz), 5.18 (2H, s), 5.88 (2H, br s, exch.), 5.98 (1H, dd, J 9.0, 4.8 Hz), 6.90 (2H, d, J 8.6 Hz), 6.94 (1H, s), 7.35 (2H, d, J 8.6 Hz), 7.50 (1H, br. d, J 9.0 Hz, exch.). [Mass spectrum: +ve ion (thioglycerol) MH$^+$ (574)].

(b) Sodium (6R,7R)-7-[2-(2-aminothiazol-4-yl)-2-(Z)-methoxyiminoacetamido]-3-[(S)-tetrahydrofuran-2-yl] ceph-3-em-4-carboxylate Aluminium chloride (162 mg, 1.21 mmol) was added to anisole (7 ml) and dry dichloromethane (3.5 ml) at −20° C.

and stirred for 15 min. The temperature of the cooling bath was then lowered to −40° C. before addition of a solution of 4-methoxybenzyl (6R,7R)-7-[2-(2-aminothiazol-4-yl)-2-(Z)-methoxyiminoacetamido]-3-[(S)-tetrahydrofuran-2-yl]ceph-3-em-4-carboxylate (235 mg, 0.41 mmol) in dichloromethane (5 ml). After 10 min., the solution was treated with trisodium citrate (0.5M, 12 ml) and then vigorously stirred for 10 min at room temperature. The aqueous phase was separated, washed with dichloromethane (×2) and concentrated in vacuo. The residue was chromatographed on HP20SS eluting with water, then 1% THF in water. Fractions containing the product, (h.p.l.c. analysis), were combined and freeze-dried to give the title compound (126 mg, 65%); $v_{max}$ (KBr) 3401, 1761, 1669, 1603, 1533, 1040 cm$^{-1}$; $\delta_H$ (d$_6$-DMSO, 250 MHz) 1.43–1.59 (1H, m), 1.71–1.88 (2H, m), 2.0–2.12 (1H, m), 3.18 and 3.37 (2H, ABq, J 17.4 Hz), 3.58 (1H, m), 3.78 (1H, m), 3.81 (3H, s), 4.87 (1H, dd, J 8.7, 6.7 Hz), 4.97 (1H, d, J 4.7 Hz), 5.50 (1H, dd, J 8.1, 4.7 Hz), 6.74 (1H, s), 7.21 (2H, br. s, exch.), 9.48 (1H, d, J 8.1 Hz, exch.). [Mass spectrum: +ve ion (thioglycerol) MH$^+$ (476), MNa$^+$ (498)].

EXAMPLE 8

Pivaloyloxymethyl (6R,7R)-7-[2-(2-aminothiazol-4-yl)-2-(Z)-methoxyiminoacetamido]-3-[(S)-tetrahydrofuran-2-yl]ceph-3-em-4-carboxylate Pivaloyloxymethyl bromide (440 mg, 2.26 mmol) and sodium iodide (440 mg, 2.93 mmol) in acetone (3 ml) were stirred for 30 min., filtered, and the filtrate concentrated in vacuo. The resulting iodide in toluene (2 ml) was added to a solution of sodium (6R,7R)-7-[2-(2-aminothiazol-4-yl)-2-(z)-methoxyiminoacetamidol-3-[(S)-tetrahydrofuran-2-yl]ceph-3-em-4-carboxylate (560 mg, 1.18 mmol) in N-methylpyrrolidinone (5 ml). After stirring for 45 min. at room temperature, the reaction mixture was diluted with ethyl acetate, washed successively with water (×3) and brine, dried over MgSO$_4$ and concentrated in vacuo. The residue was chromatographed on silica gel eluting with 80% ethyl acetate in hexane to give the title compound as a yellow foam (486 mg, 73%); $v_{max}$ (CH$_2$Cl$_2$) 3390, 1776, 1749, 1681, 1532 cm$^{-1}$; $\delta_H$ (CDCl$_3$, 250 MHz): 1.22 (9H, s), 1.65 (1H, m), 1.99 (2H, m), 2.41 (1H, m), 3.37 and 3.68 (2H, ABq, J 18.8 Hz), 3.80–4.01 (2H, m), 4.13 (3H, s), 4.92 (1H, dd, J 8.9, 6.8 Hz), 5.08 (1H, d, J 4.8 Hz), 5.85 and 5.92 (2H, ABq, J 5.6 Hz), 5.98 (1H, dd, J 8.4, 4.8 Hz), 6.07 (2H, br s, exch.), 7.03 (1H, s), 7.40 (1H, br. d, exch. J 8.4 Hz). [Mass spectrum: +ve ion (thioglycerol) MH$^+$ (568)].

EXAMPLE 9

Sodium (6R,7R)-7-[2-(2-aminothiazol-4-yl)-2-(Z)-methoxyiminoacetamido]-3-[(R)-tetrahydrofuran-2-yl]ceph-3-em-4-carboxylate (a) 4-Methoxybenzyl (6R,7R)-7-[2-(2-aminothiazol-4-yl)-2-(Z)-methoxyiminoacetamido]-3-[(R)-tetrahydrofuran-2-yl]-ceph-3-em-4-carboxylate Methanesulphonyl chloride (198 μl, 2.56 mmol) was added to 2-(2-aminothiazol-4-yl)-2-(Z)-methoxyiminoacetic acid (515 mg, 2.56 mmol) and N,N-diisopropylethylamine (447 μl, 2.57 mmol) in DMF (8 ml) at −30° C. After stirring at −30±10° C. for 30 min., a solution of 4-methoxybenzyl (6R,7R)-7-amino-3-[(R)-tetrahydrofuran- 2-yl]ceph-3-em-4-carboxylate (915 mg, 2.35 mmol) in DMF (5 ml) was added, followed by pyridine (207 μl, 2.56 mmol). The reaction mixture was transferred to an ice-bath and stirring continued for a further 1.5 h. After dilution with ethyl acetate, the solution was washed successively with saturated sodium hydrogen carbonate solution, 5% aqueous citric acid, water (×2) and brine, dried and then concentrated in vacuo. The residue was triturated several times with diethyl ether to yield the title compound as an off-white solid (1.06 g, 79%); $v_{max}$ (CH$_2$Cl$_2$) 3390, 1783, 1730, 1687, 1606, 1516 cm$^{-1}$; $\delta_H$ (CDCl$_3$, 250 MHz) 1.55–1.70 (1H, m), 1.86–1.98 (2H, m), 2.0–2.14 (1H, m), 3.40 and 3.59 (2H, ABq, J 17.8 Hz), 3.78–3.93 (2H, m), 3.91 (3H, s), 4.12 (3H, s), 5.04 (1H, d, J 4.7 Hz), 5.15 (1H, dd, J 7.7, 7.7 Hz), 5.21 (2H, s), 5.87 (1H, dd, J 8.7, 4.7 Hz), 6.55 (2H, br. s, exch.), 6.90 (2H, d, J 8.6 Hz), 7.05 (1H, s), 7.36 (2H, d, J 8.6 Hz), 7.65 (1H, br. d, J 8.7 Hz). [Mass spectrum: +ve ion (thioglycerol) MH$^+$ (574)].

(b) Sodium (6R,7R)-7-[2-(2-aminothiazol-4-yl)-2-(Z)-methoxyiminoacetamido]-3-[(R)-tetrahydrofuran-2-yl]ceph-3-em-4-carboxylate Aluminium chloride (740 mg, 5.55 mmol) was added to anisole (32 ml) and dry dichloromethane (15 ml) at −20° C. and stirred for 15 min. The temperature of the cooling bath was then lowered to −40° C. before addition of a solution of 4-methoxybenzyl (6R,7R)-7-[2-(2-aminothiazol-4-yl)-2-(Z)-methoxyiminoacetamido]-3-[(R)-tetrahydrofuran-2-yl]ceph-3-em-4-carboxylate (1.06 g, 1.85 mmol) in dichloromethane (10 ml). After 1 min., the solution was treated with trisodium citrate (0.5M, 54 ml) and then vigorously stirred for 10 min. at room temperature. The aqueous phase was separated, washed with dichloromethane (×2) and concentrated in vacuo. The residue was chromatographed on HP20SS eluting with water, then 1% THF in water. Fractions containing the product, (h.p.l.c. analysis), were combined and freeze-dried to give the title compound (560 mg, 64%); $v_{max}$ (KBr) 3399, 1762, 1669, 1603, 1529, 1038 cm$^{-1}$; $\delta_H$ (d$_6$-DMSO, 250 MHz) 1.50–1.91 (4H, m), 3.25 and 3.38 (2H, ABq, J 16.8 Hz), 3.60–3.82 (2H, m), 3.84 (3H, s), 4.96 (1H, d, J 4.7 Hz), 5.20 (1H, dd, J 8.6, 6.0 Hz), 5.48 (1H, dd, J 8.1, 4.7 Hz), 6.76 (1H, s), 7.23 (2H, br. s, exch.), 9.50 (1H, d, J 8.1 Hz, exch.). [Mass spectrum: +ve ion (thioglycerol) MH$^+$ (476), MNa$^+$ (498)].

EXAMPLE 10

Pivaloyloxymethyl (6R,7R)-7-[2-(2-aminothiazol-4-yl)-2-(Z)-methoxyiminoacetamido]-3-[(R)-tetrahydrofuran-2-yl]ceph-3-em-4-carboxylate Pivaloyloxymethyl bromide (247 mg, 1.27 mmol) and sodium iodide (247 mg, 1.65 mmol) in acetone (5 ml) were stirred for 30 min., filtered, and the filtrate concentrated in vacuo. The resulting iodide in toluene (3 ml) was added to a solution of sodium (6R,7R)-7-[2-(2-aminothiazol-4-yl)-2-(Z)-methoxyiminoacetamido]-3-[(R)-tetrahydrofuran-2-yl]ceph-3-em-4-carboxylate (320 mg, 0.67 mmol) in N-methylpyrrolidinone (5 ml). After stirring for 30 min. at room temperature, the reaction mixture was diluted with ethyl acetate, washed successively with water (×3) and brine, dried over MgSO$_4$ and concentrated in vacuo. The residue was chromatographed on silica gel eluting with 80% ethyl acetate in hexane to give the title compound as a yellow foam (297 mg, 78%); $v_{max}$ (CH$_2$Cl$_2$) 3387, 1786, 1752, 1735, 1686, 1605 cm$^{-1}$; $\delta_H$ (CDCl$_3$, 250 MHz) 1.22 (9H, s), 1.69 (1H, m), 1.98 (2H, m), 2.18 (1H, m), 3.43 and 3.62 (2H, ABq, J 18.0 Hz), 3.80–3.96 (2H, m), 4.10 (3H, s), 5.08 (1H, d, J 4.7 Hz), 5.19 (1H, m), 5.83–5.92 (3H, m), 6.32 (2H, br. s, exch), 7.02 (1H, s), 7.63 (1H, br. d, exch., J 8.6 Hz). [Mass spectrum: +ve ion (thioglycerol) MH$^+$ (568)].

EXAMPLE 11

Diphenylmethyl (6R,7R)-7-phenylacetamido-3-[(RS)-tetrahydrofuran-2-yl]ceph-3-em-4-carboxylate (a) Diphenylmethyl (6R,7R)-7-phenylacetamido-3-(tetrahydrofuran-2-yl)ceph-2-em-4-carboxylate A solution of (tetrahydrofuran-2-yl)tri-n-butylstannane (J. S. Sawyer, A. Kucerovy, T. L. MacDonald, and G. J.

McGarvey, *J. Amer. Chem. Soc.*, 1988, 110, 842) (3.0 g, 8.30 mmol) in THF (20 ml) was cooled to −78° C. n-Butyl lithium (6.23 ml of a 1.6M solution in hexane, 9.97 mmol) was then added and the solution was stirred for 15 min. at −78° C. A second flask containing copper (I) bromide.dimethylsulphide complex (0.854 g, 4.14 mmol) suspended in a mixture of dimethyl sulphide (15 ml) and THF (30 ml) was then cooled to −78° C. The α-lithiotetrahydrofuran species was transferred via a cannula to the suspension of copper bromide at −78° C. The red-brown homogeneous solution was stirred for 30 min. at −78° C. A third flask containing a solution of diphenylmethyl 7-phenylacetamido-3-triflyloxyceph-3-em-4-carboxylate (V. Farina, S. R. Baker, and S. I. Hanck, *J. Org. Chem.*, 1989, 54, 4962) (1.9 g, 3.0 mmol) in a mixture of N-methylpyrrolidinone (20 ml) and THF (50 ml) was then cooled to −18° C. The cuprate species was transferred via a cannula to the solution of triflate at −78° C. The reaction mixture was stirred for 1 h at −78° C. then quenched by the addition of saturated aq. ammonium chloride (30 ml). The resulting mixture was allowed to warm to room temperature then diluted with water (100 ml) and extracted with ethyl acetate (100 ml, 30 ml). The combined organic phases were washed with water, brine, then dried over magnesium sulphate. After removal of the solvents under reduced pressure the crude reaction product was purified by flash chromatography on silica gel using 10–30% ethyl acetate/methylene dichloride as eluent. After elution of the 3-n-butylcephem, the title compound was obtained as a mixture of diastereoisomers of the $\Delta^2$ and $\Delta^3$ cephems (1.014 g, 61%).

(b) Diphenylmethyl (6R,7R)-1-oxo-7-phenylacetamido-3-(tetrahydrofuran-2-yl)ceph-3-em-4-carboxylate A mixture of the cephems (1.014 g, 1.83 mmol) obtained in Example 11(a) in methylene dichloride (20 ml) was cooled to 0° C. A solution of m-chloroperbenzoic acid (0.52 g, 60% pure, 1.81 mmol) in methylene dichloride (10 ml) was then added and the solution was stirred for 10 min. at 0° C. The solution was washed with saturated aq. sodium hydrogen carbonate then water and dried ($MgSO_4$). Evaporation of the solvent gave the title compound (1.005 g, 96%) as a mixture of diastereoisomers; $\nu_{max}$ (KBr) 1786, 1728 and 1648 cm$^{-1}$; δ (CDCl$_3$) 1.41–2.29 (4H, m), 2.99, 3.27 (together 1H, 2d, J 19 Hz), 3.63 (2H, br. s), 3.63–3.87 (2.5H, m), 4.20 (0.5H, d), 4.41, 4.43 (together 1H, m), 4.97, 5.14 (together 1H, br. t, J 7.5 Hz, and dd, J, 9, 6.9 Hz), 6.05, 6.09 (together 1H, 2dd, J 10, 4.7 Hz), 6.70, 6.82 (together 1H, 2d, J 10.1 Hz), 6.87, 6.94 (together 1H, 2s) and 7.26–7.40 (15H, m). [Mass spectrum: +ve ion (3-nitrobenzyl alcohol, sodium acetate) MNa$^+$ (593)].

(c) Diphenylmethyl (6R,7R)-7-phenylacetamido-3-(tetrahydrofuran-2-yl)ceph-3-em-4-carboxylate A solution of the sulphoxides (0.975 g, 1.71 mmol) obtained in Example 11(b) in DMF (20 ml) was cooled to −25° C. Phosphorous trichloride (0.30 ml, 3.44 mmol) was then added and the solution was stirred for 10 min. at −25° C. The reaction mixture was poured onto a mixture of ice, water and ethyl acetate. The organic extract was washed with water, brine, dried (MgSO$_4$) and evaporated. Purification by flash chromatography gave the title compound as a mixture of diastereoisomers (0.811 g, 86%); $\nu_{max}$ (KBr) 1780, 1723 and 1663 cm$^{-1}$; δ (CDCl$_3$) 1.5–2.3 (4H, m), 3.24 (0.5H, d, J 18.6 Hz), 3.40 (0.5H, d, J 17.3 Hz), 3.56–3.89 (5H, m), 4.84 (0.5H, dd, J 9.1, 6.7 Hz), 4.95 (1H, d, J 4.8 Hz), 5.01 (0.5H, br t, J 8 Hz) 5.76, 5.85 (together 1H, 2dd, J 8.9, 4.8 Hz), 6.01, 6.08 (together 1H, 2d, J 8.9 Hz), 6.86, 6.94 (1H, 2s) and 7.26–7.38 (15H, m) [mass spectrum: M$^+$ (554)].

EXAMPLE 12

Pivaloyloxymethyl (6R,7R)-7-[2-(2-aminothiazol-4-yl)-2-(Z)-methoxyiminoacetamido]-3-(tetrahydrofuran-2-yl)ceph-3-em-4-carboxylate (a) Pivaloyloxymethyl (6R,7R)-7-phenylacetamido-3-(tetrahydrofuran-2-yl)ceph-3-em-4-carboxylate A solution of the cephems (0.811 g, 1.46 mmol) obtained in Example 11(c) in anisole (5 ml) was cooled to 0° C. Trifluoroacetic acid (10 ml) was added and the mixture was stirred at 0° C. for 5 min. Toluene was added and the solvents were evaporated off. The residue was partitioned between water and ethyl acetate and the pH was adjusted to 7 by the addition of saturated aq. sodium hydrogen carbonate. The aqueous layer was added to ethyl acetate and the pH taken to 2 by the addition of 1M HCl. The organic phase was washed with water, brine, dried (MgSO$_4$) and evaporated. The residue was dissolved in N-methylpyrrolidinone (3 ml). Potassium carbonate (0.426 g, 3.08 mmol) was added followed by a solution of iodomethyl pivalate (prepared from the bromide 0.438 g as in Example 2) in toluene (3 ml). The mixture was stirred for 2 h at room temperature, then water and ethyl acetate were added. The organic phase was washed with water, brine, dried (MgSO$_4$) and evaporated. The residue was purified by chromatography to give the title compound as a (5:1) mixture of diastereoisomers (0.478 g, 65%); major diastereoisomer (S) $\delta_H$ (CDCl$_3$) 1.22 (9H, s), 1.56 (1H, m), 1.96 (2H, m), 2.35 (1H, m), 3.27 (1H, d, J 18.8 Hz), 3.60 (1H, d), 3.65 (2H, ABq, J 16.2 Hz), 3.88 (2H, m), 4.86 (1H, dd, J 9.0, 6.7 Hz), 4.94 (1H, d, J 4.8 Hz), 5.79–6.05 (4H, m) and 7.26–7.38 (5H, m).

(b) Pivaloyloxymethyl (6R,7R)-7-amino-3-(tetrahydrofuran-2-yl)ceph-3-em-4-carboxylate A solution of the diastereoisomers obtained in Example 12(a) (0.478 g, 0.95 mmol) in methylene dichloride (10 ml) was cooled to −30° C. N-Methylmorpholine (0.206 ml, 1.87 mmol) was added followed by a solution of phosphorus pentachloride (0.30 g, 1.44 mmol) in methylene dichloride (7.5 ml). The mixture was stirred at −30° C. for 30 min. Methanol (2.0 ml) was added and the mixture was allowed to warm to room temperature over 30 min. Water (2.6 ml) was then added and the mixture was stirred vigorously for 1 h. The mixture was concentrated by evaporation under reduced pressure and the residue was partitioned between ethyl acetate and water. The pH was adjusted to 7 with 1M aq. ammonia. The organic phase was washed with water, brine, dried (MgSO$_4$) and concentrated. The diastereoisomers were separated by flash chromatography to give (S)-isomer (0.195 g); (Found: M$^+$, 384.1363. C$_{17}$H$_{24}$N$_2$O$_6$S requires M, 384.1355); $\nu_{max}$ (KBr) 3408, 2977, 1780 and 1750 cm$^{-1}$; δ (CDCl$_3$), 1.23 (9H, s), 1.64 (1H, m), 1.98 (2H, m), 2.10 (2H, br. s), 2.39 (1H, m), 3.35 (1H, d, J 18.7 Hz), 3.63 (1H, d, J 18.6 Hz), 3.90 (2H, m), 4.79 (1H, d, J 5.0 Hz), 4.88 (1H, dd, J 9.1, 6.7 Hz), 4.94 (1H, d, J 5.0 Hz) and 5.86 (2H, m). (R)-isomer (0.046 mg); δ (CDCl$_3$) 1.23 (9H, s), 1.6–2.4 (6H, m), 3.43 (1H, d, J 18 Hz), 3.64 (1H, d, J 17.6 Hz), 3.88 (2H, m), 4.79 (1H, d, J 4.9 Hz), 4.99 (1H, d, J 4.9 Hz), 5.17 (1H, t, J 7.5 Hz) and 5.87 (2H, m)

(c) Pivaloyloxymethyl (6R,7R)-7-[2-(2-aminothiazol-4-yl)-2-(Z)-methoxyiminoacetamido]-3-[(S)-tetrahydrofuran-2-yl]ceph-3-em-4-carboxylate A solution of (Z)-2-(2-aminothiazol-4-yl)-2-methoxyiminoacetic acid (0.108 g, 0.537 mmol) in DMF (2 ml) was cooled to −50° C. N,N-Diisopropylethylamine (0.103 ml, 0.59 mmol) followed by methanesulphonyl chloride (0.046 ml, 0.59 mmol) were added and the mixture was stirred at −50° C. for 30 min. A further quantity of N,N-diisopropylethylamine (0.086 ml, 0.493 mmol) was added and this mixture was added to a pre-cooled solution of pivaloyloxymethyl (6R,7R)-7-amino-3-[(S)-tetrahydrofuran-2-yl]ceph-3-em-4-carboxylate (0.185 g, 0.482 mmol) in DMF (2 ml) at 0° C. The resulting mixture was stirred at 0° C. for 40 min., then it was partitioned between ethyl acetate and water. The organic phase was washed with water, brine, dried (MgSO$_4$) and evaporated. The residue was purified by flash chromatography, then triturated with ether to give the title compound (0.193 g, 71%) as a white solid. The spectral data was identical with that obtained for Example 8.

(d) Pivaloyloxymethyl (6R,7R)-7-[2-(2-aminothiazol-4-yl)-2-(Z)-methoxyiminoacetamido]-3-[(R)-tetrahydrofuran-2-yl]ceph-3-em-4-carboxylate A solution of (Z)-2-(2-aminothiazol-4-yl)-2-methoxyiminoacetic acid (27 mg, 0.134 mmol) in DMF (1 ml) was cooled to −50° C. N,N-Diisopropylethylamine (26 μl, 0.15 mmol) followed by methanesulphonyl chloride (11.5 μl, 0.15 mmol) were added and the mixture was stirred at −50° C. for 30 min. A further quantity of N,N-diisopropylethylamine (22 μl, 0.126 mmol) was added and this mixture was added to a pre-cooled solution of pivaloyloxymethyl (6R,7R)-7-amino-3-[(R)]-tetrahydrofuran-2-yl] ceph-3-em-4-carboxylate (46 mg, 0.12 mmol) in DMF (1 ml) at 0° C. The resulting mixture was stirred at 0° C. for 40 min., then it was partitioned between ethyl acetate and water. The organic phase was washed with water, brine, dried (MgSO$_4$) and evaporated. The residue was purified by flash chromatography, then triturated with ether to give the title compound (49.6 mg, 73%) as a white solid. The spectral data was identical with that in Example 10.

EXAMPLE 13

Sodium (6R,7R)-7-[2-(2-Aminothiazol-4-yl)-2-(Z)-methoxyiminoacetamido-3-[(RS)-tetrahydrofuran-3-yl] ceph-3-em-4-carboxylate (a) (RS)-3-Chloroacetyltetrahydrofuran (RS)-3-Tetrahydrofuroic acid (3.48 g) in dichloromethane (40 ml) was treated with oxalyl chloride (11.43 g) as described in Example 1(a). The resultant acid chloride in dichloromethane (40 ml) was then treated with excess diazomethane (60 mM) in ether (100 ml), followed by hydrogen chloride. The solution was washed once with brine, dried and concentrated. Flash chromatography on silica gel, eluting with 40% ethyl acetate/hexane afforded the title compound as a pale yellow oil, (3.924 g, 88%); $v_{max}$ (CH$_2$Cl$_2$) 1735 and 1716 cm$^{-1}$; 2.17 (2H, dt, J 7.0, 7.5 Hz), 3.47–3.58 (1H, m), 3.77–4.04 (4H, m) and 4.18 (2H, s); [mass spectrum: +ve ion (ammonia) MNH$_4^+$ (166)].

(b) (3R,4R)-3-Phenylacetamido-4-[tetrahydrofuran-3-ylcarbonylmethylthio]azetidin-2-one (RS)-3-Chloroacetyltetrahydrofuran (0.297 g) was coupled with (3R,6R)-4-mercapto-3-phenylacetamidoazetidin-2-one (0.519 g) in DMF (4 ml), using potassium carbonate (0.304 g) as described in Example 1(b). Following work up, the crude product was taken up in hot ethyl acetate and cooled. The crystalline product was filtered off. The solvent was removed from the filtrate and the residue triturated with dichloromethane. The crystalline products were combined to give one diastereoisomer of the title compound, (0.187 g, 27%); m.p. 145–155° C. (decomp.); $v_{max}$ (CH$_2$Cl$_2$) 3410, 1748, 1709 (shoulder) and 1688 cm$^{-1}$; $\delta_H$ ((CD$_3$)$_2$SO) 1.74–2.07 (2H, m), 3.26–3.38 (1H, m), 3.48 and 3.56 (2H, ABq, J 16.5 Hz), 3.60–3.75 (4H, m), 4.87 (1H, d, J 4.5 Hz), 5.24 (1H, dd, J 4.5, 8.4 Hz collapses to 1H, d, J 4.5 Hz with D$_2$O) and 9.02 (1H, d, J 8.4 Hz, exchangeable with D$_2$O); [mass spectrum: +ve ion (3NOBA, Na+) MNa$^+$ (371)]. The dichloromethane soluble residue was flash chromatographed with ethyl acetate to give the second diastereoisomer of the title compound as a colourless foam (0.162 g, 23%); $v_{max}$ (CH$_2$Cl$_2$) 3407, 3302 (br), 1783 and 1681 cm$^{-1}$; $\delta_H$ ((CD$_3$)$_2$SO) spectrum identical to that of previous isomer except for 3.44–3.58 (2H, m); [mass spectrum: +ve ion (3NOBA, Na$^+$) MH$^+$ (349), MNa$^+$ (371)].

(c) t-Butyl (RS)-2-Hydroxy-2-[(3R,4R)-3-phenylacetamido-4-[(RS)-tetrahydrofuran-3-ylcarbonylmethylthio]azetidin-2-on-1-yl]acetate t-Butyl glyoxylate (1.601 g) in 1,2-dichloroethane (20 ml) was added to (3R,4R-3-phenylacetamido-4-[(RS)-tetrahydrofuran-3-ylcarbonylmethylthio]azetidin-2-one (2.712 g) with triethylamine (0.079 g, 0.108 ml) in 1,2-dichloroethane (5 ml) at room temperature; after 1 h. the solution was concentrated and flash chromatographed with 70, 80 then 90% ethyl acetate/hexane to give the title compound as a colourless foam, (2.719 g, 73%); $v_{max}$ (CH$_2$Cl$_2$) 3415 (br), 1780, 1735, 1685 and 1509 cm$^{-1}$; $\delta_H$ (CDCl$_3$) 1.48 and 1.51 (9H, 2s's), 2.03–2.18 (2H, m), 3.20–3.32 (1H, m), 3.46 (1H, d, J 17.5 Hz), 3.66 (2H, s), 3.69–3.97 (5H, m), 4.37 and 4.49 (1H, 2 br. d's, J 6.8 and 7.3 Hz, exchangeable with D$_2$O), 4.98 and 5.05 (1H, 2d's, J 4.7 and 4.6 Hz), 5.15–5.50 (2H, 4m's), 6.43–6.74 (1H, 3m's) and 7.32 (5H, m); [mass spectrum: +ve ion (3NOBA, Na$^+$) MNa$^+$ (501)].

(d) t-Butyl 2-[(3R,4R)-3-Phenylacetamido-4-[(RS)-tetrahydrofuran-3-ylcarbonylmethylthio]azetidin-2-on-1-yl]-2-tri-n-butylphosphoranylideneacetate t-Butyl (RS)-2-hydroxy-2-[(3R,4R)-3-phenylacetamido-4-[(RS)-tetrahydrofuran-3-ylcarbonylmethylthio]azetidin-2-on-1-yl]acetate (2.719 g) in THF (20 ml) was treated with thionyl chloride (1.01 g, 0.615 ml) and 2,6-lutidine (0.913 g, 0.989 ml) as described in Example 1(d). Following work-up the crude chloride in dioxan (30 ml) was then treated with n-butylphosphine (2.53 g, 3.11 ml). After purification by flash chromatography with 50, 70% ethyl acetate/hexane then ethyl acetate the title compound was obtained as a pale yellow foam (1.496 g, 40%); $v_{max}$ (CH$_2$Cl$_2$) 3420, 1762, 1717 (shoulder), 1681 and 1625 cm$^{-1}$. [Mass spectrum: +ve ion (3NOBA, Na$^+$), MH$^+$ (663), MNa$^+$ (685)].

(e) t-Butyl (6R,7R)-7-Phenylacetamido-3-[(RS)-tetrahydrofuran-3-yl]ceph-3-em-4-carboxylate t-Butyl 2-[(3R,4R)-3-phenylacetamido-4-[(RS)-tetrahydrofuran-3-ylcarbonylmethylthio]azetidin-2-on-1-yl]-2-tri-n-butylphosphoranylideneacetate (1.496 g), thermolysed in toluene (30 ml) as for Example 1(e) and purified by flash chromatography with 40, 50 and 60% ethyl acetate/hexane afforded the title compound as a yellow foam (0.28 g, 28%); $v_{max}$ (CH$_2$Cl$_2$) 3411, 1702, 1718 and 1687 cm$^{-1}$; $\delta_H$ (CDCl$_3$) 1.52 (9H, s), 1.43–2.39 (3H, m's), 3.23 and 3.44 with 3.27 and 3.44 (2H, 2ABq's J 17.7 Hz), 3.51–4.03 (6H, m's), 4.94 and 4.96 (1H, 2d's, J 4.7 and 4.7 Hz), 5.74–5.82 (1H, m), 6.03 and 6.04 (1H, 2d's, J 8.8 and 8.9 Hz) and 7.26–7.42 (5H, m). [Mass spectrum: +ve ion (3NOBA, Na$^+$) MNa$^+$ (467)].

(f) t-Butyl (6R,7R)-7-Amino-3-[(RS)-tetrahydrofuran-3-yl]ceph-3-em-4-carboxylate t-Butyl (6R,7R)-7-phenylacetamido-3-[(RS)-tetrahydrofuran-3-yl]ceph-3-em-4-carboxylate (0.9 g) in dichloromethane (15 ml) with N-methylmorpholine (0.45 g, 0.49 ml) was successively treated with phosphorus pentachloride (0.549 g) in dichloromethane (13.74 ml), methanol (10 ml) and water (10 ml) as described in Example 2(f). After purification by flash chromatography on silica gel eluting with 60, 80% ethyl acetate/hexane and then ethyl acetate, the title compound was obtained as a yellow solid (0.481 g, 73%); (Found: M⁺, 326.1304. $C_{15}H_{22}N_2O_4S$ requires M, 326.1300); $v_{max}$ ($CH_2Cl_2$) 3408, 1775 and 1716 cm⁻¹; $\delta_H$ (CDCl₃) 1.55 (9H, s), 1.69–2.41 (3H, m's), 3.31 and 3.48 with 3.34 and 3.49 (2H, 2ABq's, J 17.5 and 17.5 Hz), 3.69–3.83 (4H, 2s's overlapping m), 3.97–4.05 (2H, m), 4.72 and 4.74 (1H, 2d's, J 4.3 and 4.4 Hz) and 4.95 and 4.97 (1H, 2d's, J 4.3 and 4.4 Hz).

(g) t-Butyl (6R,7R)-7-[2-(Z)-Methoxyimino-2-(2-tritylaminothiazol-4-yl)acetamido]-3-[(RS)-tetrahydrofuran-3-yl]ceph-3-em-4-carboxylate 2-(Z)-Methoxyimino-2-(2-tritylaminothiazol-4-yl)acetic acid hydrochloride (0.751 g) in DMF (5 ml) was treated with methanesulphonyl chloride (0.179 g, 0.121 ml) and diisopropylethylamine (0.404 g, 0.544 ml) as described in Example 1(g). This was then treated with t-butyl (6R,7R)-7-amino-3-[(RS)-tetrahydrofuran-3-yl]ceph-3-em-4-carboxylate (0.464 g) and pyridine (0.112 g, 0.114 ml) in DMF (5 ml). Following work up and purification by flash chromatography with 40, 50 and 60% ethyl acetate/hexane, the title compound was obtained as a yellow foam (0.874 g, 82%); $v_{max}$ ($CH_2Cl_2$) 3398, 1783, 1731 (shoulder), 1718 and 1688 cm⁻¹; $\delta_H$ (CDCl₃) 1.53 (9H, s), 1.69–2.43 (3H, m's), 3.29 and 3.46 with 3.34 and 3.48 (2H, 2ABq's, J 17.7 and 17.7 Hz), 3.63–4.07 (6H, m's and s), 5.03 and 5.06 (1H, 2d's, J 4.8 and 4.8 Hz), 5.84–5.90 (1H, m), 6.73 and 6.74 (1H, 2s), 6.76 and 6.90 (1H, 2d's, J 8.7 and 8.7 Hz exchangeable with D₂O), 7.02 (1H, br. s, exchangeable with D₂O) and 7.31 (15H, s). [Mass spectrum: +ve ion (3NOBA, Na⁺) MNa⁺ (774)].

(h) Sodium (6R,7R)-7-[2-(2-Aminothiazol-4-yl)-2-(Z)-methoxyiminoacetamido-3-[(RS)-tetrahydrofuran-3-yl]ceph-3-em-4-carboxylate t-Butyl (6R,7R)-7-(2-(Z)-methoxyimino-2-(2-tritylaminothiazol-4-yl)acetamido]-3-[(RS)-tetrahydrofuran-3-yl]ceph-3-em-4-carboxylate (0.859 g) was deprotected in 10% 1M hydrochloric acid in formic acid (11.4 ml) as described in Example 1(h). After work up the pH of the solution was adjusted to 8 with aqueous sodium hydrogen carbonate, and the product purified by column chromatography on HP20SS eluting with 1, 2, 4 and 6% THF/water. The fractions containing the product by h.p.l.c., were combined, concentrated and freeze-dried to give the title compound as an amorphous white solid (0.4 g, 74%); $v_{max}$ (KBr) 1757, 1670, 1596 and 1532 cm⁻¹; $\delta_H$ ((CD₃)₂SO) 1.61–2.08 (3H, m's), 3.15 and 3.37 with 3.18 and 3.37 (2H, 2ABq's, J 16.6 and 16.7 Hz), 3.45–3.66 (2H, m), 3.76–3.95 (5H, m overlapping s at 3.84), 4.96 and 4.97 (1H, 2d's, J 4.3 and 4.6 Hz), 5.46–5.54 (1H, m), 6.75 and 6.76 (1H, 2s's), 7.25 (2H, br s, exchangeable with D₂O). [Mass spectrum: +ve ion (thioglycerol) MH⁺ (476), MNa⁺ (498)].

EXAMPLE 14

4-Methoxybenzyl (6R,7R)-7-Amino-3-((R)-tetrahydrofuran-2-yl)ceph-3-em-4-carboxylate (a) (R)-2-Bromoacetyltetrahydrofuran (R)-2-Tetrahydrofuroic acid (2.739 g, EPA 0382 506) was converted to it's acid chloride with oxalyl chloride (9 g, 6.18 ml) as previously described in Example 1(a). This was dissolved in dichloromethane, cooled in ice/water and saturated with excess diazomethane, bubbled through the solution in a stream of argon. 48% Aqueous hydrogen bromide (4.41 ml) was then added and the reaction mixture vigorously stirred. After 10 min. the solution was washed with brine, dried and concentrated. Flash chromatography eluting with 5% then 10% ethyl acetate/hexane afforded the title compound as a pale yellow oil (3.519 g, 77%); $[\alpha]_D$+60.9 (C 1.01 CHCl₃).

(b) 4-Methoxybenzyl (RS)-2-Hydroxy-2-[(3R,4R)-3-phenylacetamido-4-(R)-tetrahydrofuran-2-ylcarbonylmethylthio)-azetidin-2-on-1-yl]acetate 4-Methoxybenzyl (RS)-2-hydroxy-2-[(1R,5R)-3-benzyl-4-thia-2,6-diazabicyclo[3.2.0]hept-2-en-7-on-6-yl]acetate (4.103 g) in dichloromethane (15 ml) and acetone (15 ml) was ring opened with 4-toluenesulphonic acid hydrate (3.33 g) in water (8 ml) and coupled to (R)-2-bromoacetyltetrahydrofuran (2.11 g) in acetone (20 ml) with potassium carbonate (0.687 g) as described in Example 6(b) for the diastereoisomeric mixture. After purification by flash chromatography, the title compound was obtained as a yellow gum (2.618 g, 49%); $[\alpha]_D$–10.7 (c 1.00 CHCl₃).

(c) 4-Methoxybenzyl 2-[(3R,4R)-3-Phenylacetamido-4-[(R)-tetrahydrofuran-2-ylcarbonylmethylthio]azetidin-2-on-1-yl]-2-tri-n-butylphosphoranylideneacetate 4-Methoxybenzyl (RS)-2-hydroxy-2-[(3R,4R)-3-phenylacetamido-4-((R)-tetrahydrofuran-2-ylcarbonylmethylthio) azetidin-2-on-1-ylacetate (2.558 g) was converted to the title compound with thionyl chloride (0.842 g, 0.51 ml), 2,6-lutidine (0.757 g, 0.82 ml) and tri-n-butylphosphine (2.1 g, 2.58 ml) as described for the diastereoisomeric mixture in Example 6(b). The product was obtained as a brown gum (2.16 g, 63%).

(d) 4-Methoxybenzyl (6R,7R)-7-Phenylacetamido-3-[(R)-tetrahydrofuran-2-yl]ceph-3-em-4-carboxylate The phosphorane (2.16 g) prepared in Example 14(c), in toluene (50 ml) was heated under reflux for 8 h. Removal of solvent and chromatography afforded the title compound as a yellow solid (1.008 g, 67%).

(e) 4-Methoxybenzyl (6R,7R)-7-Amino-3-((R)-tetrahydro-furan-2-yl)ceph-3-em-4-carboxylate The cephem (0.98 g), prepared in Example 14(d) was treated with phosphorus pentachloride (0.523 g) in dichloromethane (13.1 ml) and N-methylmorpholine (0.429 g, 0.466 ml), then methanol (10 mls) and water (10 ml) as described for the diastereoisomeric mixture in Example 6(e). After work up and purification by crystallisation from toluene, the title compound was obtained as a colourless solid (0.252 g, 33%); m.p. 130–132° C.; $[\alpha]_D$+11.5 (c 1.00 CHCl₃); ¹H n.m.r. was shown to be identical to that obtained for (R)-isomer prepared in Example 6(e).

EXAMPLE 15

4-Methoxybenzyl (6R,7R)-7-Amino-3-((S)-tetrahydrofuran-2-yl)ceph-3-em-4-carboxylate (a) (S)-2-Bromoacetyltetrahydrofuran (S)-2-Tetrahydrofuroic acid (5.94 g) was converted to it's acid chloride with oxalyl chloride (13.00 g). This was then converted to the title compound with diazomethane and then 48% aqueous hydrogen bromide (9.58 ml) as described in Example 14(a). After isolation, the product was obtained as pale yellow oil (8.78 g, 89%); $[\alpha]_D$–62.8 (c 1.00, CHCl₃).

(b) 4-Methoxybenzyl (RS)-2-Hydroxy-2-[(3R,4R)-3-phenyl-acetamido-4-((S)-tetrahydrofuran-2-ylcarbonylmethylthio)-azetidin-2-on-1-yl]acetate 4-Methoxybenzyl (RS)-2-hydroxy-2-[(1R,5R)-3-benzyl-4-thia-2,6-diazabicyclo[3.2.0]hept-2-en-7-on-6-yl]acetate (15.09 g) in 50% acetone/dichloromethane (100 ml) was cleaved with 4-toluenesulphonic acid (12.25 g) in water (25 ml). This product was reacted with the crude bromide from Example 15(a) (8.78 g) in acetone (40 ml) in the presence of potassium carbonate (2.53 g) as described in Example 14(b). The title compound was obtained as a yellow foam (12.366 g, 62%).

(c) 4-Methoxybenzyl 2-[(3R,4R)-3-Phenylacetamido-4-[(S)-tetrahydrofuran-2-ylcarbonylmethylthio]azetidin-2-on-1-yl]-2-tri-n-butylphosphoranylideneacetate As for Example 14(c) the alcohol from 15(b) (12.366 g) was converted to the title compound with thionyl chloride (2.47 ml) and 2,6-lutidine (3.99 ml) followed by tri-n- butylphosphine (12.55 ml). After purification the phosphorane was obtained as a brown gum (10 g, 60%).

(d) 4-Methoxybenzyl (6R,7R)-7-Phenylacetamido-3-[(S)-tetrahydrofuran-2-yl]ceph-3-em-4-carboxylate As for Example 14(d) the phosphorane from Example 15(c), (10 g) was cyclized in refluxing toluene (200 mls). After isolation, the title compound was obtained as a yellow foam (5.452 g, 78%).

(e) 4-Methoxybenzyl (6R,7R)-7-Amino-3-((S)-tetrahydrofuran-2-yl)ceph-3-em-4-carboxylate As for Example 14(e) the cephem from 15(d), (5.452 g) was treated with phosphorus pentachloride (2.96 g) and N-methylmorpholine (2.9 ml) in dichloromethane (125 ml), followed by treatment with methanol (50 ml) then water (50 ml). After adjusting the pH to 7 with 0.880 ammonium hydroxide and purification, the title compound was obtained as a pale yellow foam (2.803 g, 67%); $^1$H n.m.r. was shown to be identical to that obtained for the S-isomer prepared in Example 6(c).

EXAMPLE 16

Acetoxymethyl (6R,7R)-7-[2-(2-aminothiazol-4-yl)-2-(Z)-methoxyiminoacetamido]-3-[(S)-tetrahydrofuran-2-yl]ceph-3-em-4-carboxylate (a) Acetoxymethyl (6R,7R)-7-phenylacetamido-3-(tetrahydrofuran-2-yl)ceph-3-em-4-carboxylate To a solution of (6R,7R)-7-phenylacetamido-3-(tetrahydro-furan-2-yl)ceph-3-em-4-carboxylic acid (0.303 g, 0.78 mmol) (obtained in Example 12) in N-methylpyrrolidinone (5 ml) was added potassium carbonate (0.37 g, 2.66 mmol). Bromomethyl acetate (0.30 g, 1.95 mmol) was added dropwise to the mixture over 1 h. The mixture was stirred for a further 1 h, then ethyl acetate and water were added. The organic phase was washed with water, brine, dried (MgSO$_4$) and evaporated. The residue was purified by chromatography to give the title compound as a mixture of diastereomers (0.198 g, 56%); major diastereomer(S); $\delta_H$ (CDCl$_3$) 1.59 (1H, m), 1.95 (2H, m), 2.12 (3H, s), 2.38 (1H, m), 3.28 (1H, d, J 18.9 Hz), 3.59 (1H, d), 3.65 (2H, ABq, J 16.4 Hz), 3.88 (2H, m), 4.89 (1H, dd, J 9.0, 6.7 Hz), 4.93 (1H, d, J 4.9 Hz), 5.84 (3H, m), 6.01 (1H, d, 9.1 Hz) and 7.34 (5H, m)

(b) Acetoxymethyl (6R,7R)-7-amino-3-[(S)-tetrahydrofuran-2-yl]ceph-3-em-4-carboxylate As for Example 12(b), the cephem from Example 16(a), (0.196 g) was treated with phosphorus pentachloride (132 mg) and N-methylmorpholine (94 μl) in dichloromethane (7 ml), followed by treatment with methanol (0.85 ml) then water (1.15 ml). After adjusting the pH to 7 with 1M aq. ammonia and work up, the diastereomers were separated by flash chromatography to give the (S)-isomer (54.3 mg, 37%); $\delta_H$ (CDCl$_3$) 1.66 (1H, m), 1.97 (2H, m), 2.13 (3H, s), 2.40 (1H, m), 3.56 (2H, ABq, J 17.6 Hz), 3.91 (2H, m), 5.03 (3H, m) and 5.84 (2H, m).

(c) Acetoxymethyl (6R,7R)-7-[(Z)-2-(2-aminothiazol-4-yl)-2-(Z)-methoxyiminoacetamido]-3-[(S)-tetrahydrofuran-2-yl]-ceph-3-em-4-carboxylate As for Example 12(c), 2-(2-aminothiazol-4-yl)-2-(Z)-methoxyiminoacetic acid (35 mg) was treated with N,N-diisopropylethylamine (34 and 27 μl) and methanesulphonyl chloride (15 μl) in DMF (1 ml) and then added to the amino compound (53 mg) obtained in Example 16(b) in DMF (1 ml). After work up and chromatography the title compound (60 mg, 74%) was obtained as a foam; $\nu_{max}$ (KBr) 3330, 1774, and 1676 cm$^{-1}$; $\delta_H$ (CDCl$_3$) 1.64 (1H, m), 1.99 (2H, m), 2.14 (3H, s), 2.41 (1H, m), 3.38 and 3.67 (2H, ABq, J 18.9 Hz), 3.90 (2H, m), 4.11 (3H, s), 4.95 (1H, dd, J 9.0, 6.8 Hz), 5.07 (1H, d, J 4.8 Hz), 5.86 (2H, m), 5.99 (1H, dd, J 8.9, 4.8 Hz), 6.08 (2H, brs), 7.00 (1H, s) and 7.49 (1H, d, J 8.8 Hz) [Mass spectrum: +ve ion (ammonia) 526 (MH$^+$)].

EXAMPLE 17

Sodium (6R,7R)-7-[2-(2-Aminothiazol-4-yl)-2-(Z)-methoxyiminoacetamido]-3-(5-methoxymethyltetrahydrofuran-2-yl)ceph-3-em-4-carboxylate (a) (2RS,5SR)-5-Methoxymethyltetrahydrofuran-2-carboxylic acid A solution of 5-methoxymethylfuran-2-carboxylic acid (3.10 g) in ethyl acetate (40 ml) was hydrogenated over 5% rhodium on carbon (200 mg) until hydrogen uptake ceased. The catalyst was filtered off and washed with ethyl acetate. The combined filtrates were evaporated to give the title compound as a colourless oil (3.26 g); $\nu_{max}$ (film) 1750 cm$^{-1}$; $\delta_H$ (CDCl$_3$) 1.75–2.1 (2H,m), 2.1–2.6(2H,m,), 3.45 (3H,s), 3.47 (1H,dd, J 3 and 10 Hz), 3.74 (1H,dd, J 4 and 10 Hz), 4.15–4.43 (1H,m) and 4.43–4.63 (1H,m).

(b) (2RS,5SR)-2-Chloroacetyl-5-methoxymethyltetrahydrofuran

A solution of (2RS,5SR)-5-methoxymethyltetrahydrofuran-2-carboxylic acid (3.1 g) in dichloromethane (50 ml) was treated with oxalyl chloride (2.68 ml) and dimethylformamide (1 drop). The mixture was stirred for 1 h and heated to reflux for 10 mins. The solvent was evaporated and then dichloromethane was evaporated from the residue twice. The product was dissolved in dichloromethane (100 ml) and the solution cooled in an ice bath. Diazomethane was then passed into the solution as described in Example 14(a). When the addition was complete the mixture was stirred at 0° C. for 0.5 h and then hydrogen chloride gas was passed into the solution until all the diazoketone had been consumed. The solution was washed with brine, dried over magnesium sulphate and evaporated. The title compound (2.44 g) was isolated by column chromatography using gradient elution (silica gel, 4:1 going to 1:1 hexane:ethyl acetate); $\nu_{max}$ (film) 1740 cm$^{-1}$; $\delta_H$ (CDCl$_3$) 1.6–2.35 (4H,m), 3.30–3.75 (2H,m), 3.37 (3H,s) and 4.05–4.75 (4H,m).

(c) (3R,4R)-4-[(2RS,5SR)-5-Methoxymethyltetrahydrofuran-2-ylcarbonylmethylthio]-3-phenoxyacetamidoazetidin-2-one Potassium carbonate (1.0 g) was added to a stirred mixture of (3R,4R)-4-mercapto-3-phenoxyacetamidoazetidin-2-one (1.07 g) and (2RS,5SR) 2-chloroacetyl-5-methoxymethyltetrahydrofuran (0.869 g) in dimethylformamide (15 ml). The mixture was stirred at room temperature for 1.5 h and then partitioned between ethyl acetate and water. The organic phase was washed twice with water, then brine, dried over magnesium sulphate and evaporated. The product (0.987 g) was isolated by column chromatography of the residue (silica gel, ethyl acetate as eluent); $\nu_{max}$ (CHCl$_3$) 3411, 3308, 1779 and 1689 cm$^{-1}$; $\delta_H$ (CDCl$_3$) 1.63–1.77 (1H,m), 1.88–2.23 (3H,m), 3.30–3.62 (6H,m), 3.65–3.78 (1H,m), 4.15–4.30, (1H,m), 4.42–4.51 (1H,m), 4.57 (2H,s), 5.04 (1H, d, J 4.0 Hz), 5.60 (1H, dd, J 4.35, 9.09 Hz) 6.90–7.08 (4H,m), 7.28–7.49 (2H, m) and 7.49 (1H,t, J 8.16 Hz).

(d) 4-Methoxybenzyl (2RS)-2-Hydroxy-2-[(3R,4R)-4-[(2RS,5SR)-5-methoxymethyltetrahydrofuran-2-ylcarbonyl-methylthio]-3-phenoxyacetamidoazetidin-2-on-1-yl]-acetate A solution of 4-methoxybenzyl glyoxylate (1.82 g) in dichloroethane (30 ml) was heated at reflux using a Dean and Stark water separator for 1 h. The solution was then cooled to room temperature and then (3R,4R)-4-[(2RS, 5SR)-5-methoxymethyltetrahydrofuran-2-ylcarbonylmethylthio]-3-phenoxyacetamidoazetidin-2-one (2.94 g) in dichloroethane (20 ml) was added followed by triethylamine (0.1 ml). The mixture was stirred at room temperature for 1 h and then the solvents were removed on a rotary evaporator. The product was isolated as a mixture of isomers (3.23 g) by column chromatography of the residue (silica gel, ethyl acetate as eluent); $v_{max}$ (CHCl$_3$) 3411, 1780, 1745 and 1691 cm$^{-1}$.

(e) 4-Methoxybenzyl 2-[(3R,4R)-4-[(2RS,5SR)-5-methoxymethyltetrahydrofuran-2-ylcarbonylmethylthio)]-3-phenoxyacetamidoazetidin-2-on-1-yl]-2-tri-n-butylphosphoranylideneacetate.

2,6-Lutidine (0.95 ml) was added to a stirred solution of 4-methoxybenzyl (2RS)-2-hydroxy-2-[(3R,4R)-4-[(2RS, 5SR)-5-methoxymethyltetrahydrofuran-2-ylcarbonylmethylthio]-3-phenoxyacetamidoazetidin-2-on-1-yl]acetate in tetrahydrofuran (24 ml). A solution of thionyl chloride (0.59 ml) in tetrahydrofuran (4 ml) was then added at <−20° C. and the mixture was stirred for 2 h. The solution was filtered and evaporated and the residue was dissolved in toluene and evaporated again. The crude product was dissolved in dioxan under argon and tri-n-butylphosphine (3.0 ml) was added. The mixture was stirred at room temperature for 0.5 h and then diluted with ethyl acetate and washed with sodium bicarbonate solution, water and brine. The solution was dried over magnesium sulphate and evaporated. The title compound (4.25 g) was isolated by column chromatography of the residue using gradient elution (silica gel 1:1 hexane:ethyl acetate going to neat ethyl acetate); $v_{max}$ (CHCl$_3$) 3421, 1761, 1688 and 1612 cm$^{-1}$.

(f) 4-Methoxybenzyl (6R,7R)-3-[(2RS,5SR)-5-methoxymethyl-tetrahydrofuran-2-yl]-7-phenoxyacetamidoceph-3-em-4-carboxylate.

A solution of 4-methoxybenzyl 2-[(3R,4R)-4-[(2RS, 5SR)-5-methoxymethyltetrahydrofuran-2-ylcarbonylmethylthio]-3-phenoxyacetamidoazetidin-2-on-1-yl]-2-tri-n-butylphosphoranylideneacetate (4.25 g) and benzoic acid (20 mg) in toluene (100 ml) was heated to reflux for 10 h. The mixture was cooled and the solvent evaporated. The product (1.93 g) was isolated by column chromatography of the residue using gradient elution (silica gel 1:1 hexane:ethyl acetate going to neat ethyl acetate); $v_{max}$ (CHCl$_3$) 3409, 1784, 1722 and 1695 cm$^{-1}$.

(g) 4-Methoxybenzyl (6R,7R)-7-Amino-3-(5-methoxymethyl-tetrahydrofuran-2-yl)ceph-3-em-4-carboxylate.

A solution of 4-methoxybenzyl (6R,7R)-3-[(2RS,5SR)-5-methoxymethyltetrahydrofuran-2-yl]-7-phenoxyacetamidoceph-3-em-4-carboxylate (1.93 g) in dichloromethane (25 ml) was cooled to −15 to −20° C., N-methylmorpholine (0.75 ml) was added followed by a solution of phosphorus pentachloride in dichloromethane (26.5 ml of a solution containing 40 mg·ml$^{-1}$). The mixture was stirred at the same temperature for 0–5 h and then methanol (6.8 ml) was added and the mixture stirred at room temperature for 0.5 h. Water (10 ml) was then added and the mixture vigorously stirred for 0.5 h. The dichloromethane was then removed on a rotary evaporator and the residue was partitioned between ether and water. The aqueous phase was stirred with ethyl acetate and the pH was adjusted to 6.2 with 1N aqueous ammonia. The organic phase was washed with water and brine, dried over magnesium sulphate and evaporated. The products were separated by column chromatography of the residue using gradient elution (silica gel, 1:1 hexane:ethyl acetate going to neat ethyl acetate). The following were obtained in order of elution 4-methoxybenzyl (6R,7R)-7-amino-3-[(2S,5R)-5-methoxymethyltetrahydrofuran-2-yl]ceph-3-em-4-carboxylate (388 mg); $v_{max}$ (CHCl$_3$) 3410, 1776 and 1725 cm$^{-1}$; $\delta_H$ (CDCl$_3$) 1.59–1.78 (2H,m), 1.93–2.08 (1H,m), 2.18–2.32 (1H,m), 2.54 (2H, br s), 3.33–3.54 (3H,m), 3.38 (3H,s), 3.80 (3H,s), 4.00–4.11 (1H,m), 4.76 (1H,d, J 4.99 Hz), 4.90 (1H,d, J 4.97 Hz) 4.96 (1H,t, J 8.23 Hz) 5.17 (2H,s), 6.88 (2H,d, J 8.60 Hz) and 7.33 (2H,d, J 8.61 Hz). [Mass spectrum: M$^+$ (434)];
4-methoxybenzyl (6R,7R)-7-amino-3-[(2R,5S)-5-methoxymethyltetrahydrofuran-2-yl]ceph-3-em-4-carboxylate (305 mg); $v_{max}$ (CHCl$_3$) 3409, 1776 and 1725 cm$^{-1}$; $\delta_H$(CDCl$_3$) 1.60–1.81 (2H, m), 1.85–2.01 (2H, m), 3.30–3.50 (2H, m), 3.38 (3H, s), 3.44 (1H,d, J 17.78 Hz), 3.69 (1H, d, J 17.75 Hz), 3.80 (3H, s), 4.00–4.17 (1H,m), 4.70 (1H, d, J 4.92 Hz), 4.93 (1H, d, J 4.95 Hz), 5.10–5.20 (1H, m), 5.18 (1H, d, J 11.88 Hz), 5.24 (1H, d, J 11.89 Hz), 6.88 (1H,d, J 8.65 Hz) and 7.35 (1H, d, J 8.64 Hz). [Mass spectrum: M+ (434)].

(h) 4-Methoxybenzyl (6R,7R)-7-[2-(2-Aminothiazol-4-yl)-2-(Z)-methoxyimingacetamido]-3-[(2R,5S)-5-methoxymethyl-tetrahydrofuran-2-yl]ceph-3-em-4-carboxylate A stirred solution of 2-(2-aminothiazol-4-yl)-2-(Z)-methoxyiminoacetic acid (155 mg) and N,N-diisopropylethylamine (134 μl) in dimethylformamide (3 ml) was cooled to −30° to −40° C. and methanesulphonyl chloride (60 μl) was added. The mixture was stirred at the same temperature for 0.5 h and then a solution of 4-methoxybenzyl (6R,7R)-7-amino-[(2R,5S)-5-methoxymethyltetrahydrofuran-2-yl]ceph-3-em-4-carboxylate (304 mg) in dimethylformamide (3 ml) was added followed by pyridine (60 μl). The mixture was then stirred at 0° C. for 1.5 h, and then partitioned between ethyl acetate and aqueous citric acid solution. The organic phase was washed three times with water, then with brine, dried over magnesium sulphate and evaporated. The title compound (115 mg) was isolated by column chromatography of the residue using gradient elution (silica gel 1:1 hexane:ethyl acetate going to neat ethyl acetate), $v_{max}$ (CHCl$_3$) 3489, 3397, 3330, 1779, 1723, 1681 cm$^{-1}$; $\delta_H$ (CDCl$_3$) 1.60–1.80 (2H,m), 1.78–2.05 (2H,m), 3.30–3.53 (3H,m), 3.37 (3H,s), 3.70 (1H,d, J 17.87 Hz), 3.81 (3H,s), 4.08 (3H,s), 5.05 (1H,d, J 4.79 Hz), 5.18 (1H,d, J 11.81 Hz), 5.24 (1H,d, J 11.62 Hz), 5.90 (1H,dd, J 4.75 and 8.89 Hz), 6.90 (1H,d, J 9.56 Hz), 6.91 (1H,s), 7.34 (1H,d, J 8.67 Hz) and 7.67 (1H,d, J 8.88 Hz).

(i) Sodium (6R,7R)-7-[2-(2-aminothiazol-4-yl)-2-(Z)-methoxyiminoacetamido]-3-[(2SR,5S)-5-methoxymethyl-tetrahydrofuran-2-yl]ceph-3-em-4-carboxylate.

Concentrated hydrochloric acid (0.15 ml) was added to a stirred solution of 4-methoxybenzyl (6R,7R)-7-12-(2-aminothiazol-4-yl)-2-(Z)-methoxyiminoacetamido]-3-[(2R, 5S)-5-methoxymethyltetrahydrofuran-2-yl]ceph-3-em-4-carboxylate (115 mg) in 95% formic acid (4 ml). The mixture was stirred at room temperature for 1.5 h and then the solvents were removed on a rotary evaporator, and then toluene was evaporated from the residue twice. The residue was stirred with water and toluene and the pH of the aqueous phase was adjusted to 6.2 with aqueous sodium bicarbonate solution. The aqueous phase was separated and evaporated and the title compound (36 mg) was obtained as a mixture of isomers by column chromatography of the residue (HP20SS water with increasing proportions of acetone as eluent). Fractions containing product were combined, evaporated, and the residue dissolved in water (5 ml) and freeze-dried; $v_{max}$ (KBr) 1762, 1671 and 1602 cm$^{-1}$; $\delta_H$

[(CD$_3$)$_2$SO] 1.4–2.15 (4H,m), 3.14–3.48 (4H,m), 3.24 and 3.27 (3H, 2s), 3.83 (3H,s), 3.87–3.98 and 4.03–4.18 (1H,m), 4.96 (1H,d,J 4.66 Hz), 5.00 and 5.22 (1H,2t, J 7.47 Hz), 5.46–5.57 (1H,m), 6.74 and 6.75 (1H,2s), 7.25 (2H,s) and 9.49 and 9.53 (1H, 2d, J 8.12 Hz)

EXAMPLE 18

Sodium (6R,7R)-7-[2-(2-Aminothiazol-4-yl)-(Z)-pent-2-enamido]-3-[(S)-tetrahydrofuran-2-yl]ceph-3-em-4-carboxylate.

(a) 4-Methoxybenzyl (6R,7R)-7-[2-(2-Aminothiazol-4-yl)-(Z)-pent-2-enamido-3-[(S)-tetrahydrofuran-2-yl]ceph-3-em-4-carboxylate.

Mesyl chloride (70 μl) was added to 2-(2-aminothiazol-4-yl)-(Z)-pent-2-enoic acid (178 mg) and N,N-diisopropylethylamine (160 μl) in DMF (5 ml) and dichloromethane (5 ml) at −20° C. The reaction mixture was stirred at −20° C. for 1 hour then added to an icecold solution of 4-methoxybenzyl (6R,7R)-7-amino-3-[(S)-tetrahydrofuran-2-yl]ceph-3-em-4-carboxylate (370 mg)and N,N-diisopropylethylamine (160 μl) in dichloromethane (5 ml). Stirred for 1 hour, concentrated and flash chromatographed on silica gel eluting with 30, 50, 60 and 70% ethyl acetate in hexane to give the title compound (90 mg); $v_{max}$ (CHCl$_3$) 1782, 1720, 1674, 1614, 1516, 1134 and 1107 cm$^{-1}$; $\delta_H$ (CDCl$_3$, 250 MHz) 1.12 (3H,t,J 7.5 Hz) 1.50–2.45 (6H,m), 3.30–3.95 (7H,m), 4.85–5.05(2H,m), 5.18 (2H,s), 5.85–5.95 (1H,m), 6.44 (1H,s), 6.52 (1H,t,J 7.8 Hz), 6.90 and 7.32 (4H, ABq, J 8.6 Hz) and 7.43 (1H,d, J 8 Hz). [Mass spectrum: +ve ion (3-nitrobenzyl alcohol, sodium acetate) MNa$^+$ (689)].

(b) Sodium (6R,7R)-7-[2-(2-Aminothiazol-4-yl)-(Z)-pent-2-enamido]-3-[(S)-tetrahydrofuran-2-yl]ceph-3-em-4-carboxylate 4-Methoxybenzyl (6R,7R)-7-[2-(2-aminothiazol-4-yl)-(Z)-pent-2-enamido]-3-[(S)-tetrahydrofuran-2-yl]ceph-3-em-4-carboxylate (80 mg) in dichloromethane (2 ml) was added dropwise to a mixture of aluminium chloride (47 mg) and anisole (1.03 ml) in dichloromethane (2 ml) at −50° C. under argon. The mixture was stirred for 15 minutes at −40° C. and 0.5M trisodium citrate (3.42 ml) added, stirred at room temperature for 15 minutes then diluted with dichloromethane (10 ml) and water (10 ml). The aqueous layer was collected, washed with dichloromethane and chromatographed on HP20SS eluting with 0, 1, 2, 5 and 10% acetone in water. Fractions containing the product, h.p.l.c analysis, were combined, concentrated and freeze-dried to give the title compound (22 mg); $v_{max}$ (KBr) 3407, 1757, 1609, 1527, 1375, 1338 and 1041 cm$^{-1}$; $\delta_H$ D$_2$O, 250 MHz) 1.03 (3H,t,J 7.5 Hz), 1.65–2.30 (6H,m), 3.32 and 3.51 (2H, ABq, J 7.7 Hz), 3.70–3.95 (2H,m), 4.65–4.80 (1H,m), 5.20 (1H,d,J 4.7 Hz), 5.74 (1H,d,J 4.7 Hz), 6.33 (1H,t,J 8 Hz) and 6.47 (1H,s). [Mass spectrum +ve ion (thioglycerol) MH$^+$ (473)].

EXAMPLE 19

Sodium (6R,7R)-7-[2-(2-Aminothiadiazol-4-yl)-2-(Z)-methoxyiminoacetamido]-3-[(S)-tetrahydrofuran-2-yl] ceph-3-em-4-carboxylate (a) 4-Methoxybenzyl (6R,7R)-7-[2-(Z)-Methoxyimino-2-(2-tritylaminothiadiazol-4-yl)acetamido]-3-[(S)-tetrahydrofuran-2-yl]ceph-3-em-4-carboxylate.

Mesyl chloride (65 μl) was added to 2-(Z)-methoxyimino-2-(2-tritylaminothiadiazol-4-yl)acetic acid (370 mg) and N,N-diisopropylethylamine (146 μl) in dichloromethane (5 ml) at −20° C. The reaction mixture was stirred at −20° C. for 1 hour then added to an ice cold solution of 4-methoxybenzyl (6R,7R)-7-amino-3-[(S)-tetrahydrofuran-2-yl]ceph-3-em-4-carboxylate (335 mg) and pyridine (70 μl) in dichloromethane (5 ml). The reaction was stirred for 1 hour, concentrated and flash chromatographed on silica gel eluting with 30,50,60 and 70% ethyl acetate in hexane to afford the title compound as a foam (300 mg); $v_{max}$ (CHCl$_3$) 3398, 1784, 1724, 1691, 1516, 1134 and 1107 cm$^{-1}$; $\delta_H$ CDCl$_3$, 250 MHz) 1.55–1.75 (1H,m), 1.80–2.05 (2H,m), 2.25–2.45 (1H,m), 3.30 and 3.61 (2H, ABq, J 18.3 Hz), 3.75–4.00 (2H,m), 3.81 (3H,m), 4.16 (3H,m), 4.85–5.00 (1H,m), 5.00 (1H,d, J 4.8 Hz), 5.17 (2H,s), 5.92 (1H,dd, J 4.8 Hz), 6.72 (1H,d,J 7.8 Hz) and 6.88 and 7.30 (19H,m). [Mass spectrum: +ve ion (3-nitrobenzyl alcohol, sodium acetate) MNa$^+$ (839)].

(b) Sodium (6R,7R,)-7-[2-(2-Aminothiadiazol-4-yl)-2-(Z)-methoxyiminoacetamido]-3-[(S)-tetrahydrofuran-2-yl) ceph-3-em-4-carboxylate Trifluoroacetic acid (5 ml) was added to 4-methoxybenzyl (6R,7R)-7-[2-(Z)-methoxyimino-2-(2-tritylaminothiadiazol-4-yl)acetamido)-3-[(S)-tetrahydrofuran-2-yl]ceph-3-em-4-carboxylate (100 mg) and anisole (1 ml) in dichloromethane (5 ml) at room temperature and stirred for 1 hour. The mixture was evaporated and re-evaporated from toluene (10 ml). The residue was dissolved in 1% sodium hydrogen carbonate solution (1 ml), washed with ether and chromatographed on HP20SS eluting with 0,0.5 and 1% acetone in water. Fractions containing the product, h.p.l.c analysis, were combined, concentrated and freeze dried to give the title compound (35 mg); $v_{max}$ (KBr) 3381, 1758, 1669, 1602, 1527, 1399 and 1042 cm$^{-1}$; $\delta_H$ (D$_2$O) 1.64–2.25 (4H,m), 3.30 and 3.49 (2H, ABq, J 17.8 Hz), 3.70–3.95 (2H,m), 4.03 (3H,s), 4.65–4.75 (1H,m), 5.19 (1H,d,J 4.7 Hz) and 5.77 (1H,d,J 4.7 Hz). [Mass spectrum: +ve ion (thioglycerol) MH$^+$ (477)].

EXAMPLE 20

(RS)-1-Acetoxyethyl (6R,7R)-7-[2-(2-Aminothiazol-4-yl)-2-(Z)-methoxyiminoacetamido]-3-[(S)-tetrahydrofuran-2-yl]ceph-3-em-4-carboxylate.

A solution of (RS)-1-acetoxyethylbromide (267 mg) in 1-methyl-2-pyrrolidinone (2 ml) was added dropwise, over 1 hour, to an ice cold mixture of sodium (6R,7R)-7-[2-(2-aminothiazol-4-yl)-2-(Z)-methoxyiminoacetamido]-3-[(S)-tetrahydrofuran-2-yl]ceph-3-em-4-carboxylate (190 mg) and potassium carbonate (110 mg) in 1-methyl-2-pyrrolidinone (1 ml). After 15 minutes the mixture was diluted with ethyl acetate, washed with water, brine, dried (MgSO$_4$), concentrated and flash chromatographed on silica gel eluting with 50,70,80 and 90% ethyl acetate in hexane to give the title compound (172 mg); $v_{max}$ (CHCl$_3$) 3019, 2929, 1786, 1683, 1520, 13176 and 1135 cm$^{-1}$; $\delta_H$ (CDCl$_3$, 250 MHz) 1.45–1.75 (4H,m), 1.90–2.10 (2H,m), 2.09 and 2.10 (together 3H, 2s), 2.30–2.50 (1H,m), 3.36 and 3.65 (2H, ABq, J 18.8 Hz), 4.93–5.10 (2H,m), 5.90–6.05 (1H,m), 6.94 and 7.07 (together 1H,q,J 5.8 Hz), 7.10 and 7.15 (together 1H, 2s) and 7.60 and 7.67 (together 1H,2d, J 7.4 Hz); [Mass spectrum: +ve ion (3-nitrobenzyl alcohol, sodium acetate) MNa$^+$ (562)].

EXAMPLE 21

(6R,7R)-7-[2-(2-Aminothiazol-4-yl)-2-(Z)-carboxymethoxy-iminoacetamido]-3-[(RS)-tetrahydrofuran-2-yl]-ceph-3-em-4-carboxylic acid disodium salt.

(a) 4-Methoxybenzyl (6R,7R)-7-[2-(Z)-t-butoxycarbonyl-methoxyimino-2-(2-tritylaminothiazol-4-yl)acetamido]-3-[(R)-tetrahydrofuran-2-yl]ceph-3-em-4-carboxylate.

2-(Z)-t-Butyloxycarbonylmethoxyimino]-2-(2-tritylamino-thiazol-4-yl)acetic acid (179 mg, 0.31 mmol) in DMF (4 ml) was treated at −25° C. with N,N- diisopropylethylamine (52 μl, 0.31 m mol) and methanesulphonyl chloride (24 μl, 0.31 m mol) for 30 min. A mixture of 4-methoxybenzyl (6R,7R)-7-amino-3-[(R)-tetrahydrofuran-2-yl]ceph-3-em-4-carboxylate (119 mg, 0.31 mmol) (See example 6 and pyridine (26 μl, 0.31 mmol) dissolved in DMF (4 ml) was added and stirring was maintained at 0° C. for 1 h. The reaction mixture was partitioned between ethyl acetate and dilute aqueous sodium hydrogen carbonate, the organic layer was washed with aqueous citric acid then water, dried (magnesium sulphate) and evaporated to low bulk. The residue was chromatographed on silica gel eluting with ethyl acetate/hexane mixtures to give the title compound as a cream amorphous solid (190 mg, 69%); $\delta_H$ CDCl$_3$) 1.43 (9H,s), 1.54–1.68 (2H,m), 1.86–1.95 (1H,m), 2.02–2.12 (1H,m), 3.34 and 3.50 (2H, ABq, J 18 Hz), 3.76–3.91 (2H,m), 3.81 (3H,s), 4.76 (2H, br s), 5.02 (1H, d, J 5 Hz), 5.16–5.22 (1H,m), 5.78 (1H, dd, J 5.8 Hz), 6.84 (1H,s), 6.8 (2H, d, J 9 Hz), 7.0 (1H, br s, exch) and 7.26–7.36 (17H,m). [Mass spectrum: +ve ion (3-nitrobenzylalcohol, sodium acetate) MNa$^+$ (938)].

(b) (6R,7R)-7-[2-Aminothiazol-4-yl)-2-(Z)-carboxymethoxy-iminoacetamido]-3-[(RS)-tetrahydrofuran-2-yl]-ceph-3-em-4-carboxylic acid disodium salt.

The product of Example 21(a) (174 mg, 0.19 m mol) was dissolved in a mixture of trifluoroacetic acid; dichloromethane and anisole (4:4:1, 5 ml) and kept at room temperature for 2 h. The solution was evaporated to dryness under reduced pressure and the residue was twice washed with ether. The residue solid was dissolved in water using sodium hydrogen carbonate to bring to pH7.5 then the solution was chromatographed on HP20SS eluting with water. There was some separation of isomers but most of the product was collected as a mixed fraction of (R) and (S) tetrahydrofuryl isomers which was freeze dried to a white solid (42 mg, 44%), $\nu_{max}$ (KBr) 1761, 1660, (sh) 1601 and 1533 cm$^{-1}$; $\delta_H$ (D$_2$O) (major isomer) 1.69–2.18 (4H,m), 3.32 and 3.51 (2H, ABq, J 18 Hz), 3.74–3.93 (2H,m), 4.52 (2H,s), 5.19 (1N, d, J 5 Hz), 5.77 (1H, d, J 5 Hz) and 7.01 (1H,s); (minor isomer) (inter alia), 3.37 and 3.57 (ABq, J 17 Hz), 5.17 (d, J 5 Hz) and 5.76 (d, J 5 Hz). [Mass spectrum: +ve ion (3-nitrobenzyl alcohol, sodium acetate) MNa$^+$ (563)].

EXAMPLE 22

Sodium (6R,7R)-7-[(R)-2-Amino-2-(4-hydroxyphenyl) acetamido]-3-[(S)-tetrahydrofuran-2-yl]ceph-3-em-4-carboxylate.

(a) 4-Methoxybenzyl (6R,7R)-7-[(R)-2-t-butoxycarbonylamino-2-(4-hydroxyphenyl)acetamido]-3-[(R)-tetrahydrofuran-2-yl]ceph-3-em-4-carboxylate 4-Methoxybenzyl (6R,7R)-7-amino-3-[(R)-tetrahydrofuran-2-yl]ceph-3-em-4-carboxylate (136 mg, 0.35 mmol)(See example 6] in THF (10 ml) was stirred in an ice bath with dicyclohexylcarbodiimide (108 mg, 0.52 mmol) then (R)-2-t-butoxycarbonylamino-2-(4-hydroxyphenyl)acetic acid (139 mg, 0.52 mmol) in THF (3 ml) was added dropwise over 2 min. The mixture was stirred at 0° C. for 30 min then at room temperature for 30 min. It was filtered and evaporated and the residue chromatographed on silica gel eluting with ethyl acetate/hexane mixtures. The title compound was obtained as a white solid (212 mg, 95%); $\delta_H$ (CDCl$_3$) 1.10–2.0 (4H,m), 1.42 (9H,s), 3.18 and 3.43 (2H,ABq, J 17 Hz), 3.80 (3H,s), 3.77–3.88 (2H,m), 4.89 (1H,d, J 5 Hz), 5.10 (1H,t, J 7 Hz), 5.11 (1H,d, J 5 Hz), 5.19 (2H, s), 5.65 (1H,d, J 5 Hz exch), 5.69 (1H,dd, J 4.9 Hz), 6.72 (2H,d, J 8 Hz), 6.81 (1H,d, J 9 Hz exch), 6.88 (2H,d, J 9 Hz), 7.10 (2H,d, J 8 Hz) and 7.33 (2H,d,J 9 Hz).

[Mass spectrum: +ve ion (3-nitrobenzyl alcohol, sodium acetate) MNa$^+$ (938)].

(b) Sodium (6R,7R)-7-[(R)-2-Amino-2-(4-hydroxyphenyl)-acetamido]-3-[(RS)-tetrahydrofuran-2-yl] ceph-3-em-4-carboxylate The product of Example 22(a) (42 mg, 0.66 mmol) was treated as in Example 21(b). The final chromatography on HP20SS yielded two fractions. The first fraction to be eluted was the pure (S)-tetrahydrofuran-2-yl isomer (53 mg, 19%) as a white freeze dried solid; $\nu_{max}$ (KBr) 1762, 1690 and 1600 cm$^{-1}$; $\delta_H$ D$_2$O) 1.62–1.74 (1H,m), 1.87–1.98 (2H,m), 2.15–2.05 (1H,m), 3.10 and 3.39 (2H, ABq, J 18 Hz), 3.72–3.90 (2H,m), 4.66 (1H,t, J 8 Hz), 5.04 (1H,d, J 4.5 Hz), 5.61 (1H,d, J 4.5 Hz), 6.90 (1H,d, J 9 Hz) and 7.31 (2H,d, J 9 Hz) Further elution of the column gave a mixture of diastereoisomers (84 mg, 30%).

EXAMPLE 23

Sodium (1S,6R,7R)-7-[2-(2-Aminothiazol-4-yl)-2-(Z)-methoxyiminoacetamido]-3-[(S)-tetrahydrofuran-2-yl] ceph-3-em-4-carboxylate-1-oxide (a) 4-Methoxybenzyl (1S,6R,7R)-7-[2-(2-Aminothiazol-4-yl)-2-(Z)-methoxyiminoacetamido]-3-[(S)-tetrahydrofuran-2-yl]ceph-3-em-4-carboxylate-1-oxide 4-Methoxybenzyl (6R,7R)-7-[2-(2-aminothiazol-4-yl)-2-(Z)-methoxyiminoacetamido]-3-[(S)-tetrahydrofuran-2-yl] ceph-3-em-4-carboxylate (see example 7) (250 mg, 0.44 mmol) in ethyl acetate (25 ml) was stirred in an ice bath and a solution of m-chloroperbenzoic acid (75 mg, 0.44 mmol) in ethyl acetate (5 ml) was added. After 10 min the reaction mixture was washed with dilute aqueous sodium hydrogen carbonate then water followed by drying (magnesium sulphate) and evaporation under reduced pressure. The residue was chromatographed on silica gel eluting with acetone/ethyl acetate mixtures to give the title compound as a white solid (179 mg, 69%); $\nu_{max}$ (CHCl$_3$) 1800, 1730, 1680 and 1610 cm$^{-1}$; $\delta_H$ (CDCl$_3$) 1.48–1.64 (1H,m), 1.89–2.00 (2H, m), 2.33–2.47 (1H,m), 3.29 and 3.75 (2H, ABq, J 19 Hz), 3.82 (3H,s), 3.84–3.96 (2H,m), 4.09 (3H,s), 5.06 (1H,dd, J 7, 9 Hz), 5.22 (2H,s), 5.55–5.8 (1H, br s, exch), 6.16 (1H,dd, J 4.5, 10 Hz), 6.91 (2H,d, J 7.9 Hz), 6.98 (1H,s), 7.35 (2H,d, J 9 Hz) and 7.55–7.65 (1H,br, exch). [Mass spectrum: +ve ion (thioglycerol) MH$^+$ (590)].

(b) Sodium (1S,6R,7R)-7-[2-(2-aminothiazol-4-yl)-2-(Z)-methoxyiminoacetamido]-3-[(S)-tetrahydrofuran-2-yl] ceph-3-em-4-carboxylate-1-oxide Anhydrous aluminium chloride (115 mg, 0.86 mmol) was added to a mixture of anisole (5 ml) and dichloromethane (3 ml) cooled to −20° C. After 15 mins at −20° C. the mixture was cooled to −40° C. and a solution of the product of Example 23(a) (170 mg, 0.29 mmol) in dichloromethane (4 ml) was then added. The mixture was then stirred at −40° C. for 10 min when a 0.5M aqueous solution of trisodium citrate (9 ml) was added. After vigoursly stirring at room temperature the aqueous layer was separated, twice washed with dichloromethane then concentrated under reduced pressure. The residue was chromatographed on HP20SS eluting with water containing up to 2% acetonitrile. Pure fractions (as determined by HPLC) were combined and freeze dried to give the title compound as a white solid (71 mg, 50%); $\nu_{max}$ (KBr) 1775, 1669 and 1607 (br) cm$^{-1}$; $\delta_H$ (D$_2$O) 1.54–1.70 (1H,m), 1.94–2.03 (2H,m), 2.15–2.28 (1H,m), 3.44 and 3.85 (2H, ABq, J 18 Hz), 3.8–4.0 (2H,m), 3.99 (3H,s), 4.86 (1H,t, J 8 Hz), 4.99 (1H,d, J 4.5 Hz), 5.95 (1H,d, J 4.5 Hz) and 7.01 (1H,s). [Mass spectrum: +ve ion (thioglycerol) MH$^+$ (492)].

EXAMPLE 24

Sodium 7-[2-(2-aminothiazol-4-yl)-2-(Z)-methoxyiminoacetamido]-3-(tetrahydrofuran-2-yl)-1-carba-1-dethiaceph-3-em-4-carboxylate (a) 4-Methoxybenzyl 2-diazo-3-oxo-5-[(3SR,4RS)-3-phenylacetamidoazetidin-2-on-4-yl]pentanoate A solution of 4-methoxybenzyl 3-oxo-5-[(3SR,4RS)-3-phenylacetamidoazetidin-2-on-4-yl]pentanoate (1.38 g, 3.15 mmol) [prepared by the method described for 4-nitrobenzyl 3-oxo-5-[(3SR,4RS)-3-phenoxyacetamidoazetidin-2-on-4-yl]pentanoate, C. Bodurow and M. A. Carr, *Tetrahedron Lett.*, 1989, 30, 4801] in acetonitrile (60 ml) was treated with 4-toluenesulphonyl azide (870 mg, 4.42 mmol) and N,N-diisopropylethylamine (822 μl, 4.73 mmol) at 0° C. After 10 min., the ice-bath was removed and stirring was continued at room temperature for 2 h. The reaction mixture was diluted with ethyl acetate and washed with brine. After drying over $MgSO_4$, the solvent was evaporated in vacuo and the residue purified by chromatography on silica gel eluting with-ethyl acetate to yield the title compound (1.279, 87%); $v_{max}$ (KBr) 2134, 1775, 1717, 1654, 1513 and 1304 $cm^{-1}$; $\delta_H$ ($CDCl_3$, 250 MHz) 1.59–1.70 (2H,m), 2.68–2.95 (2H,m), 3.55 and 3.65 (2H, ABq, J 15.6 Hz), 3.78 (1H,m), 3.82 (3H,s), 5.19 (2H,s), 5.25 (1H, ddd, J 8.1, 4.9, 1.0 Hz), 6.25 (1H, br s, exch.), 6.49 (1H, br d, J 8.1 Hz, exch.), 6.90 (2H,d, J 8.7 Hz) and 7.23–7.70 (7H,m). [Mass spectrum: +ve ion (3-nitrobenzyl alcohol, sodium acetate) $MNa^+$ (487)].

(b) 4-Methoxybenzyl (6RS,7SR)-7-Phenylacetamido-3-(trifluoromethylsulphanyloxy)-1-carba-1-dethiaceph-3-em-4-carboxylate A solution of 4-methoxybenzyl 2-diazo-3-oxo-5-[(3SR,4RS)-3-phenylacetamidoazetidin-2-on-4-yl]pentanoate (1.54 g, 3.32 mmol) in chloroform (40 ml) was heated to reflux in the presence of a catalytic quantity of rhodium (II) acetate dimer. After heating for 45 min., the reaction mixture was cooled to 0° C. and treated sequentially with N,N-diisopropylethylamine (1.16 ml, 6.66 mmol) and trifluoromethanesulphonic anhydride (0.61 ml 3.65 mmol). After stirring for 30 min at 0° C., the mixture was concentrated in vacuo. The residue was purified by chromatogrphy on silica gel eluting with 30, then 50% ethyl acetate in hexane yielding the title compound as an orange foam (1.20 g, 64%); $v_{max}$ ($CH_2Cl_2$) 3417, 1783, 1733, 1684, 1516 and 1430 $cm^{-1}$; $\delta_H$ ($CDCl_3$, 250 MHz) 1.45 (1H,m), 2.01 (1H,m), 2.56 (2H,m), 3.58 and 3.64 (2H, ABq, J 16.1 Hz), 3.80 (3H,s), 3.87 (1H,m), 5.14–5.35 (3H,m), 5.89 (1H, br d, J 6.2 Hz, exch), 6.87 (2H, d, J 8.7 Hz) and 7.22–7.41 (7H,m),. [Mass spectrum: +ve ion (ammonia) $MH^+$ (569), $MNH_4^+$ (586)].

(c) 4-Methoxybenzyl (6RS,7SR)-7-Phenylacetamido-3-[(RS)-tetrahydrofuran-2-yl]-1-carba-1-dethiaceph-3-em-4-carboxylate A solution of 4-methoxybenzyl (6RS,7SR)-7-Phenylacetamido-3-(trifluoromethylsulphonyloxy)-1-carba-1-dethiaceph-3-em-4-carboxylate (1.13 g, 199 mmol) in THF (15 ml) was treated with the cuprate species generated from (tetrahydrofuran-2-yl)-tri-n-butylstannane (1.97 g, 5.46 mmol), n-butyllithium (4.1 ml of a 1.6M solution in hexane, 6.56 mmol) and copper (I) bromide dimethylsulphide complex (565 mg, 2.75 mmol) as described in Example 11(a). Following work-up, the crude reaction product was purified by chromatography on silica gel eluting with 10, 20 and 30% ethyl acetate hexane. After elution of the 3-n-butylcarbacephem (340 mg, 36%), the title compound was obtained as a mixture of diastereoisomers (478 mg, 50%); (found: M+, 490.2096. $C_{28}$ $H_{30}$ $N_2$ $O_6$ requires M+ 490.2104.); $v_{max}$ ($CH_2Cl_2$) 3422, 1769, 1719, 1682, 1515 and 1389 $cm^{-1}$; $\delta_H$ ($CDCl_3$, 250 MHz) 1.45–2.70 (8H,m), 3.58 and 3.67 (2H, ABq, J 16.0 Hz), 3.72–3.90 (3H,m), 3.80 (3H,S), 4.93 and 5.09 (together 1H, 2dd, J 8.9, 6.8 and 7.9, 7.9 Hz), 5.13–5.28 (3H,m), 5.80 and 5.85 (together 1H, 2d, J 6.6, 7.7 Hz, exch.), 6.89 (2H,d, J 8.7 Hz) and 7.20–7.41 (7H,m).

(d) 4-Methoxybenzyl (6RS,7SR)-7-amino-3-(tetrahydrofuran-2-yl)-1-carba-1-dethiaceph-3-em-4-carboxylate A solution of 4-methoxybenzyl (6RS,7SR)-7-phenylacetamido-3-[(RS)-tetrahydrofuran-2-yl]-1-carba-1-dethiaceph-3-em-4-carboxylate (560 mg, 1.14 mmol) and N-methylmorpholine (250 μl, 2.27 mmol) in dichloromethane (15 ml) was treated successively with phosphorus pentachloride (357 mg, 1.71 mmol) in dichloromethane (9 ml), methanol (2.5 ml) and water (5 ml) as described in Example 1(f). Purification by chromatography on silica gel eluting with ethyl acetate and then 5% methanol in ethyl acetate yielded 4-methoxybenzyl (6RS,7SR)-7-amino-3-[(SR)-tetrahydrofuran-2-yl]-1-carba-1-dethiaceph- 3-em-4-carboxylate (166 mg, 39%) as a colourless foam; $v_{max}$ ($CH_2Cl_2$) 3401, 1761, 1716, 1613 and 1516 $cm^{-1}$; $\delta_H$ ($CDCl_3$, 250 MHz) 1.50–1.68 (2H,m), 1.85–1.97 (2H,m), 2.12–2.32 (2H,m), 2.35–2.45 (2H,m), 2.70 (2H, br s, exch.), 3.70–3.92 (3H,m), 3.78 (3H,s), 4.58 (1H,d, J 5.3 Hz), 4.94 (1H,dd, J 8.8, 7.0 Hz), 5.16 (2H,s), 6.87 (2H,d, J 8.7 Hz) and 7.31 (2H,d, J 8.7 Hz). [Mass spectrum: +ve ion (3-nitrobenzyl alcohol, sodium acetate) $MNa^+$ (395)]. Further elution of the column yielded the more polar diastereoisomer 4-methoxybenzyl (6RS,7SR)-7-amino-3-[(RS)-tetrahydrofuran-2-yl]-1-carba-1-dethiaceph-3-em-4-carboxylate (132 mg, 31%) as a pale yellow foam; $v_{max}$ ($CH_2Cl_2$) 3408, 1761, 1722, 1613 and 1516 $cm^{-1}$; $\delta_H$ ($CDCl_3$, 250 MHz) 1.52–1.72 (2H,m), 1.80–2.00 (2H,m), 2.06–2.22 (2H,m), 2.50–2.78 (4H,m, 2H exch), 3.69–3.90 (3H,m), 3.78 (3H,s), 4.51 (1H,d, J 5.3 Hz), 5.06 (1H,dd, J 7.8, 7.8 Hz), 5.20 (2H,s), 6.87 (2H,d, J 8.6 Hz) and 7.34 (2H,d, J 8.6 Hz). [Mass spectrum: +ve ion (3-nitrobenzyl alcohol, sodium acetate) $MNa^+$ (395)].

(e) 4-Methoxybenzyl (6RS,7SR)-7-[2-(2-aminothiazol-4-yl)-2-(Z)-methoxyaminoacetamido]-3-[(SR)-tetrahydrofuran-2-yl]-1-carba-1-dethiaceph-3-em-4-carboxylate 2-(2-Aminothiazol-4-yl)-2-(Z)-methoxyiminoacetic acid (99 mg,0.49 mmol) in DMF (5 ml) was treated with methansulphonyl chloride (38 μl,0.49 mmol) and N,N-diisopropylethylamine (86 μl, 0.49 mmol) as described in Example 7(a). This was then treated successively with a solution of 4-methoxybenzyl (6RS,7SR)-7-amino-3-[(SR)-tetrahydrofuran-2-yl]-1-carba-1-dethiaceph-3-em-4-carboxylate (160 mg,0.43 mmol) in DMF (5 ml) and pyridine (40 μl, 0.49 mmol). After work-up, the product was purified by chromatography on silica gel eluting with ethyl acetate to yield the title compound (169 mg, 71%); $v_{max}$ (KBr) 3313, 1763, 1717, 1676, 1612 and 1514 $cm^{-1}$; $\delta_H$ ($CDCl_3$, 250 MHz) 1.48–1.62 (2H,m), 1.83–1.98 (2H,m), 2.10–2.49 (6H,m, 2H exch.), 3.78–3.98 (3H,m), 3.79 (3H,s), 4.08 (3H,s), 4.98 (1H,dd, J 8.8, 6.9 Hz), 5.13 and 5.20 (2H, ABq, J 12.2 Hz), 5.48 (1H,dd, J 7.0, 5.0 Hz), 6.89 (2H,d, J 8.6 Hz), 7.00 (1H,s), 7.35 (2H,d, J 8.6 Hz) and 7.82 (1H, br s, exch.). [Mass spectrum: +ve ion (3-nitrobenzylalcohol, sodium acetate) $MH^+$ (556) $MNa^+$ (578)].

(f) 4-methoxybenzyl (6RS,7SR)-7-[2-(2-aminothiazol-4-yl)-2-(Z)-methoxyiminoacetamido]-3-[(RS)-tetrahydrofuran-2-yl]-1-carba-1-dethiaceph-3-em-4-carboxylate 2-(2-Aminothiazol-4-yl)-2-(Z)-methoxyiminoacetic acid (74 mg, 0.37 mmol) in DMF (5 ml) was treated with methanesulphonyl chloride (29 μl, 0.37 mmol) and N,N-diisopropylethylamine (64 μl, 0.37 mmol) as described in Example 7(a). This was then treated successively with a solution of 4-methoxybenzyl (6RS,7SR)-7-amino-3-[(RS)-tetrahydrofuran-2-yl]-1-carba-1-dethiaceph-3-em-4-carboxylate (125 mg, 0.34 mmol) in DMF (5 ml) and pyridine (30 μl, 0.37 mmol). After work-up, the product was purified by triturating with diethyl ether to yield the title compound (148 mg, 78%); $v_{max}$ (KBr) 3343, 1751, 1718, 1678 and 1515 cm$^{-1}$; $\delta_H$ CDCl$_3$, 250 MHz) 1.25–1.30 (2H,m), 1.50–2.78 (8H,m, 2H exch.), 3.75–3.95 (3H,m), 3.78 (3H,s), 4.12 (3H,s), 5.12 (1H,dd, J 7.8, 7.4 Hz), 5.19 (2H,s), 5.43 (1H,dd, J 7.3, 5.1 Hz), 6.88 (2H, d, J 8.7 Hz), 7.05 (1H,s), 7.35 (2H,d, J 8.7 Hz) and 8.09 (1H, br s, exch.). [Mass spectrum: +ve ion (3-nitrobenzyl alcohol, sodium acetate) MH$^+$ (556), MNa$^+$ (578)].

(g) Sodium (6RS,7SR)-7-[2-(aminothiazol-4-yl)-2-(Z)-methoxyiminoacetamido]-3-[(SR)-tetrahydrofuran-2-yl]-1-carba-1-dethiaceph-3-em-4-carboxylate A solution of 4-methoxybenzyl (6RS,7SR)-7-[2-(2-aminothiazol-4-yl)-2-(Z)-methoxyiminoacetamido]-3-[(SR)-tetrahydrofuran-2-yl]-1-carba-1-dethiaceph-3-em-4-carboxylate (160 mg, 0.29 mmol) in dichloromethane (10 ml) was added to a solution of aluminium chloride (115 mg, 0.85 mmol) in anisole (4.5 ml) and dichloromethane (2.5 ml) as described in Example 7(b). After quenching with trisodium citrate (0.5M, 9 ml) and subsequent work-up, the product was purified by chromotography on HP20SS eluting with water, then 1 and 2% THF in water. Fractions containing the product (h.p.l.c. analysis) were combined and freeze-dried to give the title compound (94 mg, 71%); $v_{max}$ (KBr) 1745, 1663, 1595, 1532 and 1387 cm$^{-1}$; $\delta_H$ (d$_6$-DMSO, 250 MHz) 1.38–1.55 (2H,m), 1.70–1.88 (3H,m), 1.97–2.16 (3H, m), 3.52–3.79 (3H,m), 3.82 (3H,s,), 4.95 (1H,dd, J 8.4, 7.0 Hz), 5.22 (1H,dd, J 8.6, 4.9 Hz), 6.73 (1H,s), 7.23 (2H, br s, exch.) and 9.18 (1H,d, J 8.6 Hz, exch.). [Mass spectrum: +ve ion (thioglycerol) MH$^+$ (458)].

(h) Sodium (6RS,7SR)-7-[2-(2-aminothiazol-4-yl)-2-(Z)-methoxyiminoacetamido]-3-[(RS)-tetrahydrofuran-2-yl]-1-carba-1-dethiaceph-3-em-4-carboxylate A solution of 4-methoxybenzyl (6RS,7SR)-7-[2-(2-aminothiazol-4-yl)-2-(Z)-methoxyaminoacetamido]-3-[(RS)-tetrahydrofuran-2-yl]-1-carba-1-dethiaceph-3-em-4-carboxylate (140 mg, 0.25 mmol) in dichloromethane (10 ml) was added to a solution of aluminium chloride (101 mg, 0.76 mmol) in anisole (4.5 ml) and dichloromethane (2.5 ml) as described in Example 7(b). After quenching with trisodium citrate (0.5M, 8 ml) and subsequent work-up, the product was purified by chromatography on HP20SS eluting with water, then 1 and 2% THF in water. Fractions containing the product (h.p.l.c. analysis) were combined and freeze-dried to give the title compound (54 mg, 47%); $v_{max}$ (KBr) 1746, 1662, 1596, 1532 and 1387 cm$^{-1}$; $\delta_H$ (d$_6$-DMSO, 250 MHz) 1.42–1.62 (2H,m), 1.68–1.88 (4H,m), 2.01 (1H,m), 2.27 (1H,m), 3.56–3.78 (3H,m), 3.85 (3H,s), 5.20 (2H,m), 6.75 (1H,s), 7.24 (2H,br s, exch.) and 9.25 (1H,d, J 8.7 Hz). [Mass spectrum: +ve ion (thioglycerol) MH$^+$ (458)].

EXAMPLE 25
Sodium (6R,7R)-7-[2-(2-Aminothiazol-4-yl)-2-(Z)-methoxy-iminoacetamido]-3-[(S)-tetrahydrofuran-2-yl]ceph-3-em-4-carboxylate-1,1-dioxide (a) 4-Methoxybenzyl (6R,7R)-7-[2-(2-aminothiazol-4-yl)-2-(Z)-methoxyiminoacetamido]-3-[(S)-tetrahydrofuran-2-yl]-ceph-3-em-4-carboxylate-1,1-dioxide To an ice-cooled solution of 4-methoxybenzyl (6R,7R)-7-[2-(2-aminothiazol-4-yl)-2-(Z)-methoxyiminoacetamido]-3-[(S)-tetrahydrofuran-2-yl]ceph-3-em-4-carboxylate (see Example 7) (300 mg, 0.52 mmol) in ethyl acetate (40 ml) was added a solution of m-chloroperbenzoic acid (270 mg, 1.56 mmol) in ethyl acetate (10 ml). The solution was stirred at room temperature for 1 h and was then washed with dilute aqueous sodium hydrogen carbonate and water, dried (magnesium sulphate) and evaporated under reduced pressure. The residue was chromatographed on silica gel eluting with ethyl acetate-hexane mixtures to give the title compound as a cream coloured solid (50 mg, 15%); $v_{max}$ (CHCl$_3$) 1810, 1730 and 1690 cm$^{-1}$; $\delta_H$ (CDCl$_3$) 1.52–1.70 (1H, m), 1.94–2.00 (2H, m), 2.41–2.48 (1H, m), 3.55 and 3.85 (2H, ABq, J 19 Hz), 3.19 (3H, s), 3.3–3.43 (2H, m), 4.1 (3H, s), 4.90 (1H, d, J 5 Hz), 4.97 (1H, t, J 7 Hz), 5.20 (2H, s), 5.94–6.3 (2H, m, exch.), 6.20 (1H, dd, J 5, 10 Hz), 6.91 (2H, d, J 8 Hz), 7.06 (1H, s), 7.32 (2H, d, J 8 Hz) and 7.86 (1H, d, J 10 Hz, exch). [Mass spectrum: +ve ion (thioglycerol) MH$^+$ (606)].

(b) Sodium (6R,7R)-7-[2-(2-Aminothiazol-4-yl)-2-(Z)-methoxyiminoacetamido]-3-[(S)-tetrahydrofuran-2-yl]ceph-3-em-4-carboxylate-1,1-dioxide The product from Example 25(a) was treated by the method of Example 23(b) to give the title compound (51%) as a freeze-dried white solid; $v_{max}$ (KBr) 1783, 1675 and 1610 cm$^{-1}$; $\delta_H$ (d$_6$-DMSO) 1.45–1.50 (1H, m), 1.69–1.79 (2H, m), 2.00–2.11 (1H, m), 3.48 and 3.87 (2H, ABq, J 18 Hz), 3.76 (3H, s), 3.50–3.86 (2H, m), 4.85 (1H, t, J 7 Hz), 5.22 (H, d, J 5 Hz), 5.61 (1H, dd, J 5, 7 Hz), 6.79 (1H, s), 7.13 (2H, s, exch.) and 9.33 (1H, d, J 7 Hz exch.). [Mass spectrum: +ve ion (thioglycerol) MH$^+$ (508)].

EXAMPLE 26
(RS)-1-(Propan-2-yl)oxycarbonyloxyethyl (6R,7R)-7-[2-(2-aminothiazol-4-yl)-2-(Z)-methoxyiminoacetamido]-3-[(S)-tetrahydrofuran-2-yl]ceph-3-em-4-carboxylate A solution of (RS)-1-iodo-1-(propan-2-yl)oxycarbonyloxyethane (516 mg) in 1-methyl-2-pyrrolidinone (2 ml) was added dropwise over 45 mins to an ice-cold mixture of sodium (6R,7R)-7-[2-(2-aminothiazol-4-yl)-2-(Z)-methoxyiminoacetamido]-3-[(S)-tetrahydrofuran-2-yl]ceph-3-em-4-carboxylate (237 mg) and finely powdered potassium carbonate (276 mg) in 1-methyl-2-pyrrolidinone (5 ml). The mixture was stirred for an additional 15 mins, diluted with ethyl acetate, washed with water, brine, dried (magnesium sulphate), concentrated and flash chromatographed on silica gel eluting with 50, 60, 70, 80% ethyl acetate in hexane to give the title compound as a foam (58 mg); $v_{max}$ (CHCl$_3$) 2960, 1787, 1760, 1682, 1633, 1519 and 1377 cm$^{-1}$; $\delta$ (CDCl$_3$, 250 MHz) 1.20–2.50 (13H, m), 3.35–3.80 (2H, m), 3.80–4.20 (2H, m), 4.22 (3H, s), 4.83–5.10 (2H, m), 5.85–6.00 (1H, m), 6.85–7.08 (1H, m), 7.27 (1H, s) and 7.76 (1H, br, m). [Mass spectrum: +ve ion (3-nitrobenzyl alcohol, sodium acetate) MNa$^+$ (606)].

EXAMPLE 27
Sodium (6R,7R)-7-[2-(2-aminothiazol-4-yl)-2-(Z)-methoxy-iminoacetamido]-3-[(5R,2SR)-5-methyltetrahydrofuran-2-yl]ceph-3-em-4-carboxylate (a) Methyl 5-methyl-2-furoate A solution of methyl 5-chloromethyl-2-furoate (5.0 g, 28.7 mmol) in ethyl acetate (40 ml) was hydrogenated over 10% palladium on charcoal (50 mg) for 3 h. The catalyst was filtered off and washed with ethyl acetate. The combined filtrates were concentrated in vacuo and the residue purified by chromatography on silica gel eluting with 10% ethyl acetate in hexane to yield the title compound as a colourless oil (3.78 g, 94%); $v_{max}$ (CH$_2$Cl$_2$) 1725, 1534, 1522, 1437 and 1311 cm$^{-1}$; $\delta_H$ CDCl$_3$, 90 MHz) 2.38 (3H, s), 3.86 (3H, s), 6.12 (1H, br d, J 4 Hz) and 7.07 (1H, d, J 4 Hz). [Mass spectrum: M$^+$ (140)].

(b) 5-Methyl-2-furoic acid

Methyl 5-methyl-2-furoate (3.68 g, 26.29 mmol) in methanol (30 ml) was treated with a solution of potassium hydroxide (2.80 g, 50.0 mmol) in water (15 ml) and the mixture stirred for 2 h at room temperature. The methanol was evaporated in vacuo, the residue dissolved in water and washed with ethyl acetate. The aqueous phase was acidified with 5N hydrochloric acid, and the product extracted with ethyl acetate (×3). The combined organic solutions were dried and concentrated to yield the title compound as a yellow solid (3.12 g, 94%); m.p. 110–112° C.; (Found: M$^+$, 126.0312. C$_6$H$_6$O$_3$ requires M$^+$ 126.0317); $\nu_{max}$ (CH$_2$Cl$_2$) 3300–2700, 1688, 1524, 1424, 1305, 1210 and 1167 cm$^{-1}$; $\delta_H$ (CDCl$_3$, 90 MHz) 2.40 (3H, s), 6.15 (1H, d, J 4 Hz) and 7.22 (1H, d, J 4 Hz).

(c) 5-Methyl-2-tetrahydrofuroic acid

A solution of 5-methyl-2-furoic acid (3.65 g, 28.97 mmol) in ethyl acetate (60 ml) was hydrogenated over 5% rhodium on carbon (250 mg) until hydrogen uptake ceased. The catalyst was filtered off and washed with ethyl acetate. The combined filtrates were concentrated in vacuo to yield the title compound as a pale yellow oil (3.67 g, 97%); $\nu_{max}$ (CH$_2$Cl$_2$) 3384, 3359, 1775, 1724 and 1355 cm$^{-1}$; $\delta_H$ (CDCl$_3$, 250 MHz) 1.35 (3H, d, J 6.1 Hz), 1.53 (1H, m), 2.09 (1H, m), 2.17–2.40 (2H, m), 4.21 (1H, m) and 4.46 (1H, dd, J 8.9, 4.7 Hz). [Mass spectrum: +ve ion (ammonia) MNH$_4^+$ (148)].

(d) 2-Bromoacetyl-5-methyltetrahydrofuran

A solution of 5-methyl-2-tetrahydrofuroic acid (1.80 g, 13.85 mmol) in dichloromethane (25 ml) was treated with oxalyl chloride (2.4 ml, 27.51 mmol) in the presence of dimethylformamide (3 drops). After stirring for 1.25 h, the solvent was evaporated in vacuo. The residue was redissolved in dichloromethane and concentrated again. Excess diazomethane was then bubbled through a solution of the resulting acid chloride in dichloromethane (30 ml) at 0° C. When the addition was complete, the mixture was stirred for 10 min. at 0° C. and then treated with 48% aqueous hydrogen bromide (2.6 ml, 15.41 mmol). The mixture was stirred for 15 min. at room temperature, washed with water (×2), dried and concentrated in vacuo to yield the crude title compound as a brown oil (1.67 g, 58%); $\nu_{max}$ (CH$_2$Cl$_2$) 1735, 1387 and 1086 cm$^{-1}$; $\delta_H$ (CDCl$_3$, 90 MHz) 1.33 (3H, d, J 6.0 Hz), 1.48 (1H, m), 1.90–2.35 (3H, m), 4.10 (1H, m), 4.25 (2H, s) and 4.48 (1H, m).

(e) 4-Methoxybenzyl (2RS)-2-hydroxy-2-[(3R,4R)-4-(5-methyltetrphydrofuran-2-ylcarbonylmethylthio)-3-thenylacetamidoazetidin-2-on-1-yl]acetate Toluene-4-sulphonic acid (3.42 g, 17.98 mmol) in water (8 ml) was added to a solution of 4-methoxybenzyl (2RS)-2-hydroxy-2-[(1R,5R)-3-benzyl-4-thia-2,6-diazabicyclo[3.2.0]hept-2-en-7-on-6-yl]acetate (4.12 g, 10.0 mmol) in dichloromethane (20 ml) and acetone (20 ml). After stirring for 2.5 h at room temperature, the reaction mixture was diluted with dichloromethane, washed with water (×2), dried and concentrated in vacuo to yield crude 4-methoxybenzyl (2RS)-2-hydroxy-2-[(3R,4R)-4-mercapto-3-phenylacetamidoazetidin-2-on-1-yl]acetate as a colourless foam. The crude thiol was dissolved in acetone (50 ml) and treated with a solution of 2-bromoacetyl-5-methyltetrahydrofuran (1.67 g, 8.1 mmol) in acetone (5 ml). After 10 min., potassium carbonate (687 mg, 5.0 mmol) was added, and the mixture stirred for a further 30 min. The reaction mixture was diluted with ethyl acetate, washed successively with water (×2) and brine, dried and concentrated. The residue was purified by chromatography on silica gel eluting with 50, 70 and 80% ethyl acetate in hexane to yield the title compound as a colourless foam (2.68 g, 60%); $\nu_{max}$ (CH$_2$Cl$_2$) 3412, 1781, 1744, 1685 and 1515 cm$^{-1}$. [Mass spectrum: +ve ion (3-nitrobenzyl alcohol, sodium acetate) MNa$^+$ (579)].

(f) 4-Methoxybenzyl 2-[(3R,4R)-4-(5-methyltetrahydrofuran-2-ylcarbonylmethylthio)-3-phenylacetamidoazetidin-2-on-1-yl]-2-tri-n-butylphosphoranylideneacetate A solution of thionyl chloride (530 μl, 7.27 mmol) in tetrahydrofuran (5 ml) was added dropwise to the hydroxy compound (2.68 g, 4.85 mmol) and 2,6-lutidine (850 μl, 7.29 mmol) in tetrahydrofuran (30 ml) at −20° C. After stirring for 30 min. the reaction mixture was filtered through a pad of celite and the filtrate concentrated in vacuo. Toluene was added and re-evaporated to yield 4-methoxybenzyl (RS)-2-chloro-2-[(3R,4R)-4-(5-methyl-tetrahydrofuran-2-ylcarbonylmethylthio)-3-phenyl-acetamido-azetidin-2-on-1-yl]acetate. The crude chloro-compound was dissolved in dioxan (40 ml) and treated with tri-n-butylphosphine (2.7 ml, 10.84 mmol). After stirring for 30 min. at room temperature, the reaction mixture was diluted with ethyl acetate and washed successively with dilute sodium hydrogen carbonate solution, water and brine. The organic solution was dried, concentrated and then purified by chromatography on silica gel eluting with 50, 70 and 100% ethyl acetate in hexane to yield the title compound as a yellow foam (2.28 g, 64%); $\nu_{max}$ (CH$_2$Cl$_2$) 3420, 1762, 1732, 1681 and 1515 cm$^{-1}$. [Mass spectrum: +ve ion (3-nitrobenzyl alcohol, sodium acetate) MH$^+$ 741, MNa$^+$ 763].

(g) 4-Methoxybenzyl (6R,7R)-3-(5-methyltetrahydrofuran-2-yl)-7-phenylacetamidoceph-3-em-4-carboxylate A solution of the phosphorane (2.28 g, 3.08 mmol) and benzoic acid (10 mg) in toluene (40 ml) was heated in an oil bath at 130° C. for 16 h under argon. The reaction mixture was cooled, concentrated and the residue purified by chromatography on silica gel eluting with 10, 20 and 40% ethyl acetate in hexane yielding a mixture of the title compound and some of the Δ2 isomer as a yellow oil (1.27 g, 79%); (Found: M$^+$, 522.1813. C$_{28}$H$_{30}$N$_2$O$_6$S$_2$ requires M$^+$ 522.1825); $\nu_{max}$ (CH$_2$Cl$_2$) 3416, 1782, 1729, 1688, 1613 and 1515 cm$^{-1}$.

(h) 4-Methoxybenzyl (6R,7R)-7-amino-3-(5-methyltetrahydrofuran-2-yl)ceph-3-em-4-carboxylate Phosphorus pentachloride (754 mg, 3.62 mmol) in dichloromethane (19 ml) was added to 4-methoxybenzyl (6R,7R)-3-(5-methyltetrahydrofuran-2-yl)-7-phenylacetamidoceph-3-em- 4-carboxylate (containing some of the Δ2-isomer) (1.26 g, 2.41 mmol) and N-methylmorpholine (531 μl, 4.83 mmol) in dichloromethane (15 ml) at −25° C. The reaction was stirred at −10±5° C. for 45 min., then methanol (5 ml) was added, and stirring was continued for 45 min. at room temperature. Water (10 ml) was then added, and the mixture vigorously stirred for a further 1 h. After evaporation of the dichloromethane in vacuo, the pH of the aqueous residue was adjusted to 7 by the addition of ammonium hydroxide in the presence of ethyl acetate. The mixture was extracted with ethyl acetate (×2), dried and concentrated in vacuo. The residue was purified by chromatography on silica gel eluting with 30, 50, 70, 80 and 100% ethyl acetate in hexane yielding 4-methoxybenzyl (6R,7R)-7-amino-3-[(5S,2S)-5-methyltetrahydrofuran-2-yl]ceph-3-em-4-carboxylate (310 mg, 32%) as a pale yellow foam; (Found: M$^+$, 404.1394. C$_{20}$H$_{24}$N$_2$O$_5$S requires M$^+$ 404.1406); $\nu_{max}$ (CH$_2$Cl$_2$) 3412, 1776, 1721, 1613, 1516 and 1393 cm$^{-1}$; $\delta_H$ (CDCl$_3$, 250 MHz), 1.24 (3H, d, J 5.8 Hz), 1.48 (1H, m), 1.69 (1H, m), 2.02 (3H, m, 2H exch.), 2.25 (1H, m), 3.45 and 3.60 (2H, ABq, J 17.7 Hz), 3.78 (3H, s), 3.98 (1H, m), 4.88 (1H, d, J 5.0 Hz), 4.93–5.04 (2H, m), 5.17 (2H, s), 6.87 (2H, d, J 8.6 Hz), 7.32 (2H, d, J 8.6 Hz).

Further elution of the column with ethyl acetate yielded the more polar diastereoisomer 4-methoxybenzyl (6R,7R)-

7-amino-3-[(5R,2R)-5-methyltetrahydrofuran-2-yl]ceph-3-em-4-carboxylate (208 mg, 21%) as a yellow foam; (Found: M$^+$ 404.1402. C$_{20}$H$_{24}$N$_2$O$_5$S requires M$^+$ 404.1406); $v_{max}$ (CH$_2$Cl$_2$) 3411, 1776, 1727, 1613 and 1516 cm$^{-1}$; $\delta_H$ CDCl$_3$, 250 MHz), 1.24 (3H, d, J 6.1 Hz), 1.48 (1H, m), 1.69 (1H, m), 1.92–2.08 (2H, m), 3.47 and 3.71 (2H, ABq, J 17.8 Hz), 3.79 (3H, s), 4.00 (1H, dd, J 12.9, 6.4 Hz), 4.83 (1H, d, J 4.8 Hz), 4.92–5.17 (4H, m, 2H exch.), 5.19 (2H, s), 6.88 (2H, d, J 8.6 Hz) and 7.32 (2H, d, J 8.6 Hz).

Further elution of the column yielded the Δ2-cephems (142 mg, 15%).

(i) 4-Methoxybenzyl (6R,7R)-7-[2-(2-aminothiazol-4-yl)-2-(Z)-methoxyiminoacetamido]-3-[(5S,2S)-5-methyltetrahydrofuran-2-yl]ceph-3-em-4-carboxylate 2-(2-Aminothaizol-4-yl)-2-(Z)-methoxyiminoacetic acid (167 mg, 0.83 mmol) in DMF (5 ml) was treated with methanesulphonyl chloride (64 μl, 0.83 mmol) and N,N-diisopropylethylamine (145 μl, 0.83 mmol) as described in Example 7(a). This was then treated successively with a solution of 4-methoxybenzyl (6R,7R)-7-amino-3-[(5S,2S)-5-methyltetrahydrofuran-2-yl]ceph-3-em-4-carboxylate (305 mg, 0.75 mmol) in DMF (5 ml) and pyridine (679 μl, 0.83 mmol). After work-up the product was purified by chromatography on silica gel eluting with 50, 70 and 100% ethyl acetate in hexane to yield the title compound as a yellow foam (373 mg, 85%); $v_{max}$ (CH$_2$Cl$_2$) 3389, 1784, 1724, 1689, 1606 and 1516 cm$^{-1}$; $\delta_H$ (CDCl$_3$, 400 MHz) 1.29 (3H, d, J 5.9 Hz), 1.48 (1H, m), 1.69 (1H, m), 1.93 (2H, br s, exch.), 2.07 (1H, m), 2.29 (1H, m), 3.39 and 3.64 (2H, ABq, J 18.8 Hz), 3.80 (3H, s), 4.00 (1H, dd, J 12.8, 6.4 Hz), 4.10 (3H, s), 4.96 (1H, dd, J 7.7, 7.7 Hz), 5.02 (1H, d, J 4.8 Hz), 5.19 (2H, s), 5.84 (1H, br s, exch.), 5.94 (1H, dd, J 9.0, 4.8 Hz), 6.89 (2H, d, J 8.5 Hz) and 7.02 (1H, s), 7.35 (2H, d, J 8.5 Hz). [Mass spectrum: +ve ion (ammonia) MH$^+$ (588)].

(j) 4-Methoxybenzyl (6R,7R)-7-[2-(2-aminothiazol-4-yl)-2-(Z)-methoxyiminoacetamido]-3-[(5R,2R)-5-methyltetrahydro-furan-2-yl]ceph-3-em-4-carboxylate 2-(2-Aminothaizol-4-yl)-2-(Z)-methoxyiminoacetic acid (109 mg, 0.54 mmol) in DMF (3 ml) was treated with methanesulphonyl chloride (42 μl, 0.54 mmol) and N,N-diisopropylethylamine (95 μl, 0.55 mmol) as described in Example 7(a). This was then treated successively with a solution of 4-methoxybenzyl (6R,7R)-7-amino-3-[(5R,2R)-5-methyltetrahydrofuran-2-yl]ceph-3-em-4-carboxylate (200 mg, 0.50 mmol) in DMF (10 ml) and pyridine (44 μl, 0.54 mmol).

After work-up, the product was purified by triturating with diethyl ether to yield the title compound (214 mg, 73%); $v_{max}$ (CH$_2$Cl$_2$) 3388, 1784, 1726, 1688, 1606 and 1516 cm$^{-1}$; $\delta_H$ (CDCl$_3$, 400 MHz) 1.26 (3H, d, J 6.0 Hz), 1.46 (1H, m), 1.66 (1H, m), 1.87 (2H, br s, exch.), 2.00 (2H, m), 3.43 and 3.67 (2H, ABq, J 18.0 Hz), 3.81 (3H, s), 4.00 (1H, dd, J 13.3, 6.3 Hz), 4.09 (3H, s), 5.04 (1H, d, J 4.8 Hz), 5.15–5.25 (3H, m), 5.55 (1H, br s, exch.), 5.89 (1H, dd, J 8.8, 4.8 Hz), 6.90 (2H, d, J 8.6 Hz), 6.98 (1H, s) and 7.34 (2H, d, J 8.6 Hz). [Mass spectrum: +ve ion (ammonia) MH$^+$ (588)].

(k) Sodium (6R,7R)-7-[2-(2-aminothiazol-4-yl)-2-(Z)-methoxyiminoacetamido]-3-[(5S,2S)-5-methyltetrahydrofuran-2-yl]ceph-3-em-4-carboxylate A solution of 4-methoxybenzyl (6R,7R)-7-[2-(2-aminothiazol-4-yl)-2-(Z)-methoxyiminoacetamido]-3-[(5S,2S)-5-methyltetrahydrofuran-2-yl]ceph-3-em-4-carboxylate (370 mg, 0.63 mmol) in dichloromethane (10 ml) was added to a solution of aluminium chloride (252 mg, 1.89 mmol) in anisole (10 ml) and dichloromethane (5 ml) as described in Example 7(b). After quenching with trisodium citrate (0.5M, 20 ml) and subsequent work-up, the product was purified by chromatography on HP20SS eluting with water, then 1, 2, 3 and 4% THF in water. Fractions containing the product (h.p.l.c. analysis) were combined and freeze-dried to give the title compound (240 mg, 78%); $v_{max}$ (KBr) 1762, 1670, 1602, 1532 and 1390 cm$^{-1}$; $\delta_H$ d$_6$-DMSO, 250 MHz) 1.15 (3H, d, J 6.0 Hz), 1.41 (1H, m), 1.59 (1H, m), 1.85–2.08 (2H, m), 3.26 and 3.42 (2H, ABq, J 17.7 Hz), 3.85 (3H, s), 3.87 (1H, m), 4.87 (1H, dd, J 7.3, 7.3 Hz), 5.00 (1H, d, J 4.7 Hz), 5.57 (1H, dd, J 8.0, 4.7 Hz), 6.74 (1H, s), 7.22 (2H, s, exch.) and 9.51 (1H, d, J 8.0 Hz, exch.). [Mass spectrum: +ve ion (thioglycerol) MH$^+$ (490)].

(1) Sodium (6R,7R)-7-[2-(2-aminothiazol)-4-yl)-2-(Z)-methoxyiminoacetamido]-3-[(5R,2SR)-5-methyltetrahydrofuran-2-yl]ceph-3-em-4-carboxylate 4-Methoxybenzyl (6R,7R)-7-[2-(2-aminothiazol-4-yl)-2-(Z)-methoxyiminoacetamido]-3-[5R,2R)-5-methyltetrahydrofuran-2-yl]ceph-3-em-4-carboxylate (210 mg, 0.36 mmol) in 0.1M hydrochloric acid in 90% formic acid (3.6 ml) was allowed to stand for 1 h. Concentrated hydrochloric acid (2 drops) was then added, and the mixture left for a further 2.5 h. After evaporating to dryness in vacuo, the residue was dissolved in water, the pH adjusted to 6.5 by addition of 1M sodium hydroxide solution and chromatographed on HP20SS eluting with 0, 1, 2, 3 and 4% THF in water. Fractions containing the product (h.p.l.c. analysis) were combined, concentrated and freeze-dried to give the title compound as a mixture of diastereoisomers (121 mg, 69%); $v_{max}$ (KBr) 1763, 1663, 1598 and 1388 cm$^{-1}$; $\delta_H$ (d$_6$-DMSO, 250 MHz) 1.10 and 1.16 (together 3H, 2d, J 6.0 Hz), 1.27–2.17 (4H, m), 3.15–3.45 (together 2H, 2ABq), 3.84 (3H, s), 4.09 (1H, m), 4.93 and 4.95 (together 1H, 2d, J 4.6 Hz), 5.02 and 5.18 (together 1H, 2dd, J 9.4, 5.9 and 7.6, 7.6 Hz), 5.50 (1H, m), 6.74 and 6.76 (together 1H, 2s), 7.22 (2H, s, exch.) and 9.47 and 9.52 (together 1H, 2d, J 8.4 Hz, exch.). [Mass spectrum: +ve ion (thioglycerol) MH$^+$ (490)].

EXAMPLE 28

Sodium (6R,7R)-7-[(furan-2-yl]-2-(Z)-methoxyiminoacetamido)-3-[(S)-tetrahydrofuran-2-yl]ceph-3-em-4-carboxylate (a) 4-Methoxybenzyl (6R,7R)-7-[2-(furan-2-yl)-2-(Z)-methoxyiminoacetamido]-3-[(S)-tetrahydrofuran-2-yl]ceph-3-em-4-carboxylate 2-(Furan-2-yl)-2-(Z)-methoxyiminoacetic acid (90 mg) in dry DMF (4 ml) was treated with N,N-diisopropylethylamine (0.1 ml), cooled to −35° C., and treated with methanesulphonyl chloride (0.044 ml) and the mixture stirred at −35° C. for 30 min.

A solution of the 4-methoxybenzyl (6R,7R)-7-amino-3-[(S)-tetrahydrofuran-2-yl]ceph-3-em-4-carboxylate (195 mg) in dry DMF (3 ml) was added followed by pyridine (0.044 ml) and the mixture stirred at ice-bath temperature for a further 1 h. The solution was diluted with excess ethyl acetate and the organic solution washed successively with 5% aqueous citric acid, saturated aqueous sodium bicarbonate solution and finally brine. After drying over anhydrous magnesium sulphate the solvent was evaporated. Chromatography of the residue on silica gel using ethyl acetate-hexane (1:1) as eluent gave the title compound as a pale yellow foam (190 mg, 73%); $v_{max}$ 3400, 1785, 1725 and 1690 cm$^{-1}$. [Mass spectrum: +ve ion (thioglycerol) MH$^+$ (542)].

(b) Sodium (6R,7R)-7-[2-furan-2-yl)-2-(Z)-methoxyimino-acetamido]-3-[(S)-tetrahydrofuran-2-yl]ceph-3-em-4-carboxylate Aluminium trichloride (130 mg) was added to a solution of anisole (6 ml) and dichloromethane (4 ml) at −25° C. and the mixture stirred at −25° C. for 15 min. The mixture was then cooled to −40° C., a solution of the product of Example 28(a) (180 mg) in dichloromethane (4 ml) added in one portion and stirred at −40° for 20 min. The cooling bath was removed, trisodium citrate (10 ml of an aqueous 0.5M solution) added and the mixture stirred vigorously for 20 min. The aqueous layer was separated, washed twice with dichloromethane and concentrated under reduced pressure. The residue was chromatographed on HP20SS eluting with water-acetone mixtures. Fractions containing the product (t.l.c.; h.p.l.c. analysis) were combined, concentrated and freeze-dried to give the title compound as a white solid (95 mg, 66%); $\mu_{max}$ (KBr) 1770, 1685 and 1600 cm$^{-1}$; $\delta_{(H)}$ (D$_2$O) 1.65–1.85 (1H, m), 1.9–2.05 (2H, m), 2.08–2.15 (1H, m), 3.33 and 3.53 (2H, ABq, J 18 Hz), 3.75–4.0 (2H, m), 3.96 (3H, s), 4.71 (1H, dd, J 8.3,6.9 Hz), 5.2 (1H, d, J 4.5 Hz), 5.73 (H, d, J 4.5 Hz), 6.58 (1H, dd), 6.86 (1H, d) and 7.64 (1H, d).

EXAMPLE 29

Sodium (6R,7R)-7-[2-(2-aminothiazol)-2-(Z)-methoxyimino-acetamido]-3-[(S)-5,5-dimethyltetrahydrofuran-2-yl]ceph-3-em-4-carboxylate (a) (S)-2-Bromoacetyl-5,5-dimethyltetrahydrofuran A solution of (S)-5,5-dimethyltetrahydrofuran-2-carboxylic acid (800 mg, 5.56 mmol) (I. Kitagawa, T. Nishino, M. Kobayashi, T. Matsuno, H. Akutsu and Y. Kyagaku, *Chem. Pharm. Bull.*, 1981, 29, 1942) in dichloromethane (25 ml) was treated with oxalyl chloride (2.4 ml, 27.51 mmol) and dimethylformamide (3 drops). The mixture was stirred for 1 h, evaporated in vacuo, dichloromethane added, and re-evaporated. The resulting acid chloride was dissolved in dichloromethane (25 ml) and cooled in an ice-bath. Diazomethane was then passed into the solution as described in Example 14(a). When the addition was complete, 48% aqueous hydrogen bromide (2.6 ml) was added, and the mixture stirred for a further 10 min. The solution was washed with water (×2), dried over MgSO$_4$ and concentrated in vacuo to yield the title compound as an orange oil (812 mg, 66%); $\nu_{max}$ (CH$_2$Cl$_2$) 1767 cm$^{-1}$; $\delta_H$ (CDCl$_3$, 250 MHz) 1.28 (3H, s), 1.32 (3H, s), 1.78–2.68 (4H, m), 4.27 (2H, s) and 4.56 (1H, dd, J 8.2, 6.8 Hz).

(b) 4-Methoxybenzyl (2RS)-2-Hydroxy-2-[(3R,4R)-4-[(S)-5,5-dimethyltetrahydrofuran-2-ylcarbonylmethylthio]-3-phenylacetamidoazetidin-2-on-1-yl]acetate 4-Methoxybenzyl (RS)-2-hydroxy-2-[(1R,5R)-3-benzyl-4-thia-2,6-diazabicyclo[3.2.0]hept-2-en-7-on-6-yl]acetate (3.3 g, 8.0 mmol) in 50% acetone/dichloromethane (32 ml) was cleaved with 4-toluenesulphonic acid (2.74 g, 14.4 mmol) in water (6 ml). This product was reacted with the crude bromide from Example 29(a) (808 mg, 3.66 mmol) in acetone (40 ml) with potassium carbonate (550 mg, 3.99 mmol) as described in Example 6(b). After work-up, the residue was purified by chromatography on silica gel eluting with 50, 70 and 90% ethyl acetate in hexane to yield the title compound (1.25 g, 60%) as a yellow oil; $\nu_{max}$ (CH$_2$Cl$_2$) 3410, 1780, 1746, 1683, 1613 and 1515 cm$^{-1}$. [Mass spectrum: +ve ion (3-nitrobenzyl alcohol, sodium acetate) MNa$^+$ (593)].

(c) 4-Methoxybenzyl 2-[(3R,4R)-4-[(S)-5,5-dimethyltetrahydrofuran-2-ylcarbonylmethylthio]-3-phenylacetamidoazetidin-2-on-1-yl]-2-tri-n-butylphosphoranylideneacetate The alcohol from Example 29(b) (1.25 g, 2.19 mmol) was treated with thionyl chloride (240 μl, 3.29 mmol) and 2,6-lutidine (383 μl, 3.29 mmol), followed by tri-n-butylphosphine (1.20 ml, 4.82 mmol) as described for Example 6(c). The product was purified by chromatography on silica gel eluting with 50, 70 and 100% ethyl acetate in hexane to yield the title compound (617 mg, 37%) as a yellow foam; $\nu_{max}$ (CH$_2$Cl$_2$) 1763, 1680, 1608 and 1515 cm$^{-1}$. [Mass spectrum: M$^+$ (754)].

(d) 4-Methoxybenzyl (6R,7R)-3-[(S)-5,5-dimethyltetrahydro-furan-2-yl]-7-phenylacetamidoceph-3-em-4-carboxylate A solution of the phosphorane from Example 29(c) (610 mg, 0.81 mmol) and benzoic acid (10 mg) in toluene (20 ml) was heated at reflux for 16 h. After cooling, the solvent was evaporated in vacuo. The residue was purified by chromatography on silica gel eluting with 5 and 10% ethyl acetate in dichloromethane yielding the title compound as a yellow foam (240 mg, 55%); (Found: M$^+$, 536.1978. C$_{29}$H$_{32}$N$_2$O$_6$S requires M$^+$ 536.1981); $\nu_{max}$ (CH$_2$Cl$_2$) 3415, 1784, 1723, 1684 and 1515 cm$^{-1}$; $\delta_H$ (CDCl$_3$, 250 MHz) 1.22 (3H, s), 1.27 (3H, s), 1.62–1.81 (3H, m), 2.28 (1H, m), 3.30 and 3.56 (2H, ABq, J 18.8 Hz), 3.60 and 3.69 (2H, ABq, J 16.3 Hz), 3.82 (3H, s), 4.88 (1H, d, J 4.8 Hz), 5.00 (1H, dd, J 8.6, 6.1 Hz), 5.11 and 5.21 (2H, ABq, J 11.8 Hz), 5.80 (1H, dd, J 9.1, 4.8 Hz), 5.96 (1H, br d, J 9.1 Hz, exch.), 6.88 (2H, d, J 8.7 Hz) and 7.24–7.40 (7H, m).

(e) 4-Methoxybenzyl (6R,7R)-7-amino-3-[(S)-5,5-dimethyltetrahydrofuran-2-yl]ceph-3-em-4-carboxylate Phosphorus pentachloride (48 mg, 0.23 mmol) in dichloromethane (1.2 ml) was added to 4-methoxybenzyl (6R,7R)-3-[(S)-5,5-dimethyltetrahydrofuran-2-yl]-7-phenylacetamidoceph-3-em-4-carboxylate (93 mg, 0.15 mmol) and N-methylmorpholine (34 μl, 0.31 mmol) in dichloromethane (3 ml) at −25° C. The reaction was stirred at −10+5° C. for 45 min., then methanol (0.5 ml) was added, and stirring continued for 45 min. at room temperature. Water (1 ml) was then added, and the mixture vigorously stirred for a further 1 h. After evaporation of the dichloromethane in vacuo, the pH of the aqueous residue was adjusted to 7 by the addition of ammonium hydroxide in the presence of ethyl acetate. The mixture was extracted with ethyl acetate (×2), dried and concentrated in vacuo. The residue was purified by chromatography on silica gel eluting with 70% ethyl acetate in hexane yielding the title compound (25 mg, 39%); (Found: M$^+$ 418.1566. C$_{21}$H$_{26}$N$_2$O$_5$S requires M$^+$ 418.1562); $\nu_{max}$ (CH$_2$Cl$_2$) 2970, 1777, 1721, 1613 and 1516 cm$^{-1}$; $\delta_H$ (CDCl$_3$, 250 MHz) 1.21 (3H, s), 1.27 (3H, s), 1.68–1.81 (3H, m), 2.25 (1H, m), 3.48 and 3.62 (2H, ABq, J 18.7 Hz), 3.56 (2H, br s, exch.), 3.79 (3H, s), 4.73–5.25 (5H, m), 6.87 (2H, d, J 8.6 Hz) and 7.30 (2H, d, J 8.6 Hz).

(f) 4-Methoxybenzyl (6R,7R)-7-[2-(2-aminothiazol-4-yl)-2-(Z)-methoxyiminoacetamido]-3-[(S)-5,5-dimethyltetrahydrofuran-2-yl]ceph-3-em-4-carboxylate 2-(2-Aminothiazol-4-yl)-2-(Z)-methoxyiminoacetic acid (13 mg, 0.065 mmol) in DMF (2 ml) was treated with methanesulphonyl chloride (51 μl, 0.064 mmol) and N,N-diisopropylethylamine (11 μl, 0.063 mmol) as described in Example 7(a). This was then treated successively with a solution of the amine from Example 29(e) (25 mg, 0.060 mmol) in DMF (2 ml) and pyridine (5 μl, 0.062 mmol). After work-up the product was purified by chromatography on silica gel eluting with 50, 70 and 100% ethyl acetate in hexane to yield the title compound (25 mg, 70%) as a yellow foam; $\nu_{max}$ (CH$_2$Cl$_2$) 3389, 1784, 1722, 1690, 1607 and 1516 cm$^{-1}$; $\delta_H$ (CDCl$_3$, 250 MHz) 1.23 (3H, s), 1.29 (3H, s), 1.61–1.84 (3H, m), 2.31 (1H, m), 3.40 and 3.63 (2H, ABq, J 18.7 Hz), 3.81 (3H, s), 4.20 (3H, s), 4.99 (1H, d, J 4.8 Hz), 5.05 (1H, dd, J 8.1, 8.1 Hz), 5.13 and 5.23 (2H, ABq, J 11.8 Hz), 5.90 (1H, dd, J 8.9, 4.8 Hz), 6.90 (2H, d, J 8.7 Hz), 7.23 (1H, s), 7.34 (2H, d, J 8.7 Hz), 7.50 (2H, br s, exch.) and 7.68 (1H, br d, J 8.9 Hz, exch). [Mass spectrum: +ve ion (ammonia) MH$^+$ (602)].

(g) Sodium (6R,7R)-7-[2-(2-aminothiazol-4-yl)-2-(Z)-methoxyiminoacetamido]-3-[(S)-5,5-dimethyltetrahydrofuran-2-yl]ceph-3-em-4-carboxylate A solution of the ester from Example 29(f) (23 mg, 0.038 mmol) in dichloromethane (2 ml) was added to a solution of aluminium chloride (15 mg, 0.112 mmol) in anisole (0.6 ml) and dichloromethane (0.3 ml) as described in Example 7(b). After quenching with trisodium citrate (0.5M, 1.3 ml) and subsequent work-up, the product was purified by chromatography on HP20SS eluting with water, then 1, 2, 4 and 6% THF in water. Fractions containing the product (h.p.l.c. analysis) were combined and freeze-dried to give the title compound (13 mg, 68%); $v_{max}$ (KBr) 1762, 1664, 1605 and 1529 cm$^{-1}$; $\delta_H$ (d$_6$-DMSO, 250 MHz) 1.13 (3H, s), 1.19 (3H, s), 1.59–1.73 (3H, m), 2.04 (1H, m), 3.22 and 3.37 (2H, ABq, J 17.5 Hz), 3.83 (3H, s), 4.93 (1H, d, J 4.5 Hz), 5.00 (1H, dd, J 7.9 Hz), 5.52 (1H, dd, J 8.0, 4.5 Hz), 6.75 (1H, s), 7.23 (2H, br s, exch.) and 9.48 (1H, d, J 8.0 Hz, exch.). [Mass spectrum: +ve ion (3-nitrobenzyl alcohol, sodium acetate) MNa$^+$ (526)].

EXAMPLE 30

Sodium (6R,7R)-7-[2-(2-aminothiazol-4-yl)-2-(Z)-methoxy-iminoacetamido]-3-(5-methoxycarbonyltetrahydrofuran-2-yl)ceph-3-em-4-carboxylate (a) (2RS,5SR)-5-Methoxycarbonyltetrahydrofuran-2-yl carboxylic acid A mixture of furan-2,5-dicarboxylic acid monomethyl ester (1.95 g) and 5% rhodium on carbon (400 mg) in ethyl acetate (50 ml) was hydrogenated until hydrogen uptake ceased. The catalyst was filtered off and washed with ethyl acetate. The combined filtrates were evaporated to give (2.00 g) of the title compound: $v_{max}$ (film) 3170, 1765 and 1720 cm$^{-1}$; $\delta_H$ (CDCl$_3$) 1.95–2.65 (4H, m), 3.85 (3H, s) and 4.55–4.8 (2H, m).

(b) Methyl (2RS,5SR)-5-(2-chloroacetyl)tetrahydro-2-furoate

Oxalyl chloride (1.55 ml) was added to a stirred solution of (2RS,5SR)-5-methoxycarbonyltetrahydrofuran-2-ylcarboxylic acid (2.00 g) in dichloromethane (30 ml). Dimethylformamide (1 drop) was added and the mixture stirred at room temperature for 1 h, and then heated to reflux for 10 min. The mixture was cooled and the solvent removed on a rotary evaporator. Chloroform was then evaporated from the residue twice. The residue was dissolved in dichloromethane (100 ml) and the solution cooled in an ice bath, then excess diazomethane was passed into the solution. The mixture was stirred at 0° C. for 15 min and then excess hydrogen chloride was passed into the solution. The solution was washed with brine, dried over magnesium sulphate and evaporated. The title compound (2.02 g) was isolated by column chromatography of the residue using gradient elution (silica gel, 4:1 going to 1:1 hexane:ethyl acetate); $v_{max}$ (CHCl$_3$) 1740 cm$^{-1}$; $\delta_H$ (CDCl$_3$) 1.9–2.5 (4H, m), 3.71 (3H, s), 4.45–4.8 (2H, m), 4.54 (1H, d, J 18 Hz) and 4.89 (1H, d, J 18 Hz).

(c) (3R,4R)-4-[(2RS,5SR)-5-Methoxycarbonyltetrahydrofuran-2-ylcarbonylmethylthio)-3-phenylacetamidoazetidin-2-one Potassium carbonate (2.0 g) was added to a stirred solution of (3R,4R)-4-mercapto-3-phenylacetamidoazetidin-2-one (2.31 g) and methyl (2RS,5SR)-5-(2-chloroacetyl)tetrahydro-2-furoate (2.02 g) in dimethylformamide (30 ml). The mixture was stirred at room temperature for 1.5 h and then partitioned between ethyl acetate and water. The aqueous phase was separated and extracted with ethyl acetate. The combined organic phases were washed three times with water, then brine, dried over magnesium sulphate and evaporated. The title compound (2.208 g) was isolated by column chromatography of the residue (silica gel, ethyl acetate as eluent); $v_{max}$ (CHCl$_3$) 3410, 3335, 1777, 1736 and 1678 cm$^{-1}$.

(d) 4-Methoxybenzyl (RS)-2-hydroxy-2-[4-[(2RS,5SR)-5-methoxycarbonyltetrahydrofuran-2-ylcarbonylmethylthio)-3-phenylacetamidoazetidin-2-on-1-yl]acetate 4-Methoxybenzyl glyoxylate hydrate (1.50 g) in dichloroethane (30 ml) was heated at reflux for 1 h using a Dean and Stark apparatus for heavy entrainers. The mixture was cooled to room temperature and then a solution of (3R,4R)-4-[(2RS,5SR)-5-methoxycarbonyltetrahydrofuran-2-ylcarbonylmethylthio]-3-phenylacetamidoazetidin-2-one (2.208 g) in dichloroethane (20 ml) was added followed by triethylamine (0.1 ml). The mixture was stirred at room temperature for 1 h and then the solvents were evaporated. The title compound was obtained as a mixture of isomers (2.66 g) by column chromatography of the residue using gradient elution (silica gel, 1:1 hexane:ethyl acetate going to neat ethyl acetate); $v_{max}$ (CHCl$_3$) 3412, 1776, 1741 and 1681 cm$^{-1}$.

(e) 4-Methoxybenzyl 2-[(3R,4R)-4-[(2RS,5SR)-5-methoxy-carbonyltetrahydrofuran-2-ylcarbonylmethylthio]-3-phenylacetamidoazetidin-2-on-1-yl]-2-tri-n-butyl-phosphoranylideneacetate A solution of thionyl chloride (0.51 ml) in tetrahydrofuran (4 ml) was added to a stirred solution of 4-methoxybenzyl (RS)-2-hydroxy-2-[(2R,4R)-4-[(2RS,5SR)-5-methoxy-carbonyltetrahydrofuran-2-ylcarbonylmethylthio]-3-phenyl-acetamidoazetidin-2-on-1-yl]acetate (2.66 g) and 2,6-lutidine (0.825 ml) in tetrahydrofuran (21 ml). The mixture was stirred at room temperature for 2 h. The solid was filtered off and washed with tetrahydrofuran. The combined filtrates were evaporated and the residue was dissolved in toluene and the solvent evaporated. The residue was dissolved in dioxan (26 ml) under argon and then tri-n-butylphosphine (2.6 ml) was added. The mixture was stirred at room temperature for 0.5 h and then ethyl acetate was added and the solution washed successively with sodium bicarbonate solution, water and brine. The solution was dried over magnesium sulphate and evaporated. The title compound (1.00 g) was isolated by column chromatography of the residue using gradient elution (silica gel. 1:1, hexane:ethyl acetate, going to neat ethyl acetate); $v_{max}$ (CHCl$_3$) 3419, 1753, 1676 and 1612 cm$^{-1}$, (e) 4-Methoxybenzyl (6R,7R)-3-[(2RS,5SR)-5-methoxy-carbonyltetrahydrofuran-2-yl]-7-phenylacetamidoceph-3-em-4-carboxylate A solution of 4-methoxybenzyl 2-[(3R,4R)-4-[(2RS,5SR)-5-methoxy-carbonyltetrahydrofuran-2-ylcarbonylmethylthio]-3-phenylacetamidoazetidin-2-on-1-yl]-2-tri-n-butyl-phosphoranylideneacetate (1.00 g) in toluene (100 ml) was heated to reflux for 18 h. The solvent was evaporated and the title compound (497 mg) separated by column chromatography of the residue using gradient elution (silica gel, 1:1 hexane:ethyl acetate going to neat ethyl acetate); $v_{max}$ (CHCl$_3$) 3409, 1785, 1738 and 1684 cm$^{-1}$.

(g) 4-Methoxybenzyl (6R,7R)-7-amino-3-(5-methoxy-carbonyltetrahydrofuran-2-yl)ceph-3-em-4-carboxylate A solution of 4-methoxybenzyl (6R,7R)-3-[(2RS,5SR)-5-methoxycarbonyltetrahydrofuran-2-yl]-3-phenylacetamidoceph-3-em-4-carboxylate (497 mg) in dichloromethane (7.2 ml) was cooled to −15 to −16° C. and N-methylmorpholine (0.197 ml) was added followed by phosphorus pentachloride in dichloromethane (7.0 ml of a solution containing 40 mg ml$^{-1}$). The mixture was stirred at the same temperature for 0.5 h and then methanol (1.8 ml) was added and the mixture stirred at room temperature for 0.5 h. Water (2.4 ml) was added and the mixture vigorously stirred for 0.5 h. The dichloromethane was evaporated and the aqueous phase was stirred with ethyl acetate and the pH adjusted to 6.2 with dilute ammonia solution. The organic phase was washed with water, then brine, dried over magnesium sulphate and evaporated. The products were isolated by column chromatography using gradient elution (silica gel, 1:1 hexane:ethyl acetate going to neat ethyl acetate). Eluted first was 4-methoxybenzyl (6R,7R)-7-amino-3-[(2S,5R)-5-methoxycarbonyltetrahydrofuran-2-yl]ceph-3-em-4-carboxylate (41 mg); $v_{max}$ (CHCl$_3$) 1778 and 1743 cm$^{-1}$; $\delta_H$ CDCl$_3$) 1.6–2.4 (4H, m), 2.68 (2H, br s) 3.65 (1H, d, J 18.7 Hz), 3.74 (3H, s), 3.80 (3H, s), 3.89 (1H, d, J 18.7 Hz), 4.49 (1H, dd, J 3.2, 8.9 Hz), 4.79 (1H, d, J 4.7 Hz), 4.93 (1H, d, J 4.7 Hz), 5.06 (1H, dd, J 4.9, 9.8 Hz), 5.17 (2H, s), 6.89 (2H, d, J 8.6 Hz) and 7.33 (2H, d, J 8.5 Hz). Eluted next was 4-methoxybenzyl (6R,7R)-7-amino-3-[(2R,5S)-5-methoxycarbonyltetrahydrofuran-2-yl]ceph-3-em-4-carboxylate (126 mg); $v_{max}$ (CHCl$_3$) 1777 and 1742 cm$^{-1}$; $\delta_H$ (CDCl$_3$) 1.7–2.35 (4H, m), 2.44 (2H, br s), 3.59 (1H, d, J 17.8 Hz), 3.73 (3H, s), 3.80 (3H, s), 3.98 (1H, d, J 17.8 Hz), 4.51 (1H, dd, J 3.5, 8.8 Hz), 4.72 (1H, d, J 4.9 Hz), 4.94 (1H, d, J 4.9 Hz), 5.15–5.30 (3H, m), 6.88 (2H, d, J 8.7 Hz) and 7.34 (2H, d, J 8.7 Hz).

(h) 4-Methoxybenzyl (6R,7R)-3-[(2R,5S)-5-methoxycarbonyltetrahydrofuran-2-yl]-7-[2-(Z)-methoxyimino-2-(2-tritylaminothiazol-4-yl)acetamido]ceph-3-em-4-carboxylate A stirred solution of 2-(Z)methoxyimino-2-(2-tritylaminothiazol-4-yl)acetic acid hydrochloride (148 mg) and N,N-diisopropylethylamine (0.107 ml) in dimethylformamide (1 ml) was cooled to −55 to −60° C. and methanesulphonyl chloride (0.024 ml) was added. The mixture was stirred at the same temperature for 0.5 h and then a solution of 4-methoxybenzyl (6R,7R)-7-amino-3-[(2R,5S)-5-methoxy-carbonyltetrahydrofuran-2-yl]ceph-3-em-4-carboxylate (126 mg) in dimethylformamide (1 ml) was added followed by pyridine (0.023 ml). The mixture was then stirred at 0° C. for 1 h and then at room temperature for 0.5 h. The mixture was partitioned between ethyl acetate and aqueous citric acid solution, and the organic phase was washed with water, then brine, dried over magnesium sulphate and evaporated. The title compound (100 mg) was isolated by column chromatography of the residue (silica gel, 3:7 hexane:ethyl acetate as eluent); $v_{max}$ (CHCl$_3$) 3403, 1786, 1732 and 168 cm$^{-1}$; $\delta_H$ (CDCl$_3$) 1.66–2.36 (4H, m), 3.58 (1H, d, J 18.0 Hz), 3.73 (3H, s), 3.81 (3H, s), 4.02 (1H, d, J 18.0 Hz), 4.08 (3H, s), 4.53 (1H, dd, J 3.34, 8.91 Hz), 5.02 (1H, d, J 4.8 Hz), 5.18 (1H, d, J 11.8 Hz), 5.24 (1H, d, J 12.0 Hz), 5.30 (1H, dd, J 5.7, 9.9 Hz), 5.86 (1H, dd, J 4.6, 8.6 Hz), 6.72–6.83 (2H, m), 6.89 (2H, d, J 8.54 Hz), 7.01 (1H, s) and 7.25–7.4 (17H, m).

(i) Sodium (6R,7R)-7-[2-(2-aminothiazol-4-yl)-2-(Z)-methoxyiminoacetamido]-3-[(2S,5S)-5-methoxycarbonyl-tetrahydrofuran-2-yl]ceph-3-em-4-carboxylate Hydrochloric acid (0.12 ml of 1N) was added to a stirred solution of 4-methoxybenzyl (6R,7R)-3-[(2R,5S)-5-methoxycarbonyltetrahydrofuran-2-yl]-7-[2-(Z)-methoxyimino-2-(2-tritylaminothiazol-4-yl)acetamido] ceph-3-em-4-carboxylate (100 mg) in 98% formic acid (2 ml). The mixture was stirred at room temperature for 0.5 h and then concentrated hydrochloric acid (0.1 ml) was added, and the mixture stirred for a further 1 h at room temperature. The solid was then filtered off and the filter cake washed with 90% formic acid. The combined filtrates were evaporated and toluene evaporated from the residue twice. The residue was stirred with water and the pH adjusted to 6.2 with saturated aqueous sodium bicarbonate. The solution was filtered and evaporated and the product isolated by column chromatography of the residue (HP20SS using water with increasing proportions of acetone as eluent). Fractions containing product were combined, evaporated and the residue dissolved in water (4 ml) and freeze-dried to give a mixture (20.7 mg) of the title compound; $v_{max}$ (KBr) 1762, 1669 and 1603 cm$^{-1}$; $\delta_H$ [(CD$_3$)$_2$SO] 1.54–2.35 (4H, m), 3.23 (1H, d, J 17.4 Hz), 3.41 (1H, d, J 17.4 Hz), 3.63 (3H, s), 3.83 (3H, s), 4.54 (1H, t, 3 6.3 Hz), 4.97 (1H, d, J 4.65 Hz), 5.15 (1H, dd, J 5.9, 9.2 Hz), 5.55 (1H, dd, J 4.6, 7.9 Hz), 6.74 (1H, s), 7.23 (2H, s) and 9.48 (1H, d, J 8.1 Hz), and the 3-(2R,5S) isomer; $\delta_H$ (inter alia), 3.66(s), 3.84(s), 4.42 (dd, J 3.5, 9.0 Hz), 5.36 (dd, J 6.1, 9.7 Hz), 6.76(s) and 9.53 (d, J 8.3 Hz).

(j) 4-Methoxybenzyl (6R,7R)-3-[(2S,5R)-5-methoxycarbonyltetrahydrofuran-2-yl]-7-[2-(2-aminothiazol-4-yl)-2-(Z)-methoxyiminoacetamido]ceph-3-em-4-carboxylate A stirred solution of 2-(2-aminothiazol-4-yl)-2-(Z)-methoxyiminoacetic acid (20.1 mg) and N,N-diisopropylethylamine (0.0176 ml) in dimethylformamide (0.3 ml) was cooled to −55 to −60° C. and methanesulphonyl chloride (0.0081 ml) was added. The mixture was stirred at the same temperature for 0.5 h and then a solution of 4-methoxybenzyl (6R,7R)-7-amino-3-[(2S,5R)-5-methoxycarbonyltetrahydrofuran-2-yl]ceph-3-em-4-carboxylate (41 mg) in dimethylformamide (0.3 ml) was added followed by pyridine (0.0073 ml). The mixture was then stored at 0° C. for 1 h and then at room temperature for 0.5 h. The reaction mixture was partitioned between ethyl acetate and aqueous citric acid solution and the organic phase washed with water and brine. The solution was dried over magnesium sulphate and evaporated, and the title compound (31 mg) isolated by column chromatography of the residue (silica gel, ethyl acetate as eluent); $v_{max}$ (CHCl$_3$) 3496, 3397, 1784, 1733 and 1684 cm$^{-1}$.

(k) Sodium (6R,7B)-7-[2-(2-aminothiazol-4-yl)-2-(Z)-methoxyiminoacetamido]-3-[(2S,5R)-5-methoxycarbonyl-tetrahydrofuran-2-yl]ceph-3-em-4-carboxylate A stirred solution of anisole (0.75 ml) and dichloromethane (0.38 ml) was cooled to −20° C. and aluminium chloride (19 mg) was added. The mixture was stirred at the same temperature for 15 min. and then cooled to −40° C., and then a solution of 4-methoxybenzyl (6R,7R)-3-[(2S,5R)-5-methoxycarbonyl-tetrahydrofuran-2-yl]-7-[2-(2-aminothiazol-4-yl)-2-(Z)-methoxyiminoacetamido]ceph-3-em-4-carboxylate (31 mg) in dichloromethane (2.5 ml) was added and the mixture stirred at the same temperature for 5 min. Trisodium citrate (1.64 ml of 0.5M solution) was then added and the mixture stirred for 10 min at room temperature. The aqueous phase was separated and washed twice with dichloromethane. The solution was evaporated and the product isolated by column chromatography of the residue (HP20SS, water with increasing proportions of acetone as eluent). Fractions containing product were combined, evaporated and the residue dissolved in water (3 ml) and freeze dried to give the title compound (12 mg); $v_{max}$ (KBr) 1762, 1670 and 1604 cm$^{-1}$; $\delta_H$ [(CD$_3$)$_2$SO] 1.50–1.63 (1H, m), 1.90–2.26 (3H, m), 3.30–3.47 (2H, m), 3.65 (3H, s), 3.83 (3H, s), 4.39 (1H, dd, J 3.4, 8.7 Hz), 4.98 (1H, d, J 4.8 Hz), 5.0 (1H, dd, J 5.1, 9.8 Hz), 5.52 (1H, dd, J 4.7, 8.2 Hz), 6.75 (1H, s), 7.24 (2H, s) and 9.49 (1H, d, J 8.1 Hz).

EXAMPLE 31

4-Methoxybenzyl (6R,7R)-3-(5-acetoxymethyltetrahydrofuran-2-yl)-7-phenylacetamidoceph-3-em-4-carboxylate (a) 5-Acetoxymethylfuran-2-carboxylic acid A mixture of 5-hydroxymethylfuran-2-carboxylic acid (5.90 g), dry dichloromethane (100 ml), pyridine (6.71 ml), 4-dimethylaminopyridine (507 mg), and acetic anhydride (4.21 ml) was stirred for 2 hours at room temperature. The mixture was diluted with ethyl acetate and washed with 5M hydrochloric acid and brine (3 times), dried ($MgSO_4$), and evaporated. The residue was re-evaporated twice from dry toluene to give the title acid as a solid (5.00 g); $\delta_H$ [($CD_3$)$_2CO$] 2.05 (3H, s), 5.11 (2H, s), 6.62 (1H, d, J 4 Hz), 7.17 (1H, d, J 4 Hz) and 8.31 (1H, br S).

(b) (2RS,5SR)-5-Acetoxymethyltetrahydrofuran-2-carboxylic acid

A solution of 5-acetoxymethylfuran-2-carboxylic acid (5.00 g) in ethyl acetate (250 ml) was stirred with decolourising charcoal (5.0 g) for 10 mins. The mixture was filtered through Kieselguhr and the residue was washed with ethyl acetate (30 ml). The combined filtrates were hydrogenated over 5% rhodium on carbon (2.5 g) until hydrogen uptake ceased. The mixture was filtered through Kieselguhr and the residue was washed with ethyl acetate (30 ml). The combined filtrates were evaporated to give the title acid as an oil (3.64 g); $v_{max}$ (Film) 3700–2800 and 1742 cm$^{-1}$; $\delta_H$ [($CD_3$)$_2CO$] 1.4–2.5 and 2.00 (7H, m+s), 3.9–4.55 (4H, m) and 7.52 (1H, br s). [Mass spectrum: M$^+$ (188), MH$^+$ (189)].

(c) (2RS,5SR)-2-Acetoxymethyl-5-bromoacetyltetrahydrofuran

Dry DMF (1 drop) was added to a stirred mixture of the acid from Example 31(b) (500 mg) and oxalyl chloride (0.35 ml) in dry dichloromethane (10 ml). After stirring at room temperature for 1 hour the mixture was evaporated and the residue was re-evaporated from dry dichloromethane (2×2 ml) to give the acid chloride as an oil; $v_{max}$ (Film) 1815, 1785 and 1744 cm$^{-1}$.

The acid chloride was redissolved in dry dichloromethane (10 ml) and treated sequentially with diazomethane (from N-methyl-N-nitrosotoluene-4-sulphonamide, 1.65 g) and 48% aqueous hydrogen bromide (0.5 ml) as for Example 6(a). After stirring at ice bath temperature for 10 mins the mixture was washed with water (2×3 ml), dried ($MgSO_4$), and evaporated to approximately 5 ml to provide a solution of the title bromoketone; $v_{max}$ ($CH_2Cl_2$) 1738 cm$^{-1}$.

(d) (3R,4R)-4-[(2RS,5SR)-5-Acetoxymethyltetrahydrofuran-2-ylcarbonylmethylthio]-3-phenylacetamidoazetidin-2-one Anhydrous potassium carbonate (183 mg) was added portionwise, over 1 minute, to a stirred, ice bath cooled mixture of (3R,4R)-4-mercapto-3-phenylacetamidoazetidin-2-one (627 mg), dry DMF (5 ml), and the dichloromethane solution of the bromoketone from Example 31(c). After 15 minutes the cooling bath was removed and the mixture was stirred for an additional 15 mins. The mixture was diluted with ethyl acetate (30 ml) and was washed with 5% citric acid (5 ml), brine (5 ml), saturated $NaHCO_3$ (5 ml), and brine (3×5 ml). The dried ($MgSO_4$) organic layer was evaporated and the residue was chromatographed on silica gel eluting with ethyl acetate/hexane mixtures and neat ethyl acetate to give the title azetidinones as a gum (495 mg); $v_{max}$ ($CHCl_3$) 3411, 3324 br, 1778, 1734 and 1673 cm$^{-1}$. [Mass spectrum: +ve ion (3-nitrobenzyl alcohol, sodium acetate) MNa$^+$ (443)].

(e) 4-Methoxybenzyl (RS)-2-[(3R,4R)-4-[(2RS,5SR)-5-acetoxymethyltetrahydrofuran-2-ylcarbonylmethylthio]-3-phenylacetamidoazetidin-2-on-1-yl]-2-hydroxyacetate A mixture of the product from Example 31(d) (490 mg), 4-methoxybenzyl glyoxylate monohydrate (272 mg), benzene (15 ml), and dioxan (2 ml) was heated for 1 hour at reflux with provision for the azeotropic removal of water (Dean and Stark apparatus containing molecular sieves 4A). The mixture was cooled to room temperature and treated with triethylamine (0.016 ml). After stirring at room temperature for 1 hour the mixture was evaporated to give the title compound as a gum; $v_{max}$ ($CHCl_3$) 3613–3159, 1778, 1740 and 1676 cm$^{-1}$.

(f) 4-Methoxybenzyl (RS)-2-[(3R,4R)-4-[(2RS,5SR)-5-acetoxymethyltetrahydrofuran-2-ylcarbonylmethylthio]-3-phenylacetamidoazetitin-2-on-1-yl]-2-chloroacetate The compound from Example 31(e) was dissolved in dry THF (20 ml), cooled to −10° C., and treated with 2,6-lutidine (0.20 ml) and thionyl chloride (0.13 ml). After stirring at −10° C. for 10 minutes the mixture was diluted with dry toluene (10 ml), filtered, and the residue was washed with dry toluene (10 ml). The combined filtrates were evaporated and the residue was re-evaporated from dry toluene (2×3 ml) to give the title compound as a gum; $v_{max}$ ($CHCl_3$) 1785, 1742 and 1681 cm$^{-1}$.

(g) 4-Methoxybenzyl 2-[(3R,4R)-4-[(2RS,5SR)-5-acetoxy-methyltetrahydrofuran-2-ylcarbonylmethylthio]-3-phenylacetamidoazetidin-2-on-1-yl]-2-tri-n-butyl-phosphoranylideneacetate Tri-n-butylphosphine (0.64 ml) was added, dropwise over 2 minutes, to a stirred solution of the compound from Example 31(f) in dry dioxan (10 ml) at room temperature. After stirring at room temperature for 1 hour the mixture was evaporated and the residue was diluted with ethyl acetate and washed with saturated $NaHCO_3$ (5 ml) and brine (3×5 ml). The dried ($MgSO_4$) organic layer was evaporated and the residue was chromatographed on silica gel eluting with ethyl acetate/hexane mixtures and neat ethyl acetate to give the title ohosohorane as a gum (517 mg); $v_{max}$ ($CHCl_3$) 3419, 1749, 1672 and 1611 cm$^{-1}$.

(h) 4-Methoxybenzyl (6R,7R)-3-(5-acetoxymethyltetrahydrofuran-2-yl)-7-phenylacetamidoceph-3-em-4-carboxylate A solution of the phosphorane from Example 31(g) (517 mg) in dry toluene (100 ml) was heated at reflux under dry argon for 8 hours and evaporated the residue was chromatographed on silica gel eluting with ethyl acetate/hexane mixtures to give two fractions. The less polar fraction contained 4-methoxybenzyl (6R,7R)-3-[(2S,5R)-5-acetoxymethyltetrahydro-furan-2-yl]-7-phenylacetamidoceph-3-em-4-carboxylate, a foam (105 mg); $v_{max}$ ($CHCl_3$) 3410, 1784, 1726 and 1683 cm$^{-1}$; $\delta_H$ ($CDCl_3$) 1.53–1.83 (3H, m), 2.09 (3H, s), 2.19–2.36 (1H, m), 3.30 and 3.55 (2H, ABq, J 18.9 Hz), 3.60 and 3.69 (2H, ABq, J 16.2 Hz), 3.81 (3H, s), 4.01–4.21 (3H, m), 4.90 (1H, d, J 4.8 Hz), 4.96 (1H, dd, J 8.3, 6.7 Hz), 5.12 and 5.17 (2H, AA'q, J 12.5 Hz), 5.81 (1H, dd, J 9.2, 4.8 Hz), 5.97 (1H, d, J 9.2 Hz), 6.85–6.92 (2H, m), 7.25–7.41 (7H, m). [Mass spectrum: +ve ion (3-nitrobenzyl alcohol, sodium acetate) MH$^+$ (581), MNa$^+$ (603)]. The more polar fraction contained 4-methoxybenzyl (6R,7R)-3-[(2R,5S)-5-acetoxymethyltetrahydrofuran-2-yl]-7-phenylacetamidoceph-3-em-4-carboxylate, a solid (191 mg), m.p. 185–187° C. (needles ex ethyl acetate/hexane); $v_{max}$ ($CHCl_3$) 3407, 1785, 1731 and 1682 cm$^{-1}$; $\delta_H$ $CDCl_3$) 1.53–1.78 (2H, m), 1.90–2.05 (2H, m), 2.08 (3H, s), 3.35 and 3.57 (2H, ABq, J 18.0 Hz), 3.61 and 3.69 (2H, ABq, J 16.2 Hz), 3.80 (3H, s), 4.01–4.19 (3H, m), 4.91 (1H, d, J 4.8 Hz), 5.12–5.27 (3H, m), 5.74 (1H, dd, J 4.8, 9.0 Hz), 6.04 (1H, d, J 9.0 Hz), 6.85–6.91 (2H, m), 7.25–7.41 (7H, m). [Mass spectrum: +ve ion (3-nitrobenzyl alcohol, sodium acetate) MH$^+$ (581), MNa$^+$ (603)].

EXAMPLE 32
Sodium (6R,7R)-7-[2-(2-Aminothiazol-4-yl)-2-(Z)-methoxyiminoacetamido]-3-[3-methyltetrahydrofuran-2-yl]ceph-3-em-4-carboxylate (a) (2RS, 3SR)-3-Methyl-2-Tetrahydrofuroic acid 3-Methyl-2-furoic acid (5 g) in ethyl acetate (100 ml) and 5% rhodium on charcoal catalyst (0.5 g) were hydrogenated at ambient temperature and the atmosphere for 6–7 h. The catalyst was filtered off and replaced with a further quantity (1 g) of catalyst. The reaction mixture was hydrogenated for a further 7 h. This procedure was repeated is again until no more hydrogen was absorbed. After filtration through kieselguhr and removal of solvent under reduced pressure, the title compound was obtained as a colourless oil (5.096 g, quant.); $v_{max}$ (CH$_2$Cl$_2$) 3674, 3377(br), 1770 and 1722 cm$^{-1}$; $\delta_H$ (CHCl$_3$) 1.08 (3H, d, J 7.1 Hz), 1.72 (1H, m), 2.16 (1H, m), 2.68 (1H, m), 3.94 (1H, m), 4.18 (1H, m), 4.47 (1H, d, J 7.5 Hz) and 9.42 (1H, v. br s, exch). [Mass spectrum: +ve ion (ammonia) MNH$_4^+$ (148)].

(b) (2RS,3SR)-2-Bromoacetyl-3-Methyltetrahydrofuran (2RS,3SR)-3-Methyl-2-tetrahydrofuroic acid 91.3 g) was converted to the acid chloride with oxalyl chloride (2.54 g, 1.75 mls) in dichloromethane (20 mls) as described in Example 1(a). Diazomethane was passed through a solution of the acid chloride in dichloromethane (20 mls), cooled in ice/water until i.r. analysis showed no starting material. Hydrobromic acid (2 mls, 49% w/v aqueous solution), was added dropwise and the reaction mixture stirred vigorously for 10 min. T.l.c. analysis showed complete conversion to the title compound. The solution was washed with water, brine and dried. The solvent was washed with water, brine and dried. The solvent was evaporated and the residue flash chromatographed on silica gel, eluting with 5 and then 10% ethyl acetate/hexane to give the product as an almost colourless oil, (1.621 g, 79%); $v_{max}$ (CH$_2$Cl$_2$) 1732 cm$^{-1}$; $\delta_H$ (CDCl$_3$) 0.96 (3H, d, 7.2 Hz), 1.70 (1H, m), 2.17 (1H, m), 2.70 (1H, m), 3.93 (1H, m), 4.12 and 4.25 (2H, ABq, J 14.7 Hz) and 4.49 (1H, d, J 7.3 Hz). [Mass spectrum: +ve ion (ammonia) MNH$_4$ (224)].

(c) 4-Methoxybenzyl (2RS)-2-Hydroxy-2-[(3R,4R)-3-phenylacetamido-4-[(2RS,3SR)-3-methyltetrahydrofuran-2-ylcarbonylmethylthio]azetidin-2-on-1-yl]acetate 4-Methoxybenzyl (2RS)-2-hydroxy-2-[(1R,5R)-3-benzyl-4-thia-2,6-diazabicyclo[3.2.0]hept-2-en-7-on-6-yl]acetate (12.66 g) was hydrolysed in 50% dichloromethane-acetone (80 ml) with toluene-4-sulphonic acid hydrate (10.22 g) in water (25 ml) as described in Example 6(b). The crude thiol thus prepared (12.942 g), in acetone (50 ml) was treated with (2RS,3SR)-2-bromoacetyl-3-methyltetrahydrofuran (6.57 g) in acetone (20 ml) for 10 min. at room temperature. Then potassium carbonate (2.08 g) was added and stirring continued for 30 min. The solution was diluted with ethyl acetate (200 ml), washed with water (2×), brine and then dried. Removal of solvent gave a yellow gum. Flash chromatography on silica gel eluting with 50, 60, 70, 80 and then 90% ethyl acetate-hexane afforded the title compound as a pale yellow foam (10.406 g, 62%); $v_{max}$ (CH$_2$Cl$_2$) 3405(br), 1780, 1744, 1683 and 1613 cm$^{-1}$.

(d) 4-Methoxybenzyl 2-[(3R,4R)-3-Phenylacetamido-4-[(2RS,3SR)-3-methyltetrahydrofuran-2-ylcarbonyl-methylthio]azetidin-2-on-1-yl]-2-tri-n-butylphosphoranylideneacetate 4-Methoxybenzyl (2RS)-2-hydroxy-2-[(3R,4R)-3-phenylacetamido-4-[(2RS,3SR)-3-methyltetrahydrofuran-2-ylcarbonylmethylthio]azetidin-2-on-1-yl]acetate (10.406 g) was converted to it's chloride with thionyl chloride (3.34 g, 2.02 ml) and 2,6-lutidine (3.009, 3.25 ml) in tetrahydrofuran (100 ml) as described in Example 6(c). The crude chloride in dioxan (80 ml) was then converted to the product with tri-n-butylphosphine (6.98 ml) also described in 6(c). Flash chromatography on silica gel afforded the title compound as a foam (6.525 g, 47%). [Mass spectrum: +ve ion (3-nitrobenzyl alcohol, sodium acetate) MNa$^+$ (763)].

(e) 4-Methoxybenzyl (6R,7R)-7-Phenylacetamido-3-[(2RS,3SR)-3-methyltetrahydrofuran-2-yl]ceph-3-em-4-carboxylate The phosphorane from Example 32(d), (6.525 g) in xylene (120 ml) heated under reflux for 6–7 h. until t.l.c. analysis (ethyl acetate) showed no more starting material. Concentration and flash chromatography on silica gel eluting with 30 and then 40% ethyl acetate in hexane gave the diastereoisomer mixture of the product as a brown foam (1.293 g, 28%); The $^1$H n.m.r. spectrum showed substantial amounts of the α-2 isomeric cephems. The crude mixture in methanol (15 ml) and dichloromethane (5 ml) was treated at room temperature with a solution of sodium metaperiodate (0.636 g) in water (5 ml) overnight and then heated to about 60° C. for 1 h. The precipitate was filtered off and the filtrate concentrated. The residue was partitioned between ethyl acetate-water. The organic phase was then dried and concentrated. The residual gum was purified by flash chromatography on silica gel, eluting with 50%, 70% ethyl acetate-hexane and then neat ethyl acetate. The sulphoxide derivative of the cephem was obtained as a yellow foam, (0.484 g, 35%). This foam was dissolved in dimethylformamide (5 ml), cooled, under argon, to −30° C. Phosphorus trichloride (0.239 g, 0.152 ml) was added and the solution stirred for ca. 1 h. The solution was then diluted with ethyl acetate and washed with water (3×) and then brine. After drying and removal of solvent the crude title compound was obtained as a brown foam, (0.441 g, 97%); a sample of the crude product was flash chromatographed on silica gel, eluting with 40%, 50% ethyl acetate-hexane and afforded the less polar isomer as a pale yellow foam; $v_{max}$ (CH$_2$Cl$_2$) 3415, 1783, 1722, 1688 and 1613 cm$^{-1}$; $\delta_H$ (CDCl$_3$) 0.76 (3H, d, J 7.2 Hz), 1.55 (1H, m), 2.14 (1H, m), 2.73 (1H, m), 3.26 and 3.55 (2H, ABq, J 18.6 Hz), 3.60–3.77 (3H, m), 3.82 (3H, s), 4.04 (1H, m), 4.90 (1H, d, J 4.8 Hz), 4.93 (1H, d, J 7.6 Hz), 5.16 (2H, s), 5.80 (1H, dd, J 4.8, 9.0 Hz), 6.04 (1H, d, J 9.0 Hz), 6.88 (2H, m) and 7.24–7.41 (7H, m). [Mass spectrum: +ve ion (3-nitrobenzyl alcohol, sodium acetate), MNa$^+$ (545)]. The second, more polar isomer was then eluted and isolated as a pale yellow solid; $v_{max}$ (CH$_2$Cl$_2$) 3414, 1782, 1726, 1688 and 1613 cm$^{-1}$; $\delta_H$ (CDCl$_3$) 0.79 (1H, d, J 7.2 Hz), 1.53 (1H, m), 2.07 (1H, m), 2.40 (1H, m), 3.24 and 3.49 (2H, ABq, J 18.1 Hz), 3.57–3.75 (3H, m), 3.82 (3H, s), 3.91 (1H, m), 4.93 (1H, d, J 4.7 Hz), 5.18 (2H, s), 5.26 (1H, d, J 6.7 Hz), 5.71 (1H, dd, J 4.7, 9.0 Hz), 6.08 (1H, d, J 9.0 Hz), 6.88 (2H, d, J 8.7 Hz) and 7.26–7.40 (7H, m). [Mass spectrum: +ve ion (3-nitrobenzyl alcohol, sodium acetate), MNa$^+$ (545)].

(f) 4-Methoxybenzyl (6R,7R)-7-Amino-3-[(2RS,3SR)-3-methyltetrahydrofuran-2-yl]ceph-3-em-4-carboxylate 4-Methoxybenzyl (6R,7R)-7-phenylacetamido-3-[(2RS, 3SR)-3-methyltetrahydrofuran-2-yl]ceph-3-em-4-carboxylate (0.692 g) in dry dichloromethane (5 ml) under argon was cooled to −20° C. This solution was then treated with 4-methylmorpholine (0.268 g, 0.291 ml) followed by a solution of phosphorus pentachloride in dichloromethane (0.415 g in 10.37 ml) in a rapid dropwise fashion. The solution was allowed to warm to −5° C. and maintained at this temperature for 0.5 h. Methanol (5 ml) was then added in one portion and the solution allowed to warm to room temperature, and stirred for 0.5 h. Water (5 ml) was then added and the solution rapidly stirred for a further 0.75 h. The dichloromethane was evaporated at reduced pressure and replaced with ethyl acetate. The pH was adjusted to 7.5 with aqueous 880 ammonia. The aqueous phase was extracted with ethyl acetate and the combined organic layers washed with brine and dried. Removal of solvent and column chromatography on silica gel eluting with 60 and then-70% ethyl acetate in hexane afforded the (2S,3R) isomer of the title compound as a pale yellow foam, (0.197 g, 37%); $\nu_{max}$ (CH$_2$Cl$_2$) 1777, 1720 and 1613 cm$^{-1}$; $\delta_H$ CDCl$_3$) 0.89 (3H, d, J 7.2 Hz), 1.56 (1H, m), 2.14 (1H, m), 2.73 (1H, m), 3.37 and 3.57 (2H, ABq, J 18.0 Hz), 3.73 (1H, m), 3.82 (3H, s), 4.05 (1H, m), 4.79 (1H, d, J 4.8 Hz), 4.93 (1H, d, 4.8 Hz), 4.98 (1H, d, J 7.6 Hz), 5.17 (2H, s), 6.88 (2H, d, J 8.6 Hz) and 7.33 (2H, d, J 8.6 Hz). [Mass spectrum: +ve ion (3-nitrobenzyl alcohol, sodium acetate) MH$^+$ (405), MNa$^+$ (427)].

The second compound to be eluted was the (2R,3S) isomer of the title compound, as a brown gum, (0.193 g, 36%); $\nu_{max}$(CH$_2$Cl$_2$) 1775, 1727 and 1613 cm$^{-1}$; $\delta_H$ CDCl$_3$) 0.84 (3H, d, J 7.0 Hz), 1.54 (1H, m), 2.06 (1H, m), 2.45 (1H, m), 3.33 and 3.64 (2H, ABq, J 17.5 Hz,), 3.71 (1H, m), 3.82 (3H, s), 3.92 (1H, m), 4.78 (1H, d, J 4.5 Hz), 4.98 (1H, d, J 4.5 Hz), 5.18 (2H, s), 5.29 (1H, d, J 8.1 Hz), 6.88 (2H, d, J 8.6 Hz) and 7.33 (2H, d, J 8.6 Hz). [Mass spectrum: +ve ion (3-nitrobenzyl alcohol, sodium acetate) MH$^+$ (405), MNa$^+$ (427)]. Also isolated was a mixture of the isomers, (0.083 g, 15%).

(g) 4-Methoxybenzyl (6R,7R)-7-[2-(2-Aminothiazol-4-yl)-2-(Z)-methoxyiminoacetamido]-3-[(2S,3R)-3-methyltetrahydrofuran-2-yl]ceph-3-em-4-carboxylate Methanesulphonyl chloride (0.04 ml) was added to 2-(2-aminothiazol-4-yl)-2-(Z)-methoxyiminoacetic acid (0.103 g) and N,N-diisopropylethylamine (0.089 ml) in DMF (1 ml) under argon at −50° C. The solution was maintained between −30° C. and −40° C. for 1 h. A solution of the (2S,3R)-isomer from Example 34(f), (0.188 g) and pyridine (0.038 ml) in DMF (1 ml) was added and the solution warmed to room temperature over 1 h. The reaction mixture was diluted with ethyl acetate, washed successively with saturated sodium hydrogencarbonate, water, brine and then dried. After removal of solvent under vacuum, the residue was flash chromatographed on siliea gel, eluting with 50, 70, 80 and then 90% ethyl acetate-hexane to give the title compound as a waxy solid, (0.227 g, 83%); $\nu_{max}$ (CH$_2$Cl$_2$) 3482, 3389, 1783, 1722, 1688, 1613 and 1516 cm$^{-1}$; $\delta_H$ (CDCl$_3$) 0.89 (3H, d, J 7.1 Hz), 1.57 (1H, m), 2.15 (1H, m), 2.76 (1H, m), 3.35 and 3.61 (2H, ABq, J 18.6 Hz), 3.74 (1H, m), 3.82 (3H, s), 4.04 (1H, m), 4.10 (3H, s), 4.98 (1H, d, J 7.6 Hz), 5.04 (1H, d, J 4.8 Hz), 5.19 (2H, s), 5.22 (2H, br s, exch.), 5.94 (1H, dd, J 4.8, 8.9 Hz, collapses to d, J 4.8 Hz on exch.), 6.91 (2H, d, J 8.6 Hz), 6.99 (1H, s), 7.20 (1H, d, J 8.9 Hz, exch.) and 7.34 (1H, d, J 8.6 Hz). [Mass spectrum: +ve ion (3-nitrobenzyl alcohol, sodium acetate) MH$^+$ (588), MNa$^+$ (610)].

(h) 4-Methoxybenzyl (6R,7R)-7-[2-(2-Aminothiazol-4-yl)-2-(Z)-methoxyiminoacetamido]-3-(2R,3S)-3-methyltetrahydrofuran-2-yl]ceph-3-em-4-carboxylate The procedure used in Example 32(g) was repeated for the (2R,3S) isomer from Example 32(h), (0.183 g); with 2-aminothiazol-4-yl)-2-(Z)-methoxyiminoacetic acid (0.1 g), N,N-diisopropylethylamine (0.087 ml), methanesulpho-nyl chloride (0.039 ml) and pyridine (0.037 ml). After work up and purification the title compound was obtained as a pale yellow foam, (0.185 g, 70%); $\nu_{max}$ (CH$_2$Cl$_2$) 3484, 3388, 1782, 1731, 1688, 1609 and 1516 cm$^{-1}$; $\delta_H$ CDCl$_3$) 0.84 (2H, d, J 7.1 hz), 1.56 (1H, m), 2.09 (1H, m), 2.46 (1H, m), 3.33 and 3.60 (2H, ABq, J 17.8 Hz), 3.73 (1H, m), 3.83 (3H, s), 3.93 (1H, m), 4.09 (3H, s), 5.07 (1H, d, J 4.6 Hz), 5.21 (2H, s), 5.30 (1H, d, J 6.9 Hz), 5.02 (2H, br s, exch.), 5.87 (1H, dd J 4.6, 8.7 Hz collapses to d, J 4.6 Hz on exch.), 6.90 (2H, d, J 8.7 Hz), 6.98 (1H, s) and 7.35 (3H, d, J 8.7 Hz overlapping m, exch). [Mass spectrum: +ve ion (3-nitrobenzyl alcohol, sodium acetate) MN (588), MNa$^+$ (610)].

(i) Sodium (6R,7R)-7-[2-(2-Aminothiatol-4-yl)-2-(Z)-methoxyininoacetamido]-3-[(2S,3R)-3-methyltetrahydrofuran-2-yl]ceph-3-em-4-carboxylate A mixture of dichloromethane (3 ml) and anisole (6 ml) under argon was cooled to −20° C. and aluminium trichloride (0.15 g) was added. The solution was stirred for 0.25 h and then cooled to −40° C. A solution of the cephem prepared in Example 32(g) in dichloromethane (6 ml) was added in one portion. T.l.c. analysis (ethyl acetate) immediately after addition showed no starting material. A solution of trisodium citrate (12 ml, 0.5M solution) was added and the mixture vigorously stirred for 10 minutes at room temperature. The aqueous phase was separated, washed twice with dichloromethane and concentrated to about 5 ml. Column chromatography on HP20SS eluting with 0, 1, 2 and 4% tetrahydrofuran in water, followed by concentration and freeze-drying of the relevant fractions afforded the title compound as an amorphous white solid, (0.134 g, 73%); $\nu_{max}$ (KBr) 1761, 1667, 1597 and 1531 cm$^{-1}$; $\delta$ (d$_6$-DMSO) 0.86 (3H, d, J 7.1 Hz), 1.48 (1H, m), 2.00 (1H, m), 2.56 (1H, m), 3.09 and 3.37 (2H, ABq, J 17.1 Hz), 3.58 (1H, m), 3.84 (3H, s), 3.41 (1H, m), 4.92 (1H, d, J 7.7 Hz), 4.96 (1H, d, J 4.6 Hz), 5.53 (1H, dd, J 4.6, 8.1 Hz, collapses to d, J 4.6 Hz on exch.), 6.74 (1H, s), 7.24 (2H, br s, exch.) and 9.57 (1H, d, J 8.1 Hz, exch.). [Mass spectrum: +ve ion (thioglycerol) MH$^+$ (490), MNa$^+$ (512)].

(j) Sodium (6R,7R)-7-[2-(2-Aminothiazol-4-yl)-2-(Z)-methoxyiminoacetamido]-3-[(2R,3S)-3-methyltetrahydrofuran-2-yl]ceph-3-em-4-carboxylate The procedure used for Example 32(i) with dichloromethane (2.5 ml), anisole (5 ml), aluminium trichloride (0.12 g) and the (2R,3S) isomer (0.178 g) was employed. Following work up with trisodium citrate (10 ml, 0.5M solution) the product was isolated and purified as described to give the title compound as an amorphous white solid, (0.117 g, 79%); $\nu_{max}$ (KBr) 1762, 1665, 1597, 1532 and 1456 cm$^{-1}$; $\delta_H$(d$_6$-DMSO) 0.86 (3H, d, J 7.0 Hz), 1.47 (1H, m), 2.00 (1H, m), 2.28 (1H, m), 3.18 and 3.38 (2H, ABq, J 16.9 Hz), 3.58 (1H, m), 3.86 (3H, s), 3.93 (1H, m), 4.99 (1H, d, J 4.5 Hz), 5.44 (1H, d, J 7.7 Hz), 5.50 (1H, dd, J 4.5, 8.6 Hz, collapses to d, J 4.5 Hz on exch.), 6.76 (1H, s), 7.25 (2H, br s, exch.) and 9.50 (1H, d, J 8.6 Hz, exch.). [Mass spectrum: +ve ion (thioglycerol) MH$^+$ (490), MNa$^+$ (512)].

EXAMPLE 33

4-Methoxybenzyl (6R,7R)-3-[tetrahydropyran-4-yl]-7-phenylacetamidoceph-3-em-4-carboxylate (a) 4-Methoxybenzyl (2RS)-2-hydroxy-2-[(3R,4R)-3-phenylacetamido-4-(tetrahydropyran-4-ylcarbonylmethylthio)azetidin-2-on-1-yl]acetate Crude 4-methoxybenzyl (2RS)-2-hydroxy-2-[(3R,4R)-4-mercapto-3-phenylacetamidoazetidin-2-on-1-yl]acetate (prepared from 4-methoxybenzyl (2RS)-2-hydroxy-2-[(1R, 5R)-3-benzyl-4-thia-2,6-diazabicyclo[3.2.0]hept-2-en-7-on-6-yl]acetate (8.35 g, 20 mmol)) was dissolved in acetone (25 ml) and treated with a solution of 4-bromoacetyltetrahydropyran (G. H. Harnest and A. Burger, *J. Amer. Chem. Soc.*, 1943, 65, 370) (4.4 g, 20 mmol). After 20 min., potassium carbonate (1.38 g, 10 mmol) was added and the mixture stirred again for a further 45 min. Excess ethyl acetate was then added and the organic solution washed with water, brine and dried over anhydrous MGSO$_4$. Evaporation of solvent and chromatography of the residue on silica gel using 50% hexane in ethyl acetate to 100% ethyl acetate gave the title compound as a pale yellow foam (8.5 g; 76%); $v_{max}$ (CHCl$_3$) 3420, 1780, 1750, 1680 and 1615 cm$^{-1}$. [Mass spectrum: +ve ion (3-nitrobenzyl alcohol, sodium acetate) MNa$^+$ (579)].

(b) 4-Methoxybenzyl 2-[(3R,4R)-3-phenylacetamido-4-[tetrahydropyran-4-ylcarbonylmethylthio]aetidin-2-on-1-yl]-2-tri-n-butylphosphoranylidene acetate A solution of thionylchloride (1.ml, 15 mmole) in THF (10 ml) was added dropwise to the hydroxy compound from Example 33(a) (5.56, 10 mmol) and 2,6-lutidine (1.75 ml, 15 mmol) in THF (30 ml) at −20° C. After stirring for 30 min. the reaction was filtered through a pad of celite and the filtrate evaporated. Toluene was added and re-evaporated to yield 4-methoxybenzyl (RS)-2-chloro-2-[(3R,4R)-3-phenylacetamido-4-[tetrahydropyran-4-ylcarbonylmethylthio]azetidin-2-on-1-yl]acetate as a dark brown oil.

The crude chloro compound was dissolved in dioxan (30 ml) and treated with tri-n-butylphosphine (5.5 ml, 22 mmol). After stirring for 1 h. at room temperature the reaction mixture was diluted with ethyl acetate and washed successively with dilute aqueous sodium bicarbonate solution, water and brine. After drying over anhydrous magnesium sulphate the solvent was evaporated. Chromatography of the residue on silica gel using ethyl acetate as eluent gave the title compound as a brown foam (6.2 g, 84%); $v_{max}$ (CHCl$_3$) 3450, 1760, 1675, 1615 and 1510 cm$^{-1}$. [Mass spectrum: +ve ion (3-nitrobenzyl alcohol, sodium acetate) MH$^+$ (741) MNa$^+$ (763)].

(c) 4-Methoxybenzyl (6R,7R)-7-phenylacetamido-3-[tetrahydropyran-4-yl]ceph-3-em-4-carboxylate A solution of the phosphorane from Example 33(b) (6 g) and benzoic acid (20 mg) in xylene (500 ml) was heated at reflux for 44 h. The reaction mixture was cooled, concentrated and the residue purified by chromatography on silica gel with 50% ethyl acetate in hexane to give the title compound as a mixture with the $\Delta^2$ cephem (1:2) (1.24 g); $v_{max}$ (CHCl$_3$) 3420, 1780, 1730, 1680 and 1615 cm$^{-1}$; $\delta_H$ (CDCl$_3$), $\Delta^3$ isomer, 1.20–1.90 (4H, m), 2.05–2.20 (1H, m), 3.10–3.40 (4H, m), 3.62 and 3.67 (2H, ABq, J 16.0 Hz), 3.81 (3H, s), 3.85–4.05 (2H, m), 4.90 (1H, d, J 4.7 Hz), 5.13 and 5.24 (2H, ABq, J 11.8 Hz), 5.77 (1H, dd, J 4.7, 9.1 Hz), 6.00 (1H, d, J 9.1 Hz), 6.89 (2H, d, J 8.6 Hz) and 7.25–7.45 (7H, m). [Mass spectrum: +ve ion (ammonia) 523 (MH$^+$), 540 (MNH$_4^+$)].

EXAMPLE 34
4-Methoxybenzyl (6R,7R)-3-[(2R,3R,4S)-3,4-dimethoxytetrahydrofuran-2-yl]-7-phenylacetamidoceph-3-em-4-carboxylate (a) 1,4-Anhydro-2,3-O,O-dimethyl-5,6-O-isopropylidene-D-glucitol 1,4-Anhydro-5,6-O-isopropylidene-D-glucitol (S. Soltzberg, R. M. Goepp, Jr., and W. Freudenberg, *J. Amer. Chem. Soc.*, 1946, 68, 919) (8.74 g, 43 mmol), methyl iodide (11 ml, 172 mmol) and silver oxide (29.9 g, 129 mmol) in DMF (50 ml) were stirred overnight, filtered through celite and evaporated in vacuo. The residue was extracted with ether, filtered through celite and evaporated to give the title compound as a colourless oil (8.26 g, 83%); $v_{max}$ (CH$_2$Cl$_2$) 1675, 1457, 1381, 1270, 1216, 1108 and 1073 cm$^{-1}$; $\delta_H$ CDCl$_3$, 250 MHz) 1.37 (3H, s), 1.43 (3H, s), 3.38 (3H, s), 3.45 (3H, s), 3.7–4.35 (8H, m).

(b) 1,4-Anhydro-2,3-O,O-dimethyl-D-glucitol

The product from Example 34(a) (8.26 g) in ethanol (32 ml) and water (8 ml) was stirred with Amberlite IR 120 (H$^+$) (20 g moist) for 4 h. then filtered and evaporated to dryness to provide the title compound as an oil (6.50 g, 95%); $v_{max}$ (CH$_2$Cl$_2$) 3583, 3460, 1462, 1108, 1179 and 1061 cm$^{-1}$; $\delta_H$ (CDCl$_3$, 250 MHz) 2.13 (br s, exch.). 3.39 (3H, s), 3.47 (3H, s), 3.65–4.0 (7H, m), 4.09 (1H, dd, J 4.63, 9.87 Hz). [Mass spectrum: +ve ion (ammonia) MH$^+$ (193), MNH$_4^+$ (210)].

(c) (2S,3R,4S)-3,4-Dimethoxytetrahydrofuran-2-yl-carboxaldehyde

Sodium metaperiodate (7.97 g, 37 mmol) in water (50 ml) was added to an ice bath cooled solution of 1,4-anhydro-2,3-O,O-dimethyl-D-glucitol (6.50 g, 34 mmol) in methanol (150 ml) and then mixture stirred 0.5 h then filtered and the filtrate evaporated in vacuo. The residue was extracted five times with dichloromethane then the combined extracts were dried (MgSO$_4$) and evaporated to give the crude aldehyde as a colourless oil (5.734 g); $v_{max}$ (CH$_2$Cl$_2$) 3445, 1735, 1463, 1194 and 1120 cm$^{-1}$; $\delta_H$ CDCl$_3$, 250 MHz), 3.38 (3H, s), 3.39 (3H, s), 3.94 (1H, d, J 3.87 Hz), 4.02 (1H, d, J 9.99 Hz), 4.14 (1H, d, J 4.77 Hz), 4.20 (1H, dd, J 3.90, 10.07 Hz), 4.39 (1H, dd, J 1.77, 4.72 Hz) and 9.65 (1H, d, J 1.80 Hz). [Mass spectrum: +ve ion (ammonia) MNH$_4^+$ (178)].

(d) (2S,3R,4S)-3,4-Dimethoxytetrahydrofuran-2-ylcarboxylic acid

Jones reagent (R. G. Curtis, I. Heilbron, E. R. H. Jones and G. F. Woods, *J. Chem. Soc.*, 1953, 457) (11 ml) was added dropwise to the aldehyde (5.73 g) from Example 34(c) in acetone (125 ml) cooled in an ice bath. After 10 minutes the orange solution was treated with propan-2-ol (2 ml), stirred a further 10 minutes then diluted with ether (125 ml), filtered through celite and evaporated in vacuo. The residue in dichloromethane was dried (MgSO$_4$), concentrated and flash chromatographed on silica gel eluting with 60, 70 and 80% ethyl acetate in hexane to give the title compound (4.68 g, 72%) as a colourless oil; $v_{max}$ (CH$_2$Cl$_2$ 3404(br), 1760, 1735, 1462, 1368, 1113, 1094 and 1056 cm$^{-1}$; $\delta_H$ (CDCl$_3$, 250 MHz) 3.40 (3H, s), 3.44 (3H, s), 3.94 (1H, d, J 3.83 Hz), 4.00 (1H, d, J 9.90 Hz), 4.07 (1H, d, J 4.16 Hz) and 4.21 (1H, dd, J 3.83, 9.85 Hz). [Mass spectrum: +ve ion (ammonia) MNH$_4^+$ (194)].

(e) (2S,3R,4S)-2-Bromoacetyl-3,4-dimethoxytetrahydrofuran

A solution of (2S,3R,4S)-3,4-dimethoxytetrahydrofuran-2-carboxylic acid (3.0 g, 17.0 mmol) in dichloromethane (30 ml) was treated with oxalyl chloride (3.0 ml, 34.4 mmol) and dimethylformamide (3 drops). The mixture was stirred for 1 h., evaporated in vacuo, dichloromethane added, and re-evaporated. The resulting acid chloride was dissolved in dichloromethane (30 ml) and cooled in an ice-bath. Diazomethane was then passed into the solution as described in Example 14(a). When the addition was complete, 48% aqueous hydrogen bromide (3.2 ml) was added, and the mixture stirred for a further 10 min. The solution was washed with water (×2), dried over MgSO$_4$ and concentrated in vacuo to yield the title compound (3.40 g, 79%); (Found: M$^+$ 251.9986. C$_3$H$_{13}$O$_4$Br requires 251.9997); $v_{max}$ (CH$_2$Cl$_2$) 1739 cm$^{-1}$; $\delta_H$ (CDCl$_3$, 250 MHz) 3.37 (3H, s), 3.39 (3H, s) and 3.41–4.70 (7H, series of m).

(f) 4-Methoxybenzyl (2RS)-2-hydroxy-2-[(3R,4R)-4-[(2S,3R,4S)-3,4-dimethoxytetrahydrofuran-2-ylcarbonylmethylthio]-3-phenylacetamidoazetidin-2-on-1-yl]acetate 4-Methoxybenzyl (RS)-2-hydroxy-2-[(1R,5R)-3-benzyl-4-thia-2,6-diazabicyclo[3.2.0]hept-2-en-7-on-6-yl]acetate (6.0 g, 14.6 mmol) in 50% acetone/dichloromethane (60 ml) was cleaved with 4-toluenesulphonic acid (5.0 g, 26.3 mmol) in water (12 ml). The product was reacted with crude bromide from Example 34(e) (3.40 g, 13.4 mmol) in acetone (70 ml) followed by potassium carbonate (1.0 g, 7.2 mmol) as described in Example 6(b). After work-up, the residue was purified by chromatography on silica gel eluting with 50, 70 and 100% ethyl acetate in hexane to yield the title compound (3.40 g, 42%); $v_{max}$ ($CH_2Cl_2$) 3400, 1781, 1735, 1682, 1613 and 1516 $cm^{-1}$. [Mass spectrum: +ve ion (3-nitrobenzyl alcohol, sodium acetate) $MNa^+$ (625)].

(g) 4-Methoxybenzyl 2-[(3R,4R)-4-[(2S,3R,4S)-3,4-dimethoxytetrahydrofuran-2-ylcarbonylmethylthio]-3-phenylacetamidoazetidin-2-on-1-yl]-2-tri-n-butyl-phosphoranylideneacetate The alcohol from Example 34(f) (3.35 g, 5.56 mmol) was treated with thionyl chloride (623 μl, 8.54 mmol) and 2,6-lutidine (995 μl, 8.54 mmol), followed by tri-n-butylphosphine (3.12 ml, 12.52 mmol) as described for Example 6(c). The product was purified by chromatography on silica gel eluting with 0 and 10% methanol in ethyl acetate to yield the title compound (2.68 g, 61%); $v_{max}$ ($CH_2Cl_2$) 1761, 1682, 1613 and 1515 $cm^{-1}$. [Mass spectrum: +ve ion (3-nitrobenzyl alcohol, sodium acetate) $MH^+$ (787), $MNa^+$ (809)].

(h) 4-Methoxybenzyl (6R,7R)-3-[(2R,3R,4S)-3,4-dimethoxytetrahydrofuran-2-yl]-7-phenylacetamidoceph-3-em-4-carboxylate A solution of the phosphorane from Example 34(g) (2.60 g, 3.30 mmol) and benzoic acid (10 mg) in toluene (40 ml) was heated to reflux for 16 h. After cooling, the solvent was evaporated in vacuo. The residue was purified by chromatography on silica gel eluting with 10, 30 and 50% ethyl acetate in hexane to yield the title compound contaminated with the Δ2-isomer (296 mg, 16%); $v_{max}$ ($CH_2Cl_2$) 3418, 1783, 1732, 1682, 1612 and 1515 $cm^{-1}$; $δ_H$, Δ3-isomer ($CDCl_3$, 250 MHz) 3.25 (3H, s), 3.31 (3H, s), 3.32–4.16 (8H, series of m), 3.80 (3H, s), 4.92 (1H, d, J 4.8 Hz), 4.98–5.28 (3H, m), 5.77 (1H, dd, J 9.2, 4.8 Hz), 6.00 (1H, br d, J 9.2 Hz, exch.), 6.88 (2H, d, J 8.6 Hz) and 7.22–7.41 (7H, m). [Mass spectrum: $M^+$ (568)].

EXAMPLE 35
2-Ethoxycarbonyl-Z-but-2-enyl (6R,7R)-7-[2-(2-Aminothiazol-4-yl)-2-(Z)-methoxyiminoacetamido]-3-[(S)-tetrahydrofuran-2-yl]ceph-3-em-4-carboxylate Sodium (6R,7R)-7-[2-(2-aminothiazol-4-yl)-2-(Z)-methoxyiminoacetamido]-3-[(S)-tetrahydrofuran-2-yl]ceph-3-em-4-carboxylate, (0.35 g) in 1-methyl-2-pyrrolidinone (4 ml) was treated with a solution of ethyl (Z)-2-bromomethylbut-2-enoate, (0.16 g) in 1-methyl-2-pyrrolidinone (1 ml) and stirred at ambient temperature overnight. The solution was diluted with ethyl acetate and washed with water (3×), brine and then dried. After removal of solvent in vacuo, the residue was purified by flash chromatography on silica gel, eluting with 70, 90% ethyl acetate-hexane and then ethyl acetate. The title compound was obtained as a pale yellow foam (0.368 g, 86%); $v_{max}$ ($CH_2Cl_2$) 3480, 3389, 3320, 1781, 1726, 1682, 1606 and 1532 $cm^{-1}$; $δ_H$ ($CDCl_3$) 1.30 (4H, t, J 7.1 Hz, overlapping M), 1.66 (1H, m), 1.97 (3H, d, J 7.3 Hz), 2.35 (1H, m), 3.33 and 3.64 (2H, ABq, J 18.7 Hz), 3.88 (2H, m), 4.08 (3H, s), 4.22 (2H, q, J 7.1 Hz), 4.93 (1H, m), 5.05 (3H, m), 5.80 (2H, br s, exch.), 5.99 (1H, dd, J 4.8, 9.0 Hz, collapses to d, J 4.8 Hz on exch.), 6.83 (1H, s), 7.21 (1H, q, J 7.3 Hz) and 7.73 (1H, d, J 9.0 Hz, exch.). [Mass spectrum: +ve ion (thioglycerol) $MH^+$ (580)].

In Vitro Biological Data
MIC (μg/ml)

| | Organism | |
|---|---|---|
| Example No. | E. coli (NCTC 1048) | S. aureus (Oxford) |
| 1 | 0.50 | 1.00 |
| 3 | 2.00 | 1.00 |
| 5 | 0.50 | 0.25 |
| 7 | 0.50 | 1.00 |
| 9 | 1.00 | 0.50 |
| 13 | 1.00 | 4.00 |
| 17 | 1.00 | 2.00 |
| 18 | 16.00 | 1.00 |
| 19 | 4.00 | 2.00 |
| 21 | 0.25 | 8.00 |
| 22 | 8.00 | 0.25 |
| 24 | 0.12 | 1.00 |
| 27 | 4.00 | 1.00 |
| 28 | >32 | 0.50 |

What is claimed is:
1. A compound of formula (II) or a salt thereof:

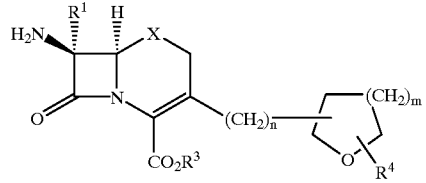

(II)

wherein $R^1$ $CO_2R^3$, $R^4$, X, m and n are as hereinbefore defined with respect to formula (I).

* * * * *